US010799493B2

(12) United States Patent
Luthringer et al.

(10) Patent No.: US 10,799,493 B2
(45) Date of Patent: *Oct. 13, 2020

(54) COMPOSITIONS AND METHODS FOR TREATING SCHIZOPHRENIA

(71) Applicant: Minerva Neurosciences, Inc., Waltham, MA (US)

(72) Inventors: Remy Luthringer, Geneva (CH); Nadine Noel, Gildwiller (FR); Sandra Werner, Ostwald (FR)

(73) Assignee: Minerva Neurosciences, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/290,234

(22) Filed: Mar. 1, 2019

(65) Prior Publication Data

US 2020/0022968 A1   Jan. 23, 2020

Related U.S. Application Data

(63) Continuation of application No. 15/651,065, filed on Jul. 17, 2017, now Pat. No. 10,258,614, which is a continuation of application No. 15/278,421, filed on Sep. 28, 2016, now Pat. No. 9,730,920, which is a continuation of application No. 14/954,264, filed on Nov. 30, 2015, now Pat. No. 9,458,130.

(60) Provisional application No. 62/248,071, filed on Oct. 29, 2015, provisional application No. 62/086,691, filed on Dec. 2, 2014.

(51) Int. Cl.
| | | |
|---|---|---|
| *A61K 31/454* | (2006.01) | |
| *C07D 401/06* | (2006.01) | |
| *A61K 9/20* | (2006.01) | |
| *A61K 9/00* | (2006.01) | |
| *A61K 47/38* | (2006.01) | |

(52) U.S. Cl.
CPC .......... *A61K 31/454* (2013.01); *A61K 9/0002* (2013.01); *A61K 9/2018* (2013.01); *A61K 9/2054* (2013.01); *A61K 47/38* (2013.01); *C07D 401/06* (2013.01)

(58) Field of Classification Search
CPC .. C07D 401/06; A61K 31/454; A61K 9/0002; A61K 9/2018; A61K 9/2054; A61K 47/38; A61K 401/06
USPC ......................................................... 514/323
See application file for complete search history.

(56) References Cited

U.S. PATENT DOCUMENTS

| | | | |
|---|---|---|---|
| 4,908,369 A | 3/1990 | Schechter et al. | |
| 7,166,617 B2 | 1/2007 | Yamabe et al. | |
| 9,458,130 B2 | 6/2016 | Luthringer et al. | |
| 9,730,920 B2 | 8/2017 | Luthringer et al. | |
| 9,732,059 B2 | 8/2017 | Luthringer et al. | |
| 10,258,614 B2 | 4/2019 | Luthringer et al. | |
| 2003/0212094 A1 | 11/2003 | Yamabe et al. | |
| 2010/0029726 A1 | 2/2010 | Blackaby et al. | |
| 2013/0273156 A1 | 10/2013 | Loeches Blas et al. | |
| 2013/0274289 A1 | 10/2013 | Luthringer et al. | |
| 2013/0274290 A1 | 10/2013 | Luthringer et al. | |
| 2016/0354357 A1 | 12/2016 | Luthringer et al. | |
| 2019/0038561 A1 | 2/2019 | Saoud et al. | |
| 2019/0216793 A1 | 7/2019 | Luthringer et al. | |
| 2020/0061046 A1 | 2/2020 | Luthringer | |

FOREIGN PATENT DOCUMENTS

| | | |
|---|---|---|
| EP | 1206512 A1 | 11/2002 |
| GB | 2462611 A | 2/2000 |
| WO | WO 91/06297 A1 | 5/1991 |
| WO | WO 2012/012542 A1 | 1/2012 |
| WO | WO 2012/012543 A1 | 1/2012 |
| WO | WO 2012/123922 A1 | 9/2012 |
| WO | WO 2014/011590 A2 | 1/2014 |
| WO | WO 2015/191554 A1 | 12/2015 |

OTHER PUBLICATIONS

Addington et al., "Assessing Depression in Schizophrenia: The Calgary Depression Scale," British Journal of Psychiatry (1993), 163 (suppl. 22), 39-44.
Alon, A. et al, "Identification of the gene that codes for the $\sigma_2$ receptor," PNAS, Jul. 3, 2017;114(27):7160-7165.
Ameen et al., "Negative Symptoms in the Remission Phase of Bipolar Disorder," German Journal of Psychiatry, 2007; 10: 1-7.
An energy nerve magazine, 2009, 111 (3), p. 288-292 (translation not available).

(Continued)

*Primary Examiner* — Raymond J Henley, III
(74) *Attorney, Agent, or Firm* — Cooley LLP; Heidi A. Erlacher; Thomas J. Paxton

(57) ABSTRACT

The disclosure provides a novel polymorph of Compound (I):

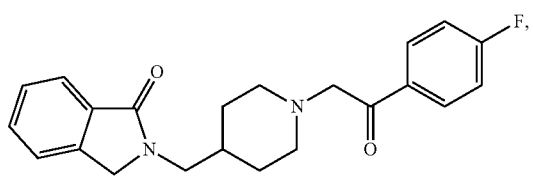

2-((1-(2-(4-Fluorophenyl)-2-oxoethyl)piperidin-4-yl)methyl)isoindolin-1-one monohydrochloride dihydrate, i.e., Form (A) of Compound (I).HCl.2H$_2$O. Pharmaceutical compositions comprising Form (A) of Compound (I).HCl.2H$_2$O and related methods of treatment are also disclosed.

20 Claims, 19 Drawing Sheets

(56) References Cited

OTHER PUBLICATIONS

Arnt, J. et al., "Do Novel Antipsychotics Have Similar Pharmacological Characteristics? A Review of the Evidence", Neuropsychopharmacology, 1998, vol. 18, No. 2, p. 63-101.

Balbach, S. et al, "Pharmaceutical evaluation of early development candidates: 'The 100 mg-approach'," International Journal of Pharmaceutics, (2004), 275, pp. 1-12.

Barrantes-Vidal et al., "Psychopathology, social adjustment and personality correlates of schizotypy clusters in a large nonclinical sample," Schizophrenia Research 122 (2010) 219-225.

Bastiaansen et al., "Diagnosing Autism Spectrum Disorders in Adults: the Use of Autism Diagnostic Observation Schedule (ADOS) Module 4," J. Autism Dev. Disord. (2011), 41:1256-1266.

Bastin, R. J. et al., "Salt Selection and Optimisation Procedures for Pharmaceutical New Chemical Entities," Organic Process & Development, 2000, 4(5), pp. 427-435.

Bi et al., "Childhood trauma interacted with BDNF Va166Met influence schizophrenic symptoms," Medicine, 2018, 97(13):e0160, 5 pages.

Bishara et al., "Upcoming Agents for the Treatment of Schizophrenia Mechanism of Action, Efficacy and Tolerability," Drugs, vol. 68, No. 16, p. 2269-2292, 2008.

Bonhaus D. et al., "[$^3$H]BIMU-1 , a 5-Hydroxytryptamine$_3$ Receptor Ligand in NG-108 Cells, Selectively Labels Sigma-2 Binding Sites in Guinea Pig Hippocampus," The Journal of Pharmacology and Experimental Therapeutics, vol. 267, No. 2, p. 961-970, 1993.

Boone et al., "Relationship between positive and negative symptoms and neuropsychological scores in frontotemporal dementia and Alzheimer's disease," Journal of the International Neuropsychological Society (2003), 9, 698-709.

Buchanan et al., "Olanzapine Treatment of Residual Positive and Negative Symptoms," American Journal of Psychiatry, 2005, vol. 162, p. 124-129.

Buchanan et al., "Positive and Negative Symptom Response to Clozapine in Schizophrenic Patients With and Without the Deficit Syndrome," American Journal of Psychiatry, 1998, vol. 155, p. 751-760.

Buckley, P.F. et al. "Pharmacological treatment of negative symptoms of schizophrenia: therapeutic opportunity or Cul-de-sac?" Acta Psychiatrica Scandinavica, vol. 115, No. 2, 2007, p. 93-100.

Caira, "Crystalline Polymorphism of Organic Compounds," Topics in Current Chemistry, Springer, Berlin, De, vol. 198, Jan. 1, 1998, pp. 163-208.

Chaudhury et al., "Neuropsychiatric Sequelae of Head Injury," Indian Journal of Neurotrauma (IJNT), 2005, vol. 2, No. 1, 13-21.

Cohrs, "Sleep Disturbances in Patients with Schizophrenia", CNS Drugs, (2008), vol. 22, No. 11, pp. 939-962.

Davidson, M. et al., "MIN-101: A Drug in Development for the Treatment of Negative Symptoms in Schizophrenia," Poster presentation at the 55th Annual Meeting of the American College of Neuropsychopharmacology, held Dec. 4-8, 2016 in Hollywood, Florida, available on goo.gl/MIR7Tn.

Davidson, M. et al., "MIN-101: A sigma2 and 5HT2 antagonist drug in development for the treatment of symptomatically stable schizophrenia patients with negative symptoms," Oral Presentation at the 55th Annual Meeting of the American College of Neuropsychopharmacology, Dec. 4-8, 2016 in Hollywood, Florida, available on goo.Jl/xF5rdR.

Dow, "Using Dow Excipients for Controlled Release of Drugs in Hydrophilic Matrix Systems," Dow, Sep. 2006, 36 pages.

Dumont M. et al., "Interaction of 1,3-di(2-[5-$^3$H]tolyl) guanidine with $\sigma_2$ binding sites in rat heart membrane preparations," European Journal of Pharmacology, 1991, vol. 209, pp. 245-248.

Dutheil et al., "Xenobiotic metabolozing enzymes in the central nervous system: Contribution of cytochrome P450 enzymes in normal and pathological human brain," Biochimie, vol. 90, Issue 3, Mar. 2008, pp. 426-436.

Evonik Industries, "It's not Rocket Science to Reach Higher Coating Efficiency: PlasACRYL makes it possible," Evonik Industries AG, Oct. 2012, 8 pages.

Foussias, G. et al., "Negative Symptoms in Schizophrenia: Avolition and Occam's Razor," Schizophrenia Bulletin, 2010, vol. 36, No. 2, p. 359-369.

Galynker et al., "Negative Symptoms in Patients With Major Depressive Disorder: A Preliminary Report," Neuropsychiatry, Neuropsychology, and Behavioral Neurology, Jul. 2000, vol. 13, No. 3, 171-176.

Galynker et al., "Negative Symptoms in Stroke Patients and Length of Hospital Stay," The Journal of Nervous & Mental Disease, 1997, vol. 185(10), pp. 616-621.

Garza H. et al., "Characterization of a (+)-Azidophenazocine-Sensitive Sigma Receptor on Splenic Lymphocytes," The Journal of Immunology, 1993, vol. 151, p. 4672-4680.

Getz et al., "Negative Symptoms in Temporal Lobe Epilepsy," Am. J. Psychiatry, 2002; 159:644-651.

Giacobbo et al., "Brain-Derived Neurotrophic Factor in Brain Disorders: Focus on Neuroinflammation," Molecular Neurobiology, 2019, vol. 56, Issue 5, pp. 3295-3312.

Gilmore, D. et al., "Review of the Pharmacological and Clinical Profile of Rimcazole", CNS Drug Reviews, 2004, vol. 10, No. 1, pp. 1-22.

Hashimoto et al., "Interactions of erythro-ifenprodil, threo-ifenprodil, erythro-iodoifenprodil, and eliprodil with subtypes of sigma receptors" European Journal of Pharmacology, 273 (1995), pp. 307-310.

Hashimoto et al., "Sigma Receptor Ligands: Possible Application as Therapeutic Drugs and as Radiopharmaceuticals," Current Pharmaceutical Design, 2006, vol. 12, No. 30, pp. 3857-3876.

Herbener et al., "Longitudinal Assessment of Negative Symptoms in Schizophrenia/Schizoaffective Patients, Other Psychotic Patients, and Depressed Patients," Schizophrenia Bulletin, 2001, 27(3):527-537.

Hussan et al., "A review on recent advances of enteric coating," IOSR Journal of Pharmacy, vol. 2, Issue 6, 2012, 5-11.

Ishihara et al., Japanese Journal of Neuropsychopharmacology, (2002), vol. 22, No. 1, pp. 23-30.

Jaen J. et al., "Evaluation of the Effects of the Enantiomers of Reduced Haloperidol, Azaperol, and Related 4-Amino-1-arylbutanols on Dopamine and $\sigma$ Receptors," J. Med. Chem., 1993, vol. 36, pp. 3929-3936.

Jeste, "Schizoaffective Disorder," National Alliance on Mental Illness, http://www.nami.org/Template.cfm?Section=By_Illness&Template=/ContentManagement!ContentDisplay.cfm&ContentiD=23043 Wayback Internet Archive, (Nov. 7, 2008).

Jones C. et al., "Animal Models of Schizophrenia," British Journal of Pharmacology, 2011, vol. 164, pp. 1162-1194.

Kamel et al., "Pharmaceutical significance of cellulose: A review," eXPRESS Polymer Letters, (2008) vol. 2, No. 11, pp. 758-778.

Kay, "The Positive and Negative Syndrome Scale (PANSS) for Schizophrenia," Schizophrenia Bulletin, 1987, vol. 13, No. 2, pp. 261-276.

Kropp et al., "Cytochrome P-450 2D6 and 2C19 polymorphisms and length of hospitalization in psychiatry", Clinical Laboratory, 2006, 52(5-6), pp. 237-240. Abstract.

Luthringer, R., "Comparison of Three Sigma2 Ligands on Negative and Positive Symptoms of Schizophrenia", Exhibit C to Supplemental Declaration or Remy Luthringer Under 37 C.F.R. 1.132, Submitted Jan. 17, 2017 in U.S. Appl. No. 13/810,772, 14 pages.

Marder et al., "Aripiprazole in the treatment of schizophrenia: safety and tolerability in short-term, placebo-controlled trials," Schizophrenia Research, 2003, vol. 61, pp. 123-136.

Mash et al., "Sigma Receptors Are Associated With Cortical Limbic Areas in the Primate Brain," Synapse, 1992, vol. 12, pp. 195-205.

Maurice et al., "The attenuation of learning impairments induced after exposure to CO or trimethyltin in mice by sigma($\sigma$) receptor ligands involves both $\sigma_1$ and $\sigma_2$ sites," British Journal of Pharmacology, May 1999, 127(2), pp. 335-342.

Meltzer et al., "Lack of Involvement of Haloperidol-Sensitive Sigma Binding Sites in Modulation of Dopamine Activity and

(56) References Cited

OTHER PUBLICATIONS

Induction of Dystonias by Antipsychotic Drugs," Neuropharmacology, 1992, vol. 31, No. 9, pp. 961-967.
Modell S. et al., "Efficacy and Safety of an Opiate Sigma-Receptor Antagonist (SL 82.0715) in Schizophrenic Patients with Negative Symptoms: and Open Dose-Tange Study," Pharmacopsychiat., 1996, vol. 29, pp. 63-66.
Nieto et al., "BDNF and schizophrenia: from neurodevelopment to neuronal plasticity, learning and memory," Frontiers in Psychiatry, Jun. 2013, 4:45, 1-10.
Nokhodchi et al., "The Role of Oral Controlled Release matrix Tablets in Drug Delivery Systems", BioImpacts, 2012, 2(4), pp. 175-187.
Paykel, Eugene S., "Basic Concepts of Depression", Dialogues in Clinical Neuroscience, 2008, vol. 10, No. 3, pp. 279-289.
Quirion et al., "A proposal for the classification of sigma binding sites", TiPS, Mar. 1992, vol. 13, pp. 85-86.
Sahlholm, K. et al., "The dopamine stabilizers ACR16 and (−)-O5U6162 display nanomolar affinities at the σ-1 receptor," Mol. Psychiatry. (2013);18(1):12-14.
Schwarcz, G. et al., "Open Label Evaluation of the Novel Antipsychotic Compound BW234U in Chronic Schizophrenics," Drug Development Research, 1985, vol. 5, pp. 387-393.
SEC Form 8-K filed Jun. 6, 2016, Minerva Neurosciences. Inc.
Seo, M.K. et al., "Effects of Antipsychotic Drugs on the Epigenetic Modification of Brain-Derived Neurotrophic Factor Gene Expression in the Hippocampi of Chronic Restraint Stress Rats," Neural Plasticity, 2018, vol. 2018, Article ID 2682037, 10 pages.
Sie, M., "An Update on Sleep Disorders and Their Treatment," Progress in Neurology and Psychiatry, 2010, 14(3): pp. 9-20.
Singhal, D et al., "Drug Polymorphism and Dosage Form Design: A practical perspective," Advanced Drug Delivery Reviews, 2004, 56, pp. 335-347.
Siris, Samuel G., "Depression in Schizophrenia: Perspective in the Era of 'Atypical' Antipsychotic Agents," Am. J. Psychiatry, Sep. 2000, vol. 157, No. 9, pp. 1379-1389.
Summary of 3rd Quarter Financial Results for year ended Mar. 31, 2010 (Unaudited); Mitsubishi Tanabe Pharma Corporation; Jan. 28, 2010, available on http://www.mt-pharma.co.jp/.
Takahashi et al., "Antipsychotics reverse abnormal EEG complexity in drug-naïve schizophrenia: A multiscale entropy analysis," NeuroImage, (2010), vol. 51, pp. 173-182.
Takasu et al., Today's Therapy 2002, vol. 44, pp. 609-612.
Tokuda, "Pharmacological action of antipsychotic drugs" Folia Pharmacologica Japonica, (2006), vol. 128, pp. 173-176. (No English translation available).
Utami et al., "BDNF (brain-derived neurotrophic factor) serum levels in schizophrenic patients with cognitive deficits," IOP Conference Series: Earth and Environmental Science, 2018, vol. 125, 012181, 6 pages.
"View of NCT00861796 on Mar. 12, 2009", ClinicalTrials.gov archive, Mar. 12, 2009 Retrieved from the Internet: URL:http://clinicaltrials.gov/archive/NCT00861796/2009_03_12.
Walker J. M. et al., "Sigma Receptors: Biology and Function," Pharmacological Reviews, 1990, vol. 42, No. 4, p. 355-402.
Werbeloff et al., "The Association between Negative Symptoms, Psychotic Experiences and Later Schizophrenia: A Population-Based Longitudinal Study," PLoS One (2015) 10(3): e0119852 12 pages.
White et al., "Empirical Assessment of the Factorial Structure of Clinical Symptoms in Schizophrenia," Psychopathology 1997:30:263-274.
Whittemore, E. et al., "Antagonism of N-Methyl-D-Aspartate Receptors by σ Site Ligands: Potency, Subtype-Selectivity and Mechanisms of Inhibition," The Journal of Pharmacology and Experimental Therapeutics, 1997, vol. 282, No. 1, p. 326-338.
Winograd-Gurvich et al., "Negative symptoms: A review of schizophrenia, melancholic depression and Parkinson's disease," Brain Research Bulletin 70 (2006) 312-331.
Yang et al., "Clinical significance of sleep EEG abnormalities in chronic schizophrenia", Schizophrenia Research, 2006, vol. 82, pp. 251-260.
Okuyama, S., Nippon Yakurigaku Zasshi, Folia Pharmacologica Japonica, 1999, vol. 114, pp. 13-23 (English abstract only).
Zhanpei, Zhen "Negative Symptoms of Schizophrenia", Foreign Medicine, Psychiatry Volume, Mar. 1988. (No English translation available).
Costa e Silva, "Sleep disorders in psychiatry," Metabolism Clinical and Experimental, 2006, 55, Supplement 2, S40-S44.
Keefe et al., "Cognitive Effects of MIN-101 in Patients With Schizophrenia and Negative Symptoms Results From a Randomized Controlled Trial," J Clin Psychiatry, May/Jun. 2018, 79:3, e1-e6.
Rusconi et al., "SSRI antidepressants and negative schizophrenic symptoms: differences between paroxetine and fluvoxamine in patients treated with olanzapine," Riv Psichiatr. Sep.-Oct. 2009;44(5):313-319 (English abstract only).
Zhou et al., "A new form of rapid binocular plasticity in adult with amblyopia," Scientific Reports, Sep. 2013, 3:2638, 5 pages.

COMPOSITIONS AND METHODS FOR TREATING SCHIZOPHRENIA

CROSS REFERENCES

This application is a continuation of U.S. application Ser. No. 15/651,065, filed Jul. 17, 2017, which issued as U.S. Pat. No. 10,258,614 on Apr. 16, 2019, which is a continuation of U.S. application Ser. No. 15/278,421, filed Sep. 28, 2016, which issued as U.S. Pat. No. 9,730,920 on Aug. 15, 2017, which is a continuation of U.S. application Ser. No. 14/954,264, filed Nov. 30, 2015, which issued as U.S. Pat. No. 9,458,130 on Oct. 4, 2016, which claims priority to, and the benefit of, U.S. Provisional Application Ser. No. 62/086,691, filed Dec. 2, 2014, and U.S. Provisional Application Ser. No. 62/248,071, filed Oct. 29, 2015, the contents of each of which are incorporated herein by reference in their entireties.

FIELD OF THE INVENTION

The present invention in some embodiments relates to compositions and methods for treating schizophrenia in a patient.

BACKGROUND OF THE INVENTION

Schizophrenia is a complex, challenging, and heterogeneous psychiatric condition, affecting up to 0.7% of the world population according to the World Health Organization (WHO, 2006). Patients suffering with schizophrenia present with a range of symptoms, including: positive symptoms, such as delusions, hallucinations, thought disorders, and agitation; negative symptoms, such as mood flatness and lack of pleasure in daily life; cognitive symptoms, such as the decreased ability to understand information and make decisions, difficulty focusing, and decreased working memory function; and sleep disorders.

The etiology of schizophrenia is not fully understood. A major explanatory hypothesis for the pathophysiology of schizophrenia is the Dopamine (DA) hypothesis, which proposes that hyperactivity of DA transmission is responsible for expressed symptoms of the disorder. This hypothesis is based on the observation that drugs effective in treating schizophrenia share the common feature of blocking DA D2 receptors. However, these so-called typical antipsychotics are associated with a very high incidence of extrapyramidal symptoms (EPS). Furthermore, negative symptoms and cognitive impairment are considered relatively unresponsive to typical antipsychotics.

Most currently approved therapies for schizophrenia show efficacy primarily in the management of positive symptoms. An estimated 4.2 million people suffered from schizophrenia in 2012 in the United States and the five major European Union markets. Of those, an estimated 48% experienced predominantly negative symptoms and 80% suffered from cognitive impairment. In addition, about 50% of patients with schizophrenia experience sleep disorders, which can further exacerbate both positive and negative symptoms.

The introduction of the so-called atypical antipsychotics in the last decade represented a significant advance in the treatment of schizophrenia. Although these atypical antipsychotics differ widely in chemical structure and receptor-binding profiles, they share a characteristic of potent antagonism of the Serotonin (5-hydroxytryptamine) type 2 receptor (5-HT2A). A high 5-HT2A:D2 affinity ratio is thought to substantially reduce the liability for inducing EPS, compared with typical antipsychotics.

However, many patients are still treatment-noncompliant despite the advantage of atypical antipsychotics of tolerability. Although the risk of EPS is clearly lower with the atypical antipsychotics, the high doses required with some atypical antipsychotics are likely to result in an increased incidence of EPS and require concomitant medications such as antiparkinson drugs.

In addition to EPS, antipsychotic medications cause a broad spectrum of side effects including sedation, anticholinergic effects, prolactin elevation, orthostatic hypotension, weight gain, altered glucose metabolism, and QTc prolongation. These side effects can affect patients' compliance with their treatment regimen. It should be noted that non-compliance with treatment regimen is a primary reason for relapse of the disease.

Although atypical antipsychotics offer advantages over typical antipsychotics in terms of symptom alleviation and side effect profile, these differences are generally modest. A certain population of patients still remains refractory to all currently available antipsychotics. Newer agents to address these issues continue to be sought.

The disclosure provides compositions, methods, and kits to address this long-felt and unmet need for a treatment for schizophrenia that is effective for all subjects, particularly those who are not effectively treated by currently available therapies. The compositions, methods, and kits of the disclosure lead to greater patient compliance.

SUMMARY

The disclosure provides a novel polymorph of Compound (I),

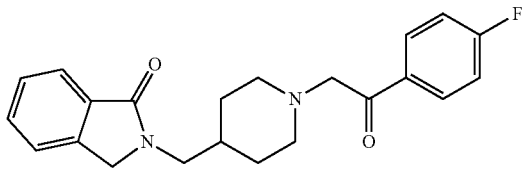 [SMILES: O=C(CN1CCC(CN2Cc3ccccc3C2=O)CC1)c1ccc(F)cc1]

(also known as MIN-101, CYR-101 and MT-210), which has shown effectiveness in animal models of psychosis (see also U.S. Pat. No. 7,166,617, the contents of which are incorporated herein in their entirety). Compound (I) is an antipsychotic drug belonging to a new chemical class, the cyclic amido derivatives. The chemical designation is 2-((1-(2-(4-Fluorophenyl)-2-oxoethyl)piperidin-4-yl)methyl) isoindolin-1-one monohydrochloride dihydrate.

As used herein, the novel polymorph of Compound (I):

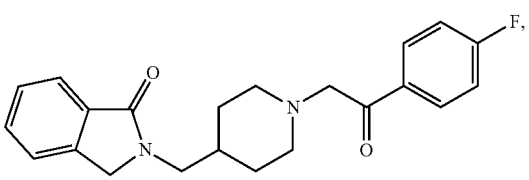 [SMILES: O=C(CN1CCC(CN2Cc3ccccc3C2=O)CC1)c1ccc(F)cc1]

2-((1-(2-(4-Fluorophenyl)-2-oxoethyl)piperidin-4-yl) methyl)isoindolin-1-one monohydrochloride dihydrate, is also referred to as Form (A) of Compound (I).HCl.2H$_2$O.

In one embodiment, Form (A) of Compound (I).HCl.2H$_2$O is characterized by XRPD.

In one embodiment, Form (A) of Compound (I).HCl.2H$_2$O is characterized by IR.

In one embodiment, Form (A) of Compound (I).HCl.2H$_2$O is characterized by $^1$H-NMR.

In one embodiment, Form (A) of Compound (I).HCl.2H$_2$O is characterized by $^{13}$C NMR.

The disclosure provides a process for preparing Form (A) of Compound (I).HCl.2H$_2$O.

The disclosure provides pharmaceutical compositions comprising Form (A) of Compound (I).HCl.2H$_2$O and a pharmaceutically acceptable diluent, excipient, or carrier.

The disclosure provides a method of treating a neuropsychiatric disease or disorder, comprising administering a therapeutically effective amount of Form (A) of Compound (I).HCl.2H$_2$O or a pharmaceutical composition thereof to a subject in need thereof.

The disclosure provides a method for treating schizophrenia, comprising administering a therapeutically effective amount of Form (A) of Compound (I).HCl.2H$_2$O or a pharmaceutical composition thereof to a subject in need thereof.

The disclosure relates to use of a pharmaceutical formulation of the invention, in the manufacture of a medicament for treating schizophrenia.

The disclosure provides a kit comprising a pharmaceutical composition comprising Form (A) of Compound (I).HCl.2H$_2$O and instructions for use.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the disclosure, suitable methods and materials are described below. All publications, patent applications, patents, and other references mentioned herein are incorporated by reference. The references cited herein are not admitted to be prior art to the claimed invention. In the case of conflict, the present specification, including definitions, will control. In addition, the materials, methods, and examples are illustrative only and are not intended to be limiting.

Other features and advantages of the disclosure will be apparent from the following detailed description and claims.

BRIEF DESCRIPTION OF THE DRAWINGS

The foregoing summary, as well as the following detailed description of the invention, will be better understood when read in conjunction with the appended drawings.

DETAILED DESCRIPTION OF THE INVENTION

The disclosure provides compositions, methods, and kits for the treatment of a neuropsychiatric disease or condition. Preferably the neuropsychiatric disease or condition is schizophrenia. Compositions and kits of the disclosure include pharmaceutical compositions. Compositions of the disclosure comprise a stable polymorph of Compound (I).HCl2H$_2$O, which is preferably Form (A) of Compound (I).HCl2H$_2$O.

Form A of Compound (I)

The disclosure pertains, at least in part, to a stable polymorph of Compound (I).HCl2H$_2$O.

In one embodiment, the polymorph of Compound (I).HCl.2H$_2$O is Form (A).

Figure 11:
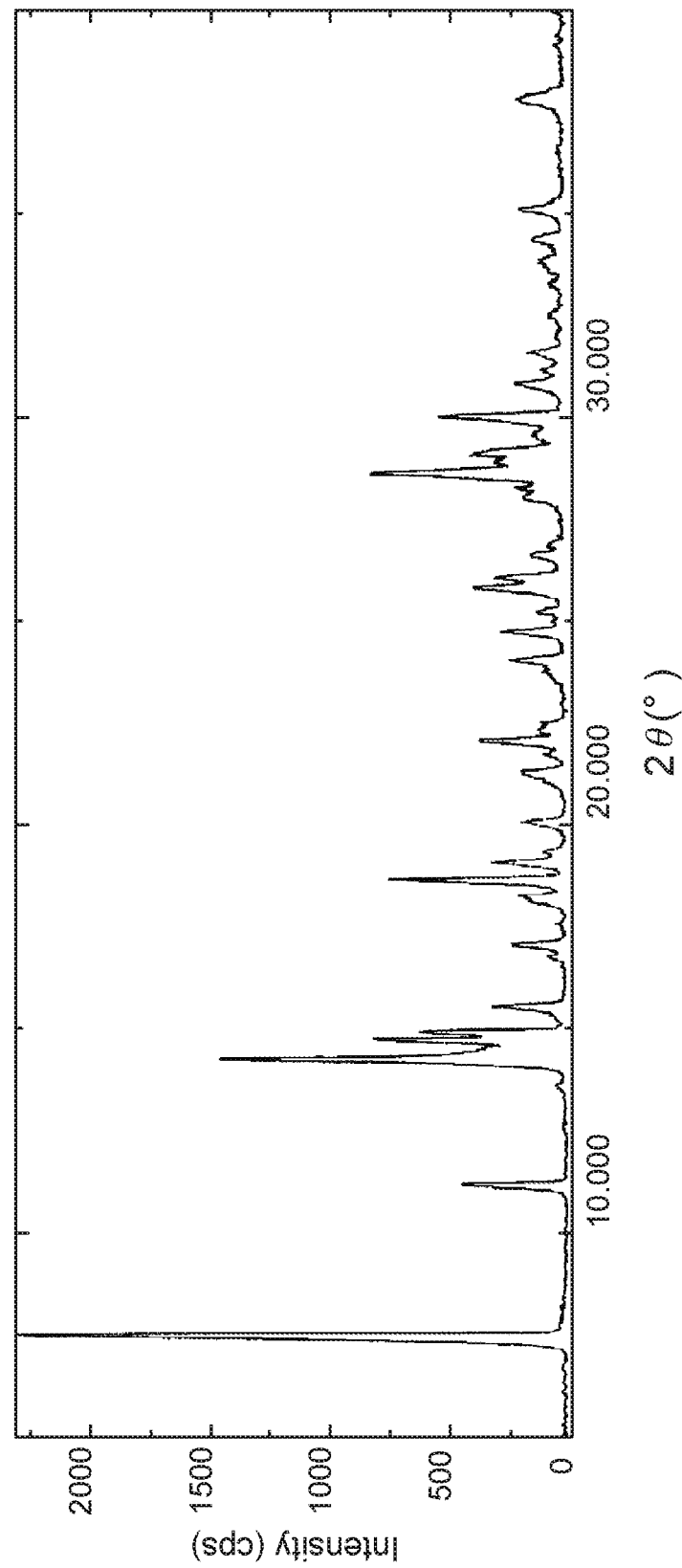
FIG. 11 is an X-ray powder diffraction of Form (A) of Compound (I).HCl.2H$_2$O.

In one embodiment, Form (A) of Compound (I).HCl.2H$_2$O has an X-ray powder diffraction pattern substantially similar to that shown in FIG. 11.

In one embodiment, Form (A) of Compound (I).HCl.2H$_2$O has X-ray powder diffraction peaks at approximately 7.6 and 14.3° 2θ using Cu Kα radiation.

In one embodiment, Form (A) has X-ray powder diffraction peaks at approximately 7.6, 14.3, and 14.7° 2θ using Cu Kα radiation.

In one embodiment, Form (A) has X-ray powder diffraction peaks at approximately 7.6, 14.3, and 27.5° 2θ using Cu Kα radiation.

In one embodiment, Form (A) has X-ray powder diffraction peaks at approximately 7.6, 14.3, 14.7, and 27.5° 2θ using Cu Kα radiation.

In one embodiment, Form (A) has X-ray powder diffraction peaks at approximately 7.6, 14.3, 14.7, 18.6, and 27.5° 2θ using Cu Kα radiation.

In one embodiment, Form (A) has X-ray powder diffraction peaks at approximately 7.6, 14.3, 14.7, 14.9, 18.6, 27.5 and 30.1° 2θ using Cu Kα radiation.

In one embodiment, Form (A) has X-ray powder diffraction peaks at approximately 7.6, 11.2, 14.3, 14.7, 14.9, 18.6, 22.0, 25.9, 27.5 and 30.1° 2θ using Cu Kα radiation.

Figure 12:
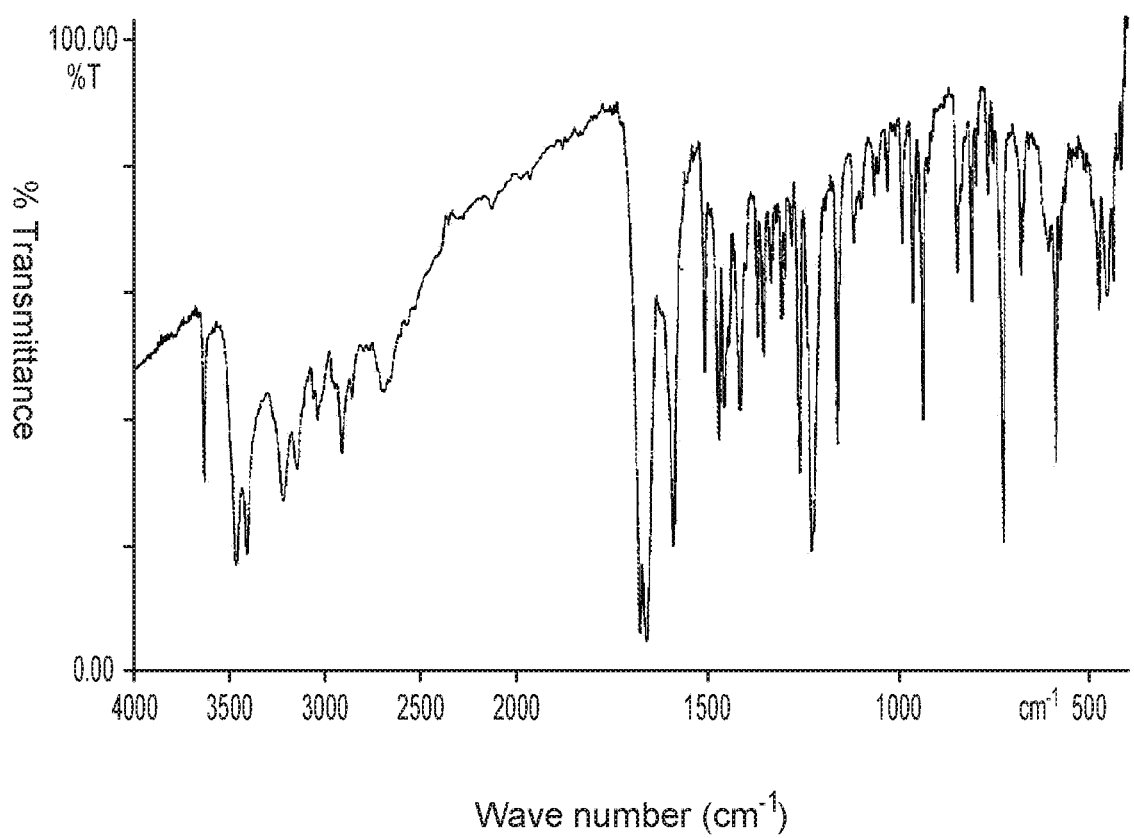
FIG. 12 is an IR spectrum of Form (A) of Compound (I).HCl.2H$_2$O.

In one embodiment, Form (A) of Compound (I).HCl.2H$_2$O has an IR absorption spectrum substantially similar to that shown in FIG. 12.

In one embodiment, Form (A) has an IR absorption spectrum with a main wave number of absorption at 2916 cm$^{-1}$.

In one embodiment, Form (A) has an IR absorption spectrum with a main wave number of absorption at 1684 cm$^{-1}$.

In one embodiment, Form (A) has an IR absorption spectrum with a main wave number of absorption at 1665 cm$^{-1}$.

In one embodiment, Form (A) has an IR absorption spectrum with a main wave number of absorption at 1594 cm$^{-1}$.

In one embodiment, Form (A) has an IR absorption spectrum with a main wave number of absorption at 1235 cm$^{-1}$.

In one embodiment, Form (A) has an IR absorption spectrum with a main wave number of absorption at 1684 and 1665 cm$^{-1}$.

In one embodiment, Form (A) has an IR absorption spectrum with main wave numbers of absorption at 2916, 1684, and 1665 cm$^{-1}$.

In one embodiment, Form (A) has an IR absorption spectrum with main wave numbers of absorption at 2916, 1684, and 1665 cm$^{-1}$.

In one embodiment, Form (A) has an IR absorption spectrum with main wave numbers of absorption at 2916, 1594, and 1235 cm$^{-1}$.

In one embodiment, Form (A) has an IR absorption spectrum with main wave numbers of absorption at 2916, 1684, 1665, and 1235 cm$^{-1}$.

In one embodiment, Form (A) has an IR absorption spectrum with main wave numbers of absorption at 2916, 1684, 1665, 1594, and 1235 cm$^{-1}$.

Figure 13:
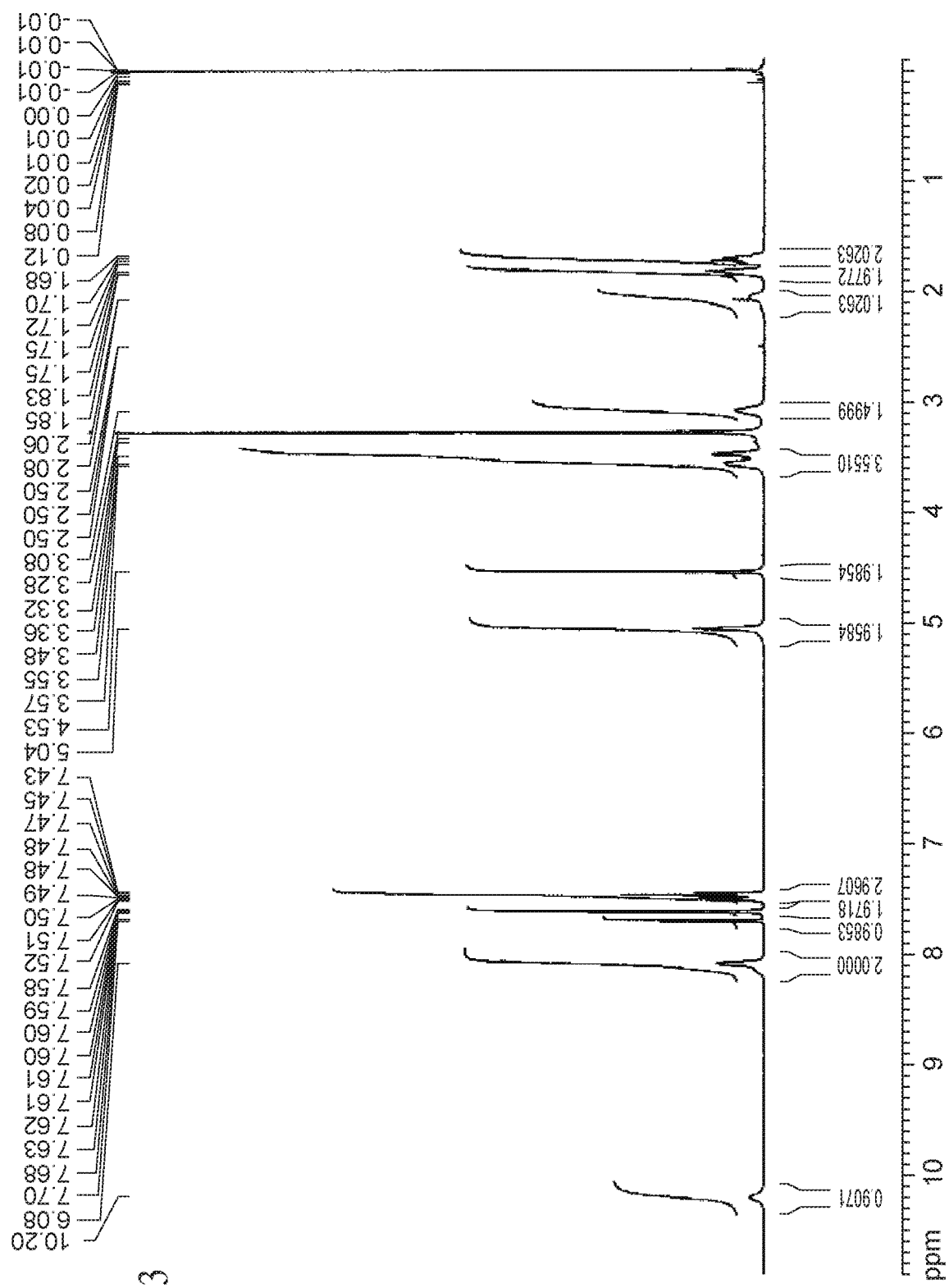
FIG. 13 is a $^1$H-NMR spectrum of Form (A) of Compound (I).HCl.2H$_2$O.

In one embodiment, Form (A) of Compound (I).HCl.2H$_2$O has a $^1$H NMR spectrum substantially similar to that shown in FIG. 13.

Figure 14:
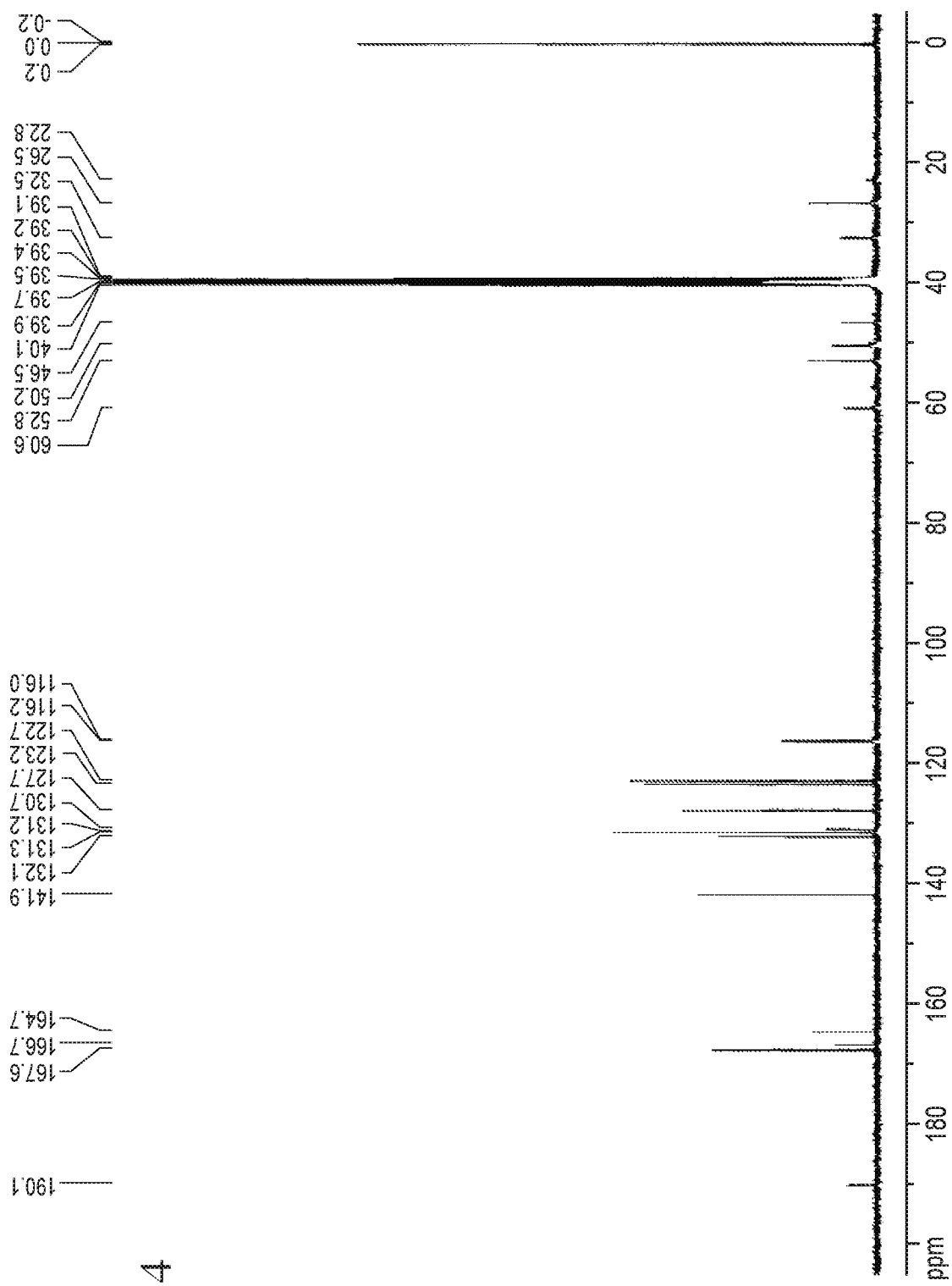
FIG. 14 is a $^{13}$C-NMR spectrum of Form (A) of Compound (I).HCl.2H$_2$O.
Figure 15:
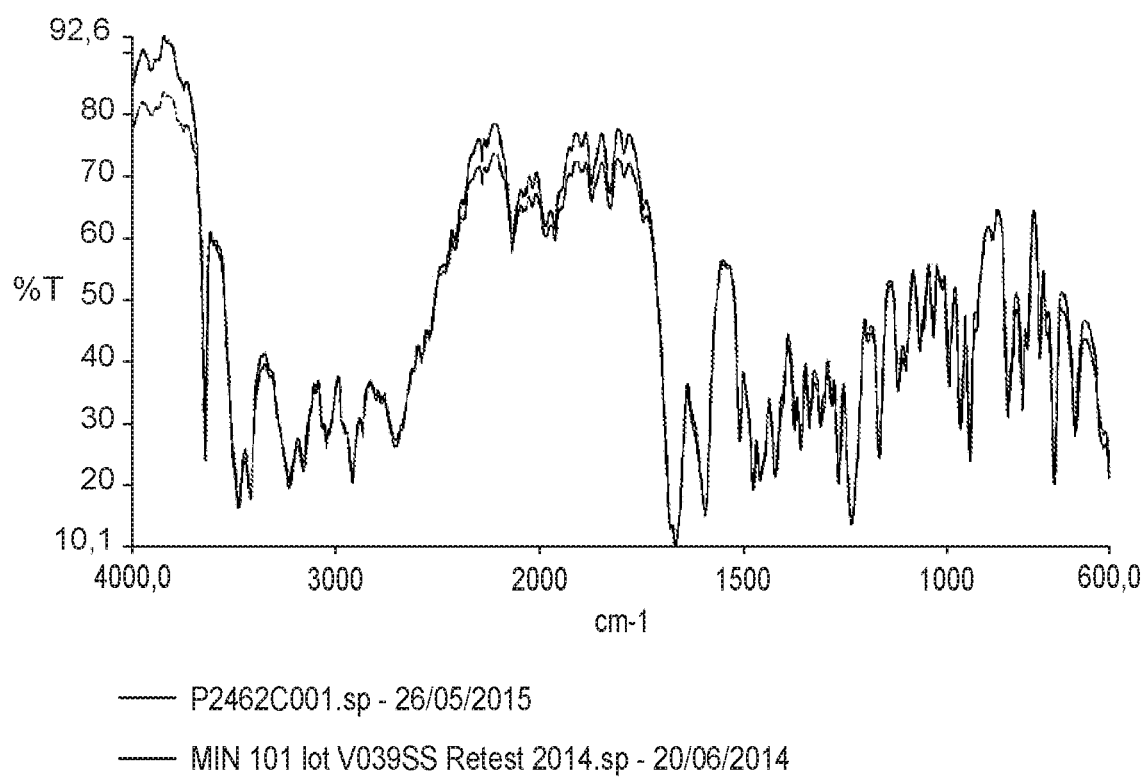
FIG. 15 is an IR spectrum comparison between batch C001 and V039SS (secondary reference standard from MTPC).
Figure 16:
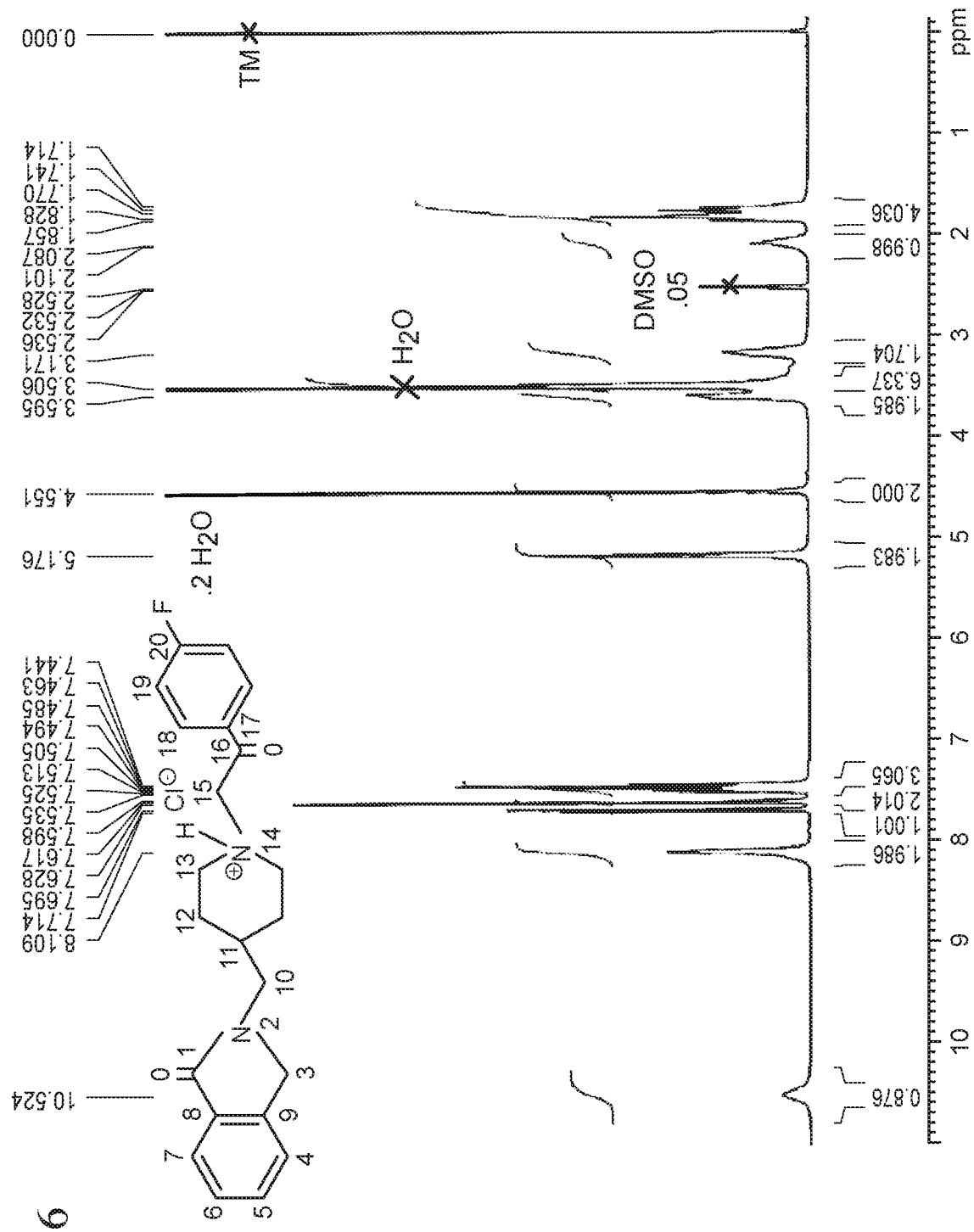
FIG. 16 is a $^1$H-NMR spectrum of batch C001 (from PCAS).
Figure 17:
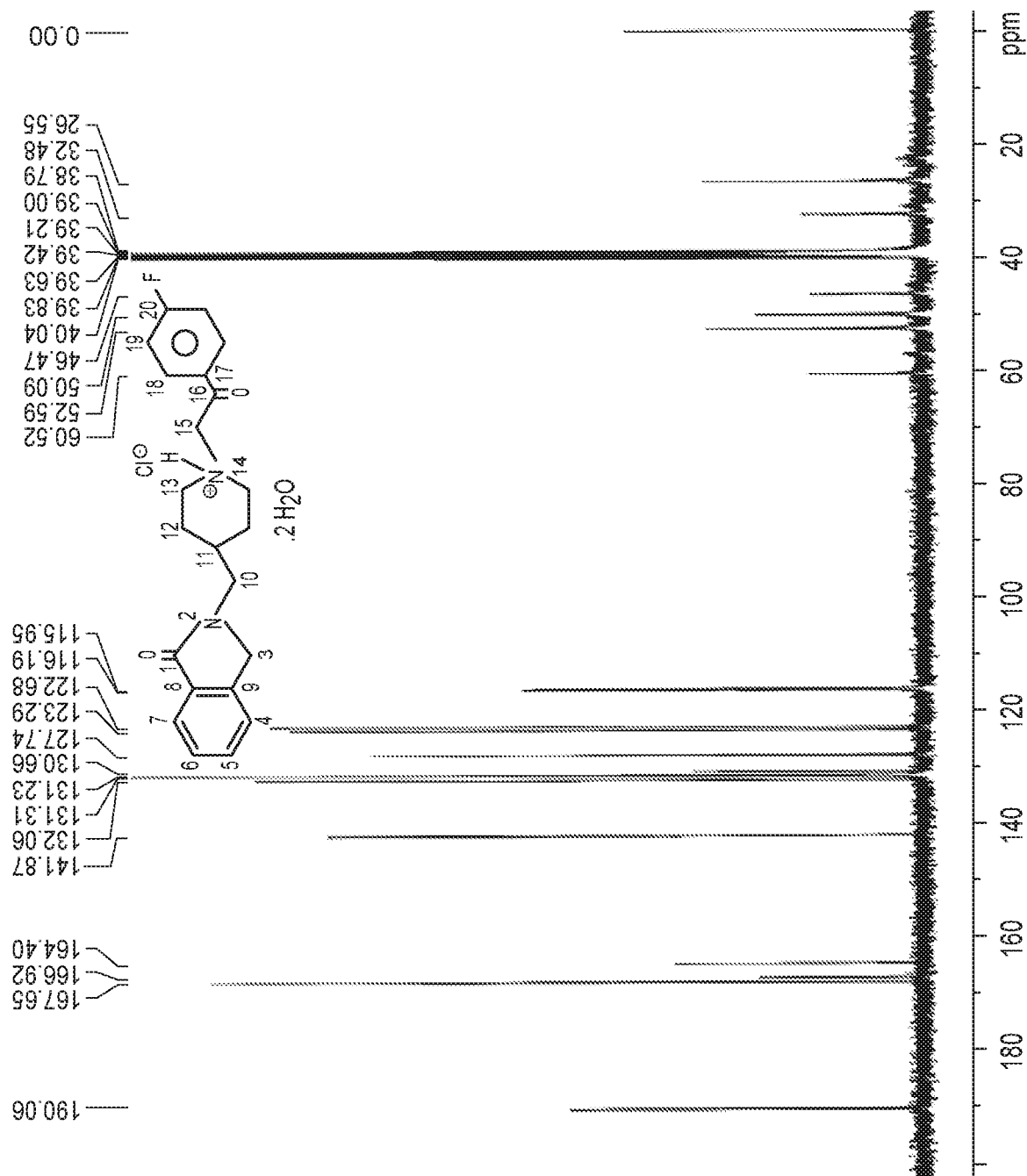
FIG. 17 is a $^{13}$C-NMR spectrum for batch C001 (from PCAS).
Figure 18:
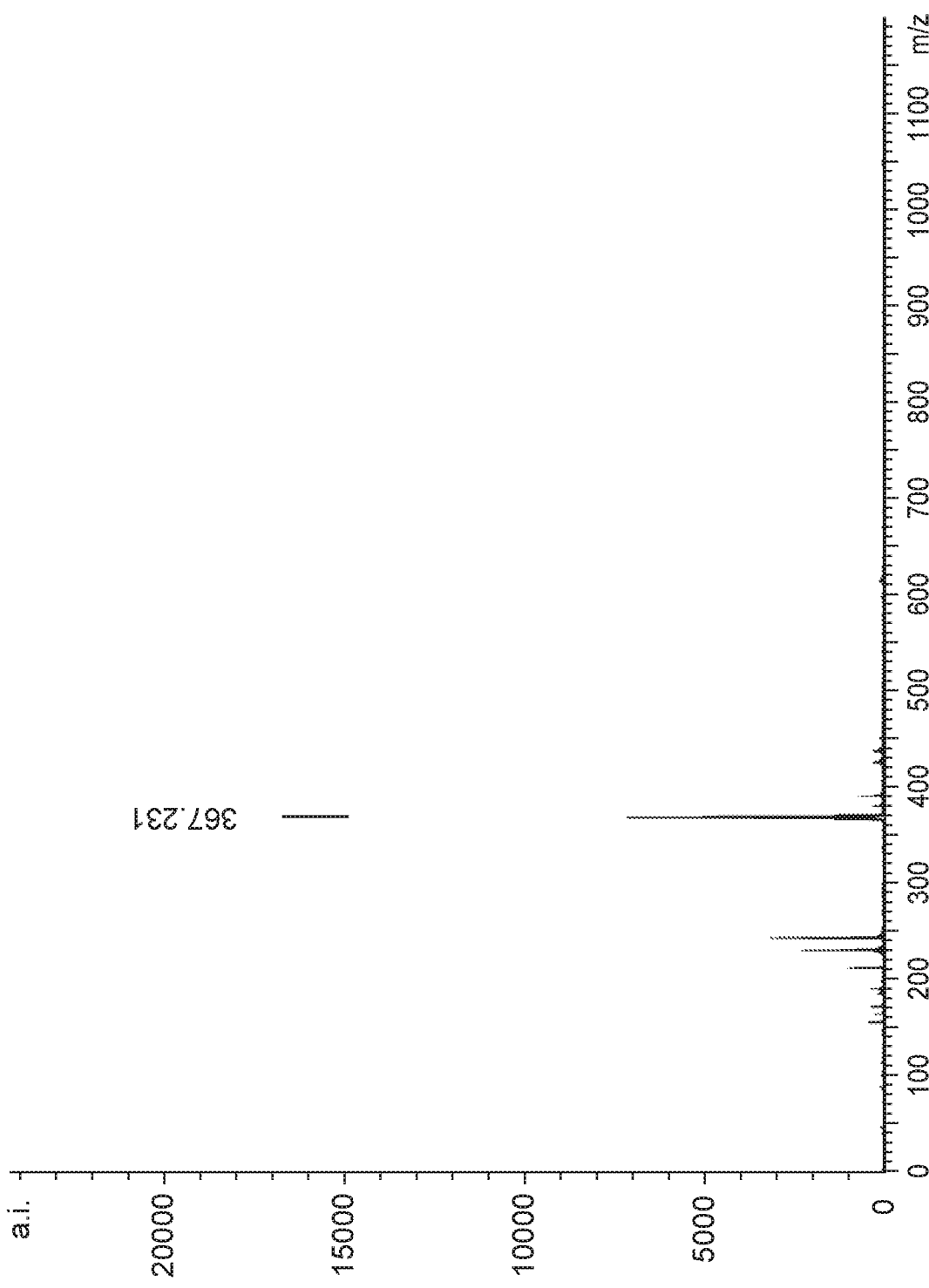
FIG. 18 is a mass spectrum of Form (A) of Compound (I).HCl.2H$_2$O by MALDI-TOF (from MTPC).
Figure 19:
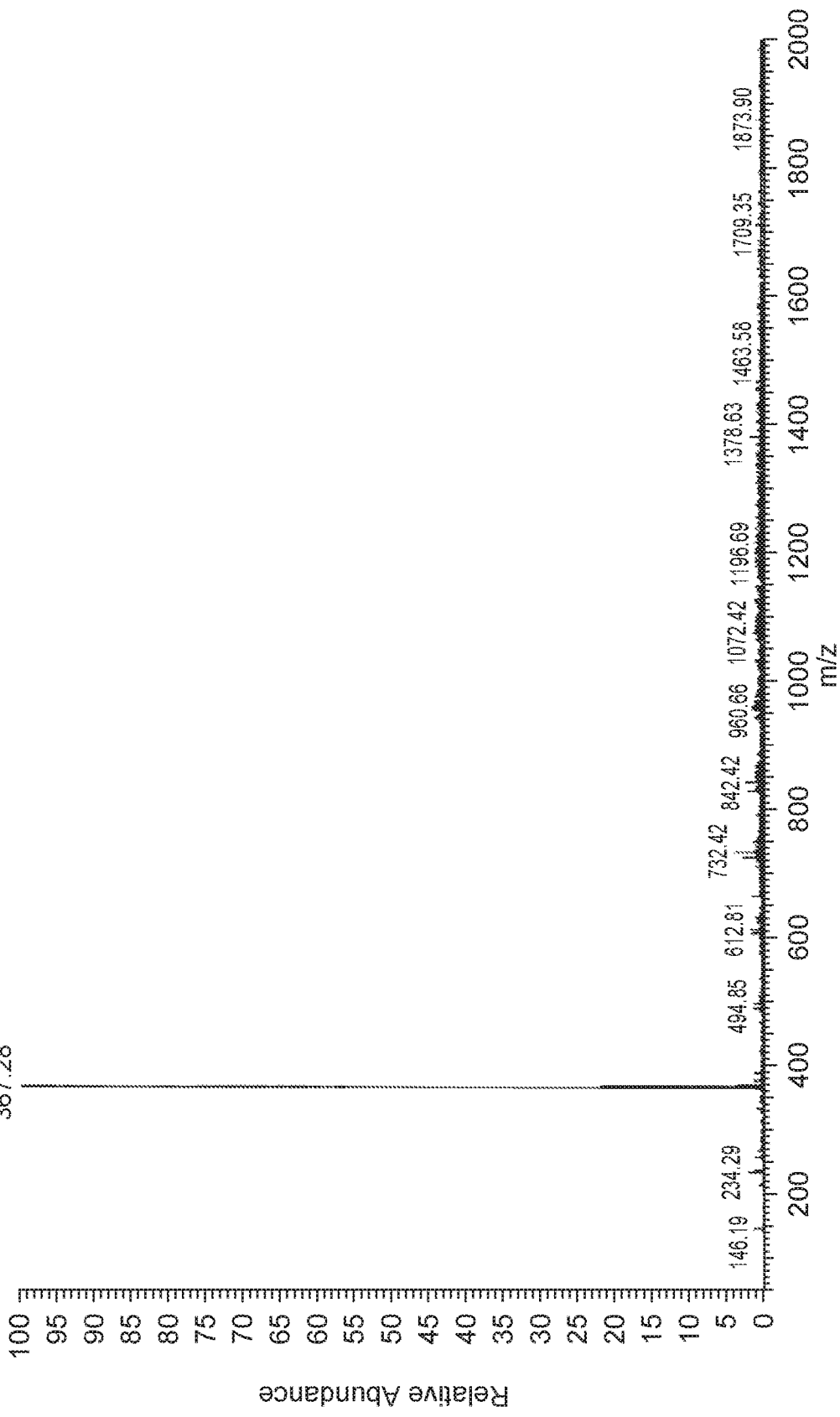
FIG. 19 is a mass spectrum of Form (A) of Compound (I).HCl.2H$_2$O by ESI ionization for bath C001 (from PCAS).

In one embodiment, Form (A) of Compound (I).HCl.2H$_2$O has a $^{13}$C NMR spectrum substantially similar to that shown in FIG. 14.

In one embodiment, Form (A) has $^{13}$C NMR spectrum peaks at 164.7, 166.7, 167.6, and 190.1 δ in d$_6$-dimethyl sulfoxide.

In one embodiment, Form (A) has $^{13}$C NMR spectrum peaks at 60.6, 164.7, 166.7, 167.6, and 190.1 δ in d$_6$-dimethyl sulfoxide.

In one embodiment, Form (A) has $^{13}$C NMR spectrum peaks at 50.2, 60.6, 164.7, 166.7, 167.6, and 190.1 δ in d$_6$-dimethyl sulfoxide.

In one embodiment, Form (A) has $^{13}$C NMR spectrum peaks at 46.5, 50.2, 60.6, 164.7, 166.7, 167.6, and 190.1 δ in d$_6$-dimethyl sulfoxide.

The application also pertains, at least in part, to a process for preparing a polymorph of Compound (I).HCl.2H$_2$O.

In one embodiment, the disclosure pertains to a process for making Form (A) of Compound (I).HCl.2H$_2$O.

In one embodiment, Form (A) of Compound (I).HCl.2H$_2$O is prepared by a process comprising: (1) reaction of the free base of Compound (I) with hydrochloric acid in acetone; and (2) heating of the crude Compound (I) in acetone and water, followed by cooling, filtration, and drying under reduced pressure.

The disclosure also pertains, at least in part, to a process for preparing a highly pure form of a polymorph of Compound (I).HCl.2H$_2$O. In one embodiment, the highly pure form of a polymorph of Compound (I).HCl.2H$_2$O is Form (A). In one embodiment, Form (A) has a purity of at least 90%. In one embodiment, Form (A) has a purity of at least 92%. In one embodiment, Form (A) has a purity of at least 94%. In one embodiment, Form (A) has a purity of at least 95%. In one embodiment, Form (A) has a purity of at least 96%. In one embodiment, Form (A) has a purity of at least 97%. In one embodiment, Form (A) has a purity of at least 98%. In one embodiment, Form (A) has a purity of at least 99%. In one embodiment, Form (A) has a purity of at least 99.5%. In one embodiment, Form (A) has a purity of at least 99.6%. In one embodiment, Form (A) has a purity of at least 99.7%. In one embodiment, Form (A) has a purity of at least 99.8%.

The disclosure also pertains, at least in part, to a process for preparing a polymorph form of Compound (I).HCl.2H$_2$O with minimal amounts of impurities. In one embodiment, the polymorph form of Compound (I).HCl.2H$_2$O with minimal amounts of impurities is Form (A). In one embodiment, the form of a polymorph of Compound (I).HCl.2H$_2$O with minimal amounts of impurities is Form (A), wherein the impurities are

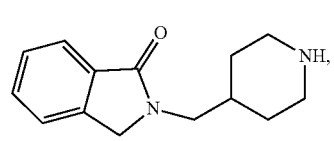

(V)

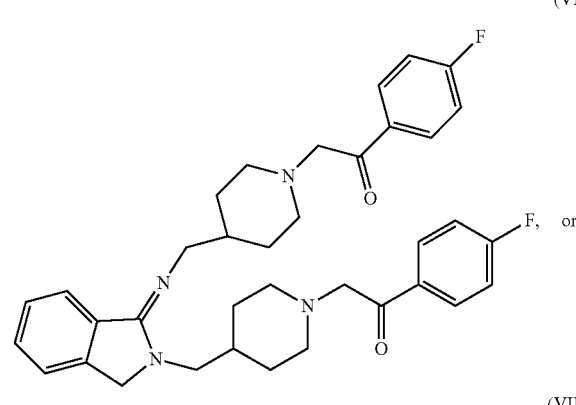

(VI)

F, or

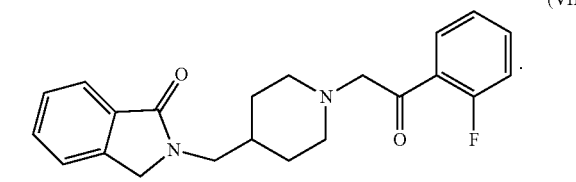

(VII)

In one embodiment, Form (A), contains less than 3% combined of impurities (V), (VI), and (VII). In one embodiment, Form (A), contains less than 2.5% combined of impurities (V), (VI), and (VII). In one embodiment, Form (A), contains less than 2% combined of impurities (V), (VI), and (VII). In one embodiment, Form (A), contains less than 1.5% combined of impurities (V), (VI), and (VII). In one embodiment, Form (A), contains less than 1% combined of impurities (V), (VI), and (VII). In one embodiment, Form (A), contains less than 0.5% combined of impurities (V), (VI), and (VII).

In another embodiment, Form (A) contains less than 0.5% of impurity (V). In another embodiment, Form (A) contains less than 0.2% of impurity (V). In another embodiment, Form (A) contains less than 0.1% of impurity (V).

In another embodiment, Form (A) contains less than 1% of impurity (VI). In another embodiment, Form (A) contains less than 0.5% of impurity (VI). In another embodiment, Form (A) contains less than 0.2% of impurity (VI). In another embodiment, Form (A) contains less than 0.1% of impurity (VI).

In another embodiment, Form (A) contains less than 1% of impurity (VII). In another embodiment, Form (A) contains less than 0.5% of impurity (VII). In another embodiment, Form (A) contains less than 0.2% of impurity (VII). In another embodiment, Form (A) contains less than 0.1% of impurity (VII).

The disclosure also pertains to pharmaceutical compositions comprising a polymorph of Compound (I).HCl.2H$_2$O and one or more pharmaceutically acceptable diluents, excipients, or carriers. In one embodiment, the pharmaceutical compositions comprise Form (A) of Compound (I).HCl.2H$_2$O and one or more pharmaceutically acceptable diluents, excipients, or carriers.

The disclosure also pertains to a method of treating a neuropsychiatric disease or disorder, comprising administering a therapeutically effective amount of a polymorph of Compound (I).HCl.2H$_2$O or a pharmaceutical composition thereof to a subject in need thereof.

In one embodiment, the disclosure also pertains to a method of treating a neuropsychiatric disease or disorder, comprising administering a therapeutically effective amount of Form (A) of Compound (I).HCl.2H$_2$O, or a pharmaceutical composition thereof, to a subject in need thereof.

In one embodiment, the neuropsychiatric disease is schizophrenia.

The term "polymorph" is synonymous with "crystalline polymorph", "crystal polymorph", "crystal form" and "polymorphic form." Each term refers to a crystal structure in which Compound (I).HCl.2H$_2$O crystallizes in a specific crystal packing arrangements, i.e., Form (A), which has the same elemental composition as Compound (I).HCl.2H$_2$O.

The differences in physical properties exhibited by polymorphs affect pharmaceutical parameters such as storage stability, compressibility and density (important in formulation and product manufacturing), and dissolution rates (an important factor in bioavailability). Differences in stability can also result from changes in chemical reactivity (e.g., differential oxidation, such that a dosage form discolors more rapidly when comprised of one polymorph than when comprised of another polymorph or amorphous form) or mechanical property (e.g., tablets crumble on storage as a kinetically favored polymorph or amorphous form converts to thermodynamically more stable polymorph or amorphous form) or both (e.g., tablets of one polymorph or amorphous form are more susceptible to breakdown at high humidity). In addition, the physical properties of the crystal may be important in processing, for example, a polymorph or amorphous form might be more likely to form solvates or might be difficult to filter and wash free of impurities (e.g., particle shape and size distribution might be different between a polymorph and an amorphous form).

A polymorph of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion, and sublimation.

Techniques for characterizing polymorphs include, but are not limited to, differential scanning calorimetry (DSC), X-ray powder diffractometry (XRPD), single crystal X-ray diffractometry, vibrational spectroscopy (e.g., IR and Raman spectroscopy), TGA, DTA, DVS, solid state NMR, hot stage optical microscopy, scanning electron microscopy (SEM), electron crystallography and quantitative analysis, particle size analysis (PSA), surface area analysis, solubility studies, and dissolution studies.

As used herein, the term "amorphous form" refers to a noncrystalline solid state form of a substance.

As used herein, a compound is "stable" where significant amounts of degradation products are not observed under constant conditions of humidity (e.g., 10%, 20%, 30%, 40%, 50%, 60%, 70%, 75%, 80%, 85%, 90%, and 95% relative humidity, light exposure and temperatures (e.g., higher than 0° C., e.g., 20° C., 25° C., 30° C., 35° C., 40° C., 45° C., 50° C., 55° C., 60° C., 65° C., and 70° C.) over a certain period (e.g., one week, two weeks, three weeks, and four weeks). A compound is not considered to be stable at a certain condition when degradation impurities appear or an area percentage (e.g., AUC as characterized by HPLC) of existing impurities begins to grow. The amount of degradation growth as a function of time is important in determining compound stability.

As used herein, the term "mixing" means combining, blending, stirring, shaking, swirling, or agitating. The term "stirring" means mixing, shaking, agitating, or swirling. The term "agitating" means mixing, shaking, stirring, or swirling.

Unless explicitly indicated otherwise, the terms "approximately" and "about" are synonymous. In one embodiment, "approximately" and "about" refer to recited amount, value, or duration ±20%, ±15%, ±10%, ±8%, ±6%, ±5%, ±4%, ±2%, ±1%, or ±0.5%. In another embodiment, "approximately" and "about" refer to listed amount, value, or duration ±10%, ±8%, ±6%, ±5%, ±4%, or ±2%. In yet another embodiment, "approximately" and "about" refer to listed amount, value, or duration ±5%.

When the terms "approximately" and "about" are used when reciting XRPD peaks, these terms refer to the recited X-ray powder diffraction peak ±0.5° 2θ, ±0.4° 2θ±0.3° 2θ, ±0.2° 2θ, or ±0.1° 2θ. In another embodiment, the terms "approximately" and "about" refer to the listed X-ray powder diffraction peak ±0.2° 2θ. In another embodiment, the terms "approximately" and "about" refer to the listed X-ray powder diffraction peak ±0.1° 2θ.

When the terms "approximately" and "about" are used when reciting temperature or temperature range, these terms refer to the recited temperature or temperature range ±5° C., ±2° C., or ±1° C. In another embodiment, the terms "approximately" and "about" refer to the recited temperature or temperature range ±2° C.

Compound (I)

The disclosure provides pharmaceutical formulations of Compound (I):

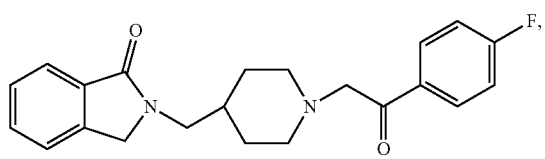 [SMILES: O=C(CN1CCC(CN2Cc3ccccc3C2=O)CC1)c1ccc(F)cc1]

or a pharmaceutically acceptable salt thereof.

In one embodiment, the formulations of the disclosure provide maximum plasma concentration ($C_{max}$) and area under the curve (AUC) of Compound (I) and its two active metabolites (BFB-520 and BFB-999) at levels associated with improved therapeutic response and fewer adverse reactions (e.g., prolongation of QT intervals).

In one embodiment, the formulations of the disclosure increase the maximum plasma concentration ($C_{max}$) and area under the curve (AUC) of BFB-999 and at the same time reduce the maximum plasma concentration ($C_{max}$) and area under the curve (AUC) of BFB-520.

In one embodiment, the formulations of the disclosure provide a maximum plasma concentration ($C_{max}$) of Compound (I) below 50 ng/mL, below 45 ng/mL, below 40 ng/mL, below 35 ng/mL, below 30 ng/mL, below 25 ng/mL, below 20 ng/mL, below 15 ng/mL, or below 10 ng/mL. In one embodiment, the formulations of the disclosure provide an AUC of Compound (I) below 400 hr*ng/mL, below 350 hr*ng/mL, below 300 hr*ng/mL, below 250 hr*ng/mL, below 200 hr*ng/mL, below 150 hr*ng/mL, or below 100 hr*ng/mL.

In one embodiment, the formulations of the disclosure provide a maximum plasma concentration ($C_{max}$) of BFB-520 below 5.0 ng/mL, below 4.5 ng/mL, below 4.0 ng/mL, below 3.5 ng/mL, below 3.0 ng/mL, below 2.5 ng/mL, below 2.0 ng/mL, below 1.5 ng/mL, or below 1.0 ng/mL. In one embodiment, the formulations of the disclosure provide an AUC of BFB-520 below 40 hr*ng/mL, below 35 hr*ng/mL, below 30 hr*ng/mL, below 25 hr*ng/mL, below 20 hr*ng/mL, below 15 hr*ng/mL, or below 10 hr*ng/mL. In one embodiment, BFB-520 is associated with prolongation of QT intervals at supra-therapeutic levels.

In one embodiment, to avoid QT prolongation, maximum plasma concentration ($C_{max}$) of Compound (I) and BFB-520 should not exceed 80 ng/mL and 12 ng/mL respectively. In one embodiment, the formulations of the disclosure provide a $C_{max}$ of BFB-520 below 10 ng/mL, below 9.0 ng/mL, below 8.0 ng/mL, below 7.0 ng/mL, below 6.0 ng/mL, 5.0 ng/mL, below 4.5 ng/mL, below 4.0 ng/mL, below 3.5 ng/mL, below 3.0 ng/mL, below 2.5 ng/mL, below 2.0 ng/mL, below 1.5 ng/mL, or below 1.0 ng/mL. In one embodiment, the formulations of the disclosure provide a $C_{max}$ of BFB-999 below 5.0 ng/mL, below 4.5 ng/mL, below 4.0 ng/mL, below 3.5 ng/mL, below 3.0 ng/mL, below 2.5 ng/mL, below 2.0 ng/mL, below 1.5 ng/mL, or below 1.0 ng/mL. In one embodiment, the formulations of the disclosure provide an AUC of BFB-999 below 40 hr*ng/mL, below 35 hr*ng/mL, below 30 hr*ng/mL, below 25 hr*ng/mL, below 20 hr*ng/mL, below 15 hr*ng/mL, or below 10 hr*ng/mL.

In one embodiment, the formulations of the disclosure comprise about 1-100 mg of Compound (I), about 1-75 mg of Compound (I), about 2-75 mg of Compound (I), about 5-75 mg of Compound (I), about 10-75 mg of Compound (I), about 15-75 mg of Compound (I), about 15-70 mg of Compound (I), about 15-65 mg of Compound (I). In one embodiment, the formulations of the disclosure comprise about 16 mg of Compound (I), about 32 mg of Compound (I), about 40 mg of Compound (I), or about 64 mg of Compound (I).

In one embodiment, the formulations of the disclosure are suitable for chronic administration (e.g., one week, two weeks, three weeks, four weeks, two months, four months, six months, eight months, ten months, one year, two years, three years, four years, and five years).

In one embodiment, the formulations of the disclosure are administered once daily.

In one embodiment, the formulations of the disclosure are administered to a subject under a fast condition. In one embodiment, the formulations of the disclosure are administered to a subject at least 4 hours after the subject has taken a meal, at least 6 hours after the subject has taken a meal, at least 8 hours after the subject has taken a meal, at least 10 hours after the subject has taken a meal, at least 12 hours after the subject has taken a meal. In one embodiment, the formulations of the disclosure are administered to a subject under a fed condition. In one embodiment, the formulations of the disclosure are administered to a subject within 4 hour after the subject has taken a meal, within 3 hours after the subject has taken a meal, within 2 hours after the subject has taken a meal, within 1 hour after the subject has taken a meal, or within 0.5 hour after the subject has taken a meal.

By "a meal" it means any amount of food, which includes any sources of carbohydrate, protein, amino acid, etc.

In one embodiment, the formulations of the disclosure are suitable for oral administration, intravenous administration, intramuscular administration, or subcutaneous administration. In one embodiment, the formulations of the disclosure are suitable for oral administration. In one embodiment, the formulations of the disclosure are in the form of a tablet or capsule.

In one embodiment, the tablet formulation comprises Compound (I), a release modifier, a filler, a glidant, and a lubricant. In one embodiment, the release modifier is hypromellose (e.g., hypromellose K100LV CR, hypromellose K4M CR, hypromellose E50, or a combination thereof). In one embodiment, the filler is microcrystalline cellulose, lactose, or a combination thereof. In one embodiment, the glidant is silica colloidal anhydrous. In one embodiment, the lubricant is magnesium stearate, Kolliwax HCO, sodium stearyl fumarate, or a combination thereof.

In a further embodiment, the tablet formulation may further comprise a binder, such as hydroxypropylcellulose. In a further embodiment, the tablet formulation may further comprise a disintegrant, such as crospovidone. In a further embodiment, the tablet formulation may further comprise an anti-adherent, such as talc. In a further embodiment, the tablet formulation may further comprise a pH adjuster, such as an organic or inorganic acid or an organic or inorganic base. In a further embodiment, the tablet formulation may further comprise sweeting agent, such a sugar (e.g., mannitol).

In one embodiment, the release profile of the tablet formulation is controlled by varying the amount of the release modifier in the formulation. In one embodiment, the release rate of Compound (I) from the tablet formulation is decreased by increasing the amount of the release modifier.

In one embodiment, the formulations of the disclosure are in an immediate release form. In one embodiment, the formulations of the disclosure are in a modified release form. In one embodiment, the modified release formulations are in a slow-(release rate of 16-24 hours), medium-(release rate of 10-12 hours) or fast-(release rate of 5-7 hours) release form.

In one embodiment, the formulations of the disclosure are in a controlled release form.

In one embodiment, the formulations of the disclosure are in a sustained release form (e.g., the release takes place for at least 4 hours, 6 hours, 8 hours, 10 hours, 12 hours, 18 hours, or 24 hours). In one embodiment, the formulations of the disclosure are in the form of a slow sustained release form.

The disclosure also relates to methods for treating neuropsychiatric diseases and disorders, in particular, schizophrenia, comprising administering a therapeutically effective amount of a formulation of the invention to a subject in need thereof.

In one embodiment, a method for treating or diminishing at least one symptom of neuropsychiatric diseases and disorders, in particular, schizophrenia, is provided, comprising administering a therapeutically effective amount of a formulation of the invention to a subject in need thereof.

In one embodiment, a method for treating or diminishing at least one symptom of schizophrenia is provided, comprising administering a therapeutically effective amount of a formulation of the invention to a subject in need thereof.

In one embodiment, a method for treating or diminishing at least one symptom of schizophrenia is provided, comprising administering a formulation of the invention to a subject in need thereof, wherein the amount of Compound (I) is in the range of about 1-100 mg, about 1-75 mg, about 2-75 mg, about 5-75 mg, about 10-75 mg, about 15-75, about 15-70 mg, or about 15-65 mg.

In one embodiment, a method for treating or diminishing at least one symptom of schizophrenia is provided, comprising administering a formulation of the invention to a subject in need thereof, wherein the amount of Compound (I) is about 16 mg, about 32 mg, about 40 mg, or about 64 mg.

In one embodiment, the formulations of the disclosure are administered for treating or diminishing at least one symptom of schizophrenia associated with the negative and/or positive symptoms of schizophrenia, cognitive function, sleep architecture and continuity, and social functioning.

In another embodiment, the formulations of the disclosure are administered for improving depressive symptoms.

In one embodiment, a method for treating or diminishing at least one condition or disorder associated with depression is provided, comprising administering a formulation of the invention to a subject in need thereof.

In another embodiment, a method for improving sleep, such as sleep architecture and continuity, is provided, comprising administering a formulation of the invention to a subject in need thereof.

In one embodiment, a method for treating or diminishing at least one aspect of a sleep disorder in a subject afflicted with neuropsychiatric diseases and disorders, in particular, schizophrenia, is provided, comprising administering a formulation of the invention to the subject. In one embodiment, at least one aspect of a sleep disorder is treated. In another embodiment, at least one aspect of a sleep disorder is improved. In an aspect, the disruption of at least one aspect of sleep is associated with schizophrenia.

Various aspects of sleep may be treated, including, but not limited to, sleep onset latency, latency to persistent sleep, distribution of slow wave sleep across the sleep period time, or one or more segments of sleep period time, overall sleep continuity and sleep architecture.

Cognitive impairment is the diminished ability to think, concentrate, formulate ideas, reason and remember. In one embodiment, a method for treating or diminishing cognitive impairment or improving cognition is provided, comprising administering a formulation of the invention to a subject in need thereof. In one embodiment, a method is provided for treating schizophrenia without provoking cognitive impairment.

In one embodiment, a method is provided for treating schizophrenia and restoring, enhancing, and improving cognition, in a subject following discontinuation of treatment with another active pharmaceutical ingredient, for example, an anti-depressant compound.

In one embodiment, a method is provided for treating schizophrenia in combination with a cognition impairing active pharmaceutical ingredient (for example, a cognition impairing anti-depressant compound), without causing or increasing cognitive impairment, or for improving, enhancing or restoring cognition in a subject.

In another embodiment, cognitive impairment present in a subject suffering from schizophrenia is treated or diminished by the administration of a formulation of the invention to the subject. As will be understood based on the disclosure herein, modification of sleep parameters can improve cognition. By way of a non-limiting example, improvement and/or an increase in slow wave sleep (SWS) improves cognition. In an aspect, cognition in general is improved. In another aspect, one or more aspects of cognition are improved, including, among others, memory consolidation, executive functions, verbal memory, and verbal fluency. In one embodiment, cognition is improved in a subject to the point where normal cognition is restored in the subject. In another embodiment, cognition is improved in a subject beyond the point of normal cognition in the subject, such that levels of cognition in the subject are enhanced.

In one embodiment, cognition is improved in a subject afflicted with schizophrenia.

The active ingredient is Compound (I) (also known as CYR-101 and MT-210). U.S. Pat. No. 7,166,617, incorporated herein by reference in its entirety, discloses cyclic amide derivatives including Compound (I), 2-{1-[2-(4-Fuorophenyl)-2-oxoethyl] piperidin-4-ylmethyl}-2,3-dihydroisoindol-1-one monohydrochloride dihydrate. The derivatives disclosed in U.S. Pat. No. 7,166,617 were found to have high affinity for the sigma ligand binding site and low inhibition constant Ki for sigma 1 and/or sigma 2. It was also found that these compounds had a selective binding profile completely different from those of conventional known compounds, and were useful for treatment of diseases that can be therapeutically and/or preventively treated by the nerve control function of the sigma ligands.

The formulations of Compound (I) as described herein represent an important milestone in an effort to develop customized formulations of neuropsychiatric therapies based on optimal efficacy, safety, tolerability and pharmacokinetic profiles. The formulations as described herein are able to target significant areas of unmet need in the treatment of negative symptoms, cognitive impairments and sleep disorders while offering a highly favorable safety profile.

The formulations of the disclosure are able to maintain plasma levels of Compound (I) over the course of one day while reducing BFB-520 levels and increasing levels of BFB-999 associated with sleep improvements due to its affinity to 5-HT2A and histaminergic H1 receptors. It is shown that the formulations of the disclosure lower levels of BFB-520, which is associated with prolongation of QT intervals at supra-therapeutic levels.

The QT interval represents the duration of ventricular depolarization and subsequent repolarization, and is measured from the beginning of the QRS complex to the end of the T wave. A delay in cardiac repolarization creates an electrophysiological environment that favors the development of cardiac arrhythmias, most clearly torsade de pointes (TdP), but possibly other ventricular tachyarrhythmias as well. TdP is a polymorphic ventricular tachyarrhythmia that appears on the ECG as continuous twisting of the vector of the QRS complex around the isoelectric baseline. A feature of TdP is pronounced prolongation of the QT interval in the supraventricular beat preceding the arrhythmia. TdP can degenerate into ventricular fibrillation, leading to sudden death. According to ICH-E14 on Clinical Evaluation of QT/QTc Interval Prolongation and Proarrhythmic Potential for Non-Antiarrhythmic Drugs, discontinuation of a subject from a clinical trial should be considered if there is a marked prolongation of the QT/QTc interval during treatment with the study drug, especially if the measurement is obtained from more than one ECG.

The disclosure provides an optimal formulation which reduces the risk of QT/QTc prolongation and achieves a once a day dosing strategy to facilitate patient compliance.

Definitions

In other embodiments, as set forth in greater detail elsewhere herein, the dosage and dosing regimen for Compound (I) and/or Form A of Compound (I) may be optimized based on the health and condition of the subject to be treated, as well as the desired outcome of the treatment.

The term "receptor", as used herein, means a molecule, with which one or more kinds of signaling molecules can specifically interact. For example, the 5-HT1A receptor is a subtype of the 5-HT receptor, which binds the neurotransmitter serotonin ("5-hydroxytryptamine").

The term "subject" refers to any animal, including mammals, such as, but not limited to, humans, mice, rats, other rodents, rabbits, dogs, cats, pigs, cattle, sheep, horses, or primates.

The term "treating" (and corresponding terms "treat" and "treatment") includes palliative, restorative, and preventative ("prophylactic") treating of a subject. The term "palliative treating" refers to treatment that eases or reduces the effect or intensity of a condition in a subject without curing the condition. The term "preventative treating" (and the corresponding term "prophylactic treating") refers to treatment that prevents the occurrence of a condition in a subject. The term "restorative treating" ("curative") refers to treatment that halts the progression of, reduces the pathologic manifestations of, or entirely eliminates a condition in a subject. Treating can be done with a therapeutically effective amount of compound, salt or composition that elicits the biological or medicinal response of a tissue, system or subject that is being sought by an individual such as a researcher, doctor, veterinarian, or clinician. The term "treatment" will also be understood to include not only a complete remission of all symptoms experienced by the treated individual, but also the alleviation of one or more existing symptoms, as well as the prevention of occurrence of symptoms by preemptive administration of a compound of formula I to an individual prone to or likely to develop any of the symptoms, such as those with chronic or recurrent neuropsychiatric disease or disorder.

The term "modified release" as used herein can be understood as the escape of the drug from the tablet has been modified in some way. Usually this is to slow the release of the drug so that the medicine does not have to be taken too often and therefore improves compliance. The other benefit from modifying release is that the drug release is controlled and there are smaller peaks and troughs in blood levels therefore reducing the chance of peak effects and increasing the likelihood of therapeutic effectiveness for longer periods of time.

The pattern of drug release from modified-release (MR) dosage forms is deliberately changed from that of a conventional (immediate-release) dosage formulation to achieve a desired therapeutic objective or better patient compliance. Types of MR drug products may include delayed release (e.g., enteric coated), extended release (ER), and orally disintegrating tablets (ODT).

The term modified-release formulation can be used to describe formulation that alters the timing and/or the rate of release of the drug substance. A modified-release dosage form is a formulation in which the drug-release characteristics of time course and/or location are chosen to accomplish therapeutic or convenience objectives not offered by conventional dosage forms such as solutions, ointments, or promptly dissolving dosage forms. Several types of modified-release oral drug products are recognized including:

An extended-release formulation refers to a formulation that allows at least a two-fold reduction in dosage frequency as compared to an immediate-release (conventional) dosage form. Examples of extended-release dosage forms include controlled-release, sustained-release, and long-acting drug products.

A delayed-release formulation refers to a formulation that releases a discrete portion or portions of drug at a time other than promptly after administration. An initial portion may be released promptly after administration. Enteric-coated dosage forms are common delayed-release products (e.g., enteric-coated aspirin and other NSAID products).

The term "compounds of the disclosure" of "compound of the disclosure" refers to Compound (I), Form A of Compound (I) or a pharmaceutically acceptable salt thereof as described herein.

The term "pharmaceutically acceptable", as used herein with respect to a compound or composition, refers to a form of the compound or composition that can increase or enhance the solubility or availability of the compound in a subject, in order to promote or enhance the bioavailability of the compound or composition.

The term "pharmaceutically acceptable salt" is to describe a salt form of one or more of the compositions herein which are presented to increase the solubility of the compound, for example, in the gastric juices of the patient's gastrointestinal tract in order to promote dissolution and the bioavailability of the compounds and/or compositions. In an embodiment, pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts are particularly preferred as neutralization salts of carboxylic acids and free acid phosphate containing compositions encompassed by the present disclosure. The term "salt" shall mean any salt consistent with the use of the compounds encompassed by the present disclosure. In the case where the compounds are used in pharmaceutical indications, including the treatment of depression, the term "salt" shall mean a pharmaceutically acceptable salt, consistent with the use of the compounds as pharmaceutical agents.

As used herein, the term pharmaceutically acceptable salts refer to salts that retain the desired biological activity of the parent compound and exhibit minimal, if any, undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acids, naphthalenedisulfonic acids, and polygalacturonic acid; (b) base addition salts formed with polyvalent metal cations such as zinc, calcium, bismuth, barium, magnesium, aluminum, copper, cobalt, nickel, cadmium, sodium, potassium, and the like, or with an organic cation formed from N,N-dibenzylethylene-diamine, ammonium, or ethylenediamine; or (c) combinations of (a) and (b); e.g., a zinc tannate salt or the like.

In an embodiment, compositions comprise base addition salts of the present compound. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine (meglumine), and the lower alkanolammonium and other base salts of pharmaceutically acceptable organic amines, among others.

A "composition" or "pharmaceutically acceptable composition" is a formulation containing a compound of the invention or salt, solvate, ester, or amino acid conjugate thereof. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of a compound of the invention or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, ocular, ophthalmic, pulmonary, rectal, parenteral, transdermal, subcutaneous, intravenous, intramuscular, intraperitoneal, intranasal, and the like. Dosage forms for the topical or transdermal administration of a compound of this invention include powders, sprays, ointments, pastes, creams, lotions, gels, solutions, patches and inhalants. In another embodiment, the active compound is mixed under sterile conditions with a pharmaceutically acceptable carrier, and with any preservatives, buffers, or propellants that are required.

In certain embodiments, the pharmaceutical formulations or compositions of the present invention may additionally contain other adjunct components conventionally found in pharmaceutical compositions, at their art-established usage levels. Thus, for example, the compositions may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

In certain embodiments, pharmaceutical compositions of the present invention comprise one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition of the present invention is prepared using known techniques, including, but not limited to mixing, dissolving, granulating, dragee-making, levigating, emulsifying, encapsulating, entrapping or tableting processes.

Modifications of a compound can affect the solubility, bioavailability and rate of metabolism of the active species, thus providing control over the delivery of the active species. Further, the modifications can affect the desired activity of the compound, in some cases increasing the activity over the parent compound. This can easily be assessed by preparing the derivative and testing its antidepressant activity according to the methods encompassed herein, or other methods known to those skilled in the art.

Compositions encompassed herein may be administered orally. In other embodiments, compositions may be administered parenterally, by inhalation spray, topically, rectally, nasally, buccally, vaginally or via an implanted reservoir. The term "parenteral" as used herein includes subcutaneous, percutaneous, intravenous, intramuscular, intra-articular, intra-synovial, intrasternal, intrathecal, intrahepatic, intralesional and intracranial injection or infusion techniques. As will be understood by the skilled artisan, in view of the embodiments encompassed herein, the means of administration and the dosage of active ingredient or ingredients (e.g., a compound of formula I) may be adjusted upward or downward based on the selected route of administration. Furthermore, it will be understood that optimizing the dosage of active ingredient for any selected dosage form may be desired and can be achieved by using the methods described herein or known in the art to evaluate the effectiveness of antipsychotic compounds.

The pharmaceutical compositions embodied herein may be orally administered in any orally acceptable dosage form including, but not limited to, capsules, tablets, aqueous suspensions or solutions. In the case of tablets for oral use, carriers which are commonly used include lactose and corn starch. In an embodiment, lubricating agents, such as magnesium stearate, are also added. For oral administration in a capsule form, useful diluents include lactose and/or dried corn starch, as two non-limiting examples. When aqueous suspensions are required for oral use, the active ingredient is combined with emulsifying and suspending agents. If desired, certain sweetening, flavoring or coloring agents may also be added.

In one embodiment, formulations of the present invention may be administered in conjunction with one or more other medications. Such other medications may be administered or co-administered in forms and dosages as known in the art.

The term "co-administration" or "combination therapy" is used to describe a therapy in which at least two compounds are used to treat schizophrenia or another neuropsychiatric disease or condition as described herein at the same time. In an embodiment, at least two compounds in effective amounts are used to treat schizophrenia or another neuropsychiatric disease or condition at the same time. In another embodiment, at least two compounds, the combination of which comprises an effective amount, are used to treat schizophrenia or another neuropsychiatric disease or condition as described herein at the same time. In an embodiment, the result of treatment with the at least two compounds may be additive of the treatment results obtained using each compound separately, either directly additive, or additive to a degree lesser than the results obtained with the two compounds separately. In an embodiment, the result of treatment with the at least two compounds may be synergistic, to varying degrees. In an embodiment, the result of treatment with the at least two compounds may be less than the treatment results obtained using each compound separately. In an aspect, the result of treatment with a composition encompassed herein is such that, for one compound, the result of treatment is less than that obtained with the compound separately, while the results of treatment with respect to the other compounds in the composition are about the same as the results of treatment obtained separately.

Although the term co-administration encompasses the administration of two active compounds to the patient at the same time, it is not necessary that the compounds be administered to the patient at the same time, although effective amounts of the individual compounds will be present in the patient at the same time.

In an embodiment, a compound set forth herein can be co-administered with one or more atypical antipsychotics. Examples of atypical antipsychotics include, but are not limited to fluphenazine, risperidone, olanzapine, clozapine, quetiapine, ziprasidone, aripiprazole, seritindole, zotepine, and perospirone. Examples of antidepressants useful in combination therapy as encompassed herein include, but are not limited to, fluoxetine, citalopram, escitalopram, venlafaxine, duloxetine, bupropion.

Synthesis of Compound (I)

Standard synthetic methods and procedures for the preparation of organic molecules and functional group transformations and manipulations, including the use of protective groups, can be obtained from the relevant scientific literature or from standard reference textbooks in the field. Although not limited to any one or several sources, recognized reference textbooks of organic synthesis include: Smith, M. B.; March, J. March's Advanced Organic Chemistry: Reactions, Mechanisms, and Structure, $5^{th}$ ed.; John Wiley & Sons: New York, 2001; and Greene, T. W.; Wuts, P. G. M. Protective Groups in Organic Synthesis, $3^{rd}$; John Wiley & Sons: New York, 1999.

A method for preparing Compound (I) is described in U.S. Pat. No. 7,166,617, the entire contents of which is incorporated herein by reference.

Pharmaceutical Compositions of Form (A) of Compound (I).HCl.2H$_2$O

The disclosure also provides pharmaceutical compositions comprising form (A) of Compound (I).HCl.2H$_2$O and one or more pharmaceutically acceptable diluents, excipients, or carriers.

A "pharmaceutical composition" is a formulation containing form (A) of Compound (I).HCl.2H$_2$O in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of form (A) of Compound (I).HCl.2H$_2$O) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of form (A) of Compound (I).HCl.2H$_2$O include powders, sprays, ointments, pastes, creams, lotions, gels, solutions, patches and inhalants. In one embodiment, form (A) of Compound (I).HCl.2H$_2$O is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In an aspect, the disease or disorder to be treated is a neuropsychiatric disease or disorder. In another aspect, the disease or condition to be treated is schizophrenia.

For any compound, the therapeutically effective amount can be estimated initially either in cell culture assays or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active ingredient or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing form (A) of Compound (I).HCl.2H$_2$O may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active ingredient into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating form (A) of Compound (I).HCl.2H$_2$O in the required amount in an appropriate solvent with one or a combination of ingredients enumerated above, as required, followed by filtered sterilization. Generally, dispersions are prepared by incorporating form (A) of Compound (I).HCl.2H$_2$O into a sterile vehicle that contains a basic dispersion medium and the required other ingredients from those enumerated above. In the case of sterile powders for the preparation of sterile injectable solutions, methods of preparation are vacuum drying and freeze-drying that yields a powder of form (A) of Compound (I).HCl.2H$_2$O plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, form (A) of Compound (I).HCl.2H$_2$O can be incorporated with excipients and used in the form of tablets, troches, or capsules. Oral compositions can also be prepared using a fluid carrier for use as a mouthwash, wherein form (A) of Compound (I).HCl.2H$_2$O in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, form (A) of Compound (I).HCl.2H$_2$O is delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, form (A) of Compound (I).HCl.2H$_2$O is formulated into ointments, salves, gels, or creams as generally known in the art.

Form (A) of Compound (I).HCl.2H$_2$O can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811 (the contents of which are incorporated herein in their entirety).

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active ingredient calculated to produce the desired therapeutic effect in association with the required pharmaceutical carrier. The specification for the dosage unit forms of the disclosure are dictated by and directly dependent on the unique characteristics of form (A) of Compound (I).HCl.2H$_2$O and the particular therapeutic effect to be achieved.

In therapeutic applications, the dosages of the pharmaceutical compositions used in accordance with the application vary depending on the agent, the age, weight, and clinical condition of the recipient patient, and the experience and judgment of the clinician or practitioner administering the therapy, among other factors affecting the selected dosage. Dosages can range from about 0.01 mg/kg per day to about 5000 mg/kg per day. In an aspect, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). In other aspects, dosages can range from about 16 mg of Compound (I) per day to about 64 mg of Compound (I) per day administered in a single dose. In another aspect, dosages can range from about 30 mg of Compound (I) per day to about 50 mg of Compound (I) per day administered in a single dose. In an aspect, the dosage of Compound (I) in the pharmaceutical composition is 30 mg per day, 31 mg per day, 32 mg per day, 33 mg per day, 34 mg per day, 35 mg per day, 36 mg per day, 37 mg per day, 38 mg per day, 39 mg per day, 40 mg per day, 41 mg per day, 42 mg per day, 43 mg per day, 44 mg per day, 45 mg per day, 46 mg per day, 47 mg per day, 48 mg per day, 49 mg per day, and 50 mg per day administered in a single dose. In one embodiment, the dosage of Compound (I) in the pharmaceutical composition is 40 mg per day administered as a single dose.

An effective amount of a pharmaceutical agent is that which provides an objectively identifiable improvement as noted by the clinician or other qualified observer. As used herein, the term "dosage effective manner" refers to amount of form (A) of Compound (I).$HCl.2H_2O$ to produce the desired effect in a subject.

The pharmaceutical compositions can be included in a container, pack, or dispenser together with instructions for administration.

The pharmaceutical composition of the disclosure, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, form (A) of Compound (I).$HCl.2H_2O$ is administered orally. One skilled in the art will recognize the advantages of certain routes of administration.

The dosage regimen utilizing form (A) of Compound (I).$HCl.2H_2O$ is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the application can be found in Remington: the Science and Practice of Pharmacy, $19^{th}$ edition, Mack Publishing Co., Easton, Pa. (1995). In an embodiment, form (A) of Compound (I).$HCl.2H_2O$ is used in pharmaceutical preparations in combination with a pharmaceutically acceptable carrier or diluent. Suitable pharmaceutically acceptable carriers include inert solid fillers or diluents and sterile aqueous or organic solutions. Form (A) of Compound (I).$HCl.2H_2O$ will be present in such pharmaceutical compositions in amounts sufficient to provide the desired dosage amount in the range described herein.

All percentages and ratios used herein, unless otherwise indicated, are by weight.

Methods of Treatment

The disclosure also provides methods of treating a neuropsychiatric disease or disorder in a subject in need thereof by administering to a subject in need of such treatment, a therapeutically effective amount of form (A) of Compound (I).$HCl.2H_2O$, or a pharmaceutical composition thereof. The neuropsychiatric disease or disorder can be schizophrenia.

The term "subject" refers to any animal, including mammals, such as, but not limited to, humans, mice, rats, other rodents, rabbits, dogs, cats, pigs, cattle, sheep, horses, or primates. Subjects may or may not have been diagnosed with Schizophrenia. Subjects may present one or more signs or symptoms of schizophrenia.

In certain embodiments, subjects of the disclosure may have been treated for schizophrenia with one or more typical or atypical anti-psychotic therapies prior to, in combination with, or following treatment with a pharmaceutical composition comprising form (A) of Compound (I). In certain embodiments, subjects of the disclosure may have been treated for schizophrenia with one or more typical or atypical anti-psychotic therapies prior to treatment with a pharmaceutical composition comprising form (A) of Compound (I) and the one or more typical or atypical anti-psychotic therapies may have been ineffective to treat a sign or symptom of schizophrenia in the subject.

Other features and advantages of the disclosure are apparent from the different examples. The provided examples illustrate different components and methodology useful in practicing the disclosure.

The examples do not limit the claimed compositions, methods, and kits of the disclosure. Based on the present disclosure the skilled artisan can identify and employ other components and methodology useful for practicing the disclosure.

EXAMPLES

Example 1

Increases in QTc interval were observed and seemed to be related to the exposure to Compound (I) and its metabolite BFB-520. QT prolongation was particularly obvious in a patient who was CYP2D6 poor metabolizer and who showed high plasmatic levels of BFB-520. A further analysis of the relationship between QT/QTc and Compound (I) and BFB-520 concentrations was performed. It was determined that to avoid QT prolongation, Cmax of Compound (I) and BFB-520 should not exceed 80 ng/mL and 12 ng/mL respectively.

In order to further evaluate the incidence of QT/QTc changes from baseline greater than 30 and 60 ms and the incidence of QTc values greater than 450, 480 and 500 ms, the following study was conducted.

Part 1 of this study was designed to characterize and compare the pharmacokinetic (PK) profile of Compound (I) when administered as MR formulations, and food effects, following a single dose administration in a 6-way, within subject, crossover design.

Part 2 of the study was designed to evaluate the effect of multiple doses of the MR formulation chosen on safety, tolerability and cardiovascular parameters. Effects of Compound (I) on sleep parameters will be also evaluated. In the CYR-101C01 study, Compound (I) had an effect on slow wave sleep (SWS) distribution: Compound (I) significantly increased SWS in the first third of the night and decreased it in the last third of the night. Results also suggested that Compound (I) could have sleep promoting effects since it improved sleep initiation parameters (sleep onset latency, latency to persistent sleep). In the current study, sleep will be used as a biomarker that could help in defining the minimal active dose to be assessed in the next patient study. Sleep parameters will be analyzed by mean of VWatch methodology.

The formulations used in Part 1 of the study were selected from a design space with active treatment, Compound (I) and HPMC a release controlling agent as the 2 main compositional variables. On the release rate axis of the design space, MR formulations will be described as slow (release rate of 16-19 hours), medium (release rate of 10-12 hours) or fast (release rate of 5-7 hours). The 2-dimensional compositional formulation design space is shown in Scheme 1, where F1 to F4 represent the boundary formulations.

Part 2 of the study was designed to assess the multiple dose administration of the selected formulation from Part 1 at a low and high dose level compared with placebo in a larger naïve cohort of subjects.

Pharmacologic Profile (Nonclinical Studies)

In in vitro receptor binding studies, Compound (I) demonstrated a unique binding profile. Compound (I) bound with high affinity only to 5-HT2A, α1-adrenergic and sigma2 receptors ($K_i$=7.53, 14.43, 8.19 nmol/L, respectively). The affinity for DA receptors was fairly weak ($IC_{50}$>1000 nmol/L). Both main metabolites BFB-520 and BFB-999 showed a similar profile as Compound (I), with lower affinity for σ2 receptors, and lower and equal affinity to that of Compound (I) for 5-HT2A receptors, respectively.

In in vivo functional tests, Compound (I) acted as an antagonist at sigma2 and 5-HT2A receptors. Following oral administration, Compound (I) slightly increased dopamine turnover in the accumbens and striatum and increased the output of DA metabolites such as DOPAC and HVA in prefrontal cortex at high dose levels. At effective dose levels in animal models of antipsychotic activity, Compound (I) did not affect monoamine levels, whereas, other antipsychotics markedly increased DA turnover and the output of DOPAC and HVA, reflecting their potent D2 antagonistic effects.

Compound (I) was tested in male Wistar rats in several behavioral paradigms designed to evaluate the potential for producing antipsychotic activity of drugs in humans. Compound (I) inhibited methamphetamine-, apomorphine-, and phencyclidine-induced hyperlocomotion in a similar manner to other antipsychotics. Likewise, BFB-520 and BFB-999 also inhibited methamphetamine-induced hyperlocomotion with an ED50 higher than that of Compound (I). Furthermore, Compound (I) significantly ameliorated PCP-induced social interaction impairment after repeated administration, whereas, other atypical antipsychotics did not ameliorate this impairment, and improved impairment of spontaneous alternation behavior induced by MK-801.

Safety Pharmacology

In a series of safety pharmacology studies, the effects of Compound (I) on general activity and behavior, the CNS, respiratory function, gastrointestinal system, and water and electrolyte excretion were examined in rats at an oral dose range of 1 to 30 mg/kg Compound (I) induced various changes in general activity and behavior. These clinical signs were observed between 0.25 to 4 hours post-dosing and disappeared by 6 hours post-dosing. Compound (I) inhibited CNS function and decreased thresholds for electroshock-induced convulsion. High doses (>10 mg/kg) of Compound (I) affected respiratory function, inhibited gastric emptying, damaged the gastrointestinal membrane, decreased urine volume, and increased urine potassium excretion.

The effects of Compound (I) on the cardiovascular system were examined in in vitro and in vivo studies. In in vitro electrophysiological studies using guinea pig papillary muscle, Compound (I) at 1 µM or more prolonged the action potential duration (APD) and at the same degree as risperidone and haloperidol. Likewise, BFB-520 at 0.1 µM or more and BFB-999 at 1 µM or more prolonged the APD in isolated guinea pig papillary muscles with the same or stronger degree than Compound (I). In in vitro electrophysiological studies using cultured cells expressing cloned cardiac ion channels, Compound (I) inhibited IKr current with an IC50 of 0.325 µM, comparable to that of risperidone (0.319 µM). As for BFB-520, it blocked IKr current with an IC50 of 0.181 µM lower than that of the parent compound but higher than those of haloperidol (0.026 µM), thioridazine (0.145 µM) or ziprasidone (0.134 µM).

Pharmacokinetic Profile

Pharmacokinetic (PK) studies of Compound (I) have been performed particularly in rats and monkeys. Following a single oral administration, Compound (I) was rapidly absorbed. Plasma radioactivity peaked between 0.63 and 2.75 hours in male rats, and between 3 and 3.5 hours in male monkeys. The oral absorption rates were 90.3 to 94.7% in rats and 70.0 to 99.9% in monkeys. The elimination half-lives of radioactivity from plasma were 45.13 to 51.52 hours in rats and 174.74 to 184.78 hours in monkeys. The elimination half-lives of unchanged Compound (I) were 1.68 to 2.06 hours in rats, and 1.68 to 2.57 hours in monkeys. The absolute oral bioavailability of Compound (I) was 52.4 to 64.5% in rats and 90% or higher in monkeys.

During repeated administration of 1 mg/kg/day for 14 days to male rats, plasma radioactivity increased with increasing number of doses, reaching steady-state after the 7th administration. Food and gender effects were also assessed in rats. When Compound (I) was administered orally to non-fasted rats at 1 mg/kg, plasma radioactivity has a delayed $T_{max}$ by about 1 h and a decreased $C_{max}$ to about 72% of the value in fasted male rats, though AUCs were similar in the two groups. Moreover pharmacokinetic parameters for total radioactivity in female rats were comparable to those in male rats. When $^{14}$C-Compound (I) was orally administered to lactating rats, it was considered that Compound (I) and/or its metabolites rapidly transferred into milk and were slowly eliminated.

Compound (I) absorption was also studied in single and repeated dose toxicity studies in rats and monkeys for toxicokinetics and, in genotoxicity and embryofetal development studies for plasma exposure evidence. After single and repeated administration, exposure levels of Compound (I) and its main metabolites BFB-520 and BFB-999 increased in a dose-dependent manner in both rats and monkeys, with gender difference in rats only.

After single administration of BFB-520 in monkeys, exposure levels of BFB-520, Compound (I) and BFB-999 increased with a dose increment larger than the proportionate one. BFB-520 reached its maximum concentration within 4 hours post-dosing, and $T_{max}$ for Compound (I) and BFB-999 were comparable to that of BFB-520. Finally, the brain transfer of Compound (I) was studied with male rats after oral administration (10 mg/kg). The $C_{max}$ of plasma and brain concentrations were 3164.62 ng/mL and 4946.62 ng/g, respectively. The $K_p$ value (brain/plasma concentration ratio) was 1.38 mL/g.

Several metabolites (i.e. BFB-999, BFB-520 and BFB-885) were detected in plasma and urine of male and female rats and male monkeys after oral administration of 14C Compound (I). The metabolic rate in female rats was slower than that in male rats, but the metabolic profiles were similar between male and female rats. Even if Compound (I) was shown to be metabolized in BFB-520 and BFB-999 by cytochromes P450 CYP1A2, CYP2C19, CYP2D6 and CYP3A4, further studies using human liver microsomes suggest that Compound (I) is mainly metabolized by enzymatic reaction other than CYP isoforms. As for BFB-520, it was metabolized by CYP2D6 and CYP3A4. No remarkable inhibitory effects on human P450 isoforms (CYP1A2, 2A6, 2B6, 2C8/9, 2C19, 2E1 and 3A4) were observed, while a weak inhibitory effect was shown on CYP2D6. Investigation of the drug-drug interaction of Compound (I) on in vitro metabolism determined $IC_{50}$ value more than 50 μM for the following concomitant drugs: ketoconazole, fluvoxamine, paroxetine, and lorazepam.

The major route of elimination of radioactivity in rats and monkeys following a single oral or intravenous administration was via the feces. The excretion to bile was 44.2% within 48 hours after a single oral administration to bile duct cannulated rats. Urinary excretion rates of radioactivity were about 35% in rats and monkeys. Total recovery of given radioactivity was 101.1% (including the carcass) for rats and 92.6% for monkeys within 168 hours after a single oral administration. After repeated administration to rats for 14 days, the total recovery of given radioactivity was 96.6% in urine and feces, and 0.7% in carcass within 168 hours after the last administration. The enterohepatic circulation rate was determined to be about 27% after intraduodenal administration of bile samples from $^{14}$C-Compound (I)-treated rats.

In an embodiment, the compositions may be formulated in a conventional manner using one or more pharmaceutically acceptable carriers and may also be administered in controlled-release formulations.

Example 2

Part 1 of the study is an open-label, non-randomized, single dose, 6-period crossover design in 12 healthy CYP 2D6 EM male subjects. For Part 1, subjects will receive the following regimens in a non-randomised manner:

Regimen A: MR Formulation prototype 1: 32 mg Compound (I) slow release administered in the fasted state Regimen B: MR Formulation prototype 2 administered in the fasted state Regimen C: MR Formulation prototype 3 administered in the fasted state or formulation prototype 1 or 2 administered in the fed state Regimen D: MR Formulation prototype 4 administered in the fasted state or formulation prototype 1, 2 or 3 administered in the fed state Regimen E: MR Formulation prototype 5 administered in the fasted state or formulation prototype 1, 2, 3 or 4 administered in the fed state Regimen F: MR Formulation prototype 1, 2, 3, 4 or 5 administered in fed state.

Formulation selection within Part 1 are made after a complete review of all data collected from the previous regimen and the formulation, doses and requirement for the optional return visit for Part 2 are made after a complete review of all data from Part 1.

Part 2 of the study is a double-blind, randomized, placebo-controlled, 6-sequence, 3-period crossover design in 24 healthy CYP 2D6 EM male and female subjects. For Part 2, on each of the 3 study periods, subjects receive the following regimes in a randomized manner:

Regimen G: Placebo QD for 7 days

Regimen H: High dose MR formulation prototype QD for 7 days

Regimen I: Low dose MR formulation prototype QD for 7 days

Based on the above concept of design space, the IMP formulations used in Part 1 of the study are selected from a design space with active treatment Compound (I) and Hypromellose (HPMC) as the release controlling agent (the release controlled by the HPMC viscosity based on the ratio of 2 HPMC polymers) as the two main compositional variables. The 2-dimensional compositional formulation design space is shown in Table 1, where F1 to F4 represent the boundary formulations. Part 2 of the study is designed to assess the multiple dose administration of the selected formulation from Part 1 at a low and high dose level compared with placebo in a larger naïve cohort of subjects.

TABLE 1

| | Excipient Quantitative Composition Range for Design Space | | | |
|---|---|---|---|---|
| Component | 16 mg Slow Formulation 1 % w/w | 64 mg Slow Formulation 2 % w/w | 16 mg Fast Formulation 3 % w/w | 64 mg Fast Formulation 4 % w/w |
| Compound (I)* | 6.40 | 25.60 | 6.40 | 25.60 |
| Hypromellose K100LV CR | 12.00 | 6.00 | 36.00 | 30.00 |
| Hypromellose K4M CR | 24.00 | 24.00 | — | — |
| Microcrystalline Cellulose PH102** | 36.10 | 22.90 | 36.10 | 22.90 |
| Lactose Fastflo 316 | 20.00 | 20.00 | 20.00 | 20.00 |

TABLE 1-continued

Excipient Quantitative Composition Range for Design Space

| Component | 16 mg Slow Formulation 1 % w/w | 64 mg Slow Formulation 2 % w/w | 16 mg Fast Formulation 3 % w/w | 64 mg Fast Formulation 4 % w/w |
|---|---|---|---|---|
| Silica Colloidal Anhydrous, Aerosil 200 Pharma | 0.50 | 0.50 | 0.50 | 0.50 |
| Magnesium stearate | 1.00 | 1.00 | 1.00 | 1.00 |
| Total | 100.00 | 100.00 | 100.00 | 100.00 |

*Salt correction factor of 1.2 applied.
**The amount of Microcrystalline Cellulose PH102 will be adjusted accordingly to maintain the same tablet weight.

Under the composition details we therefore present the extremes of dose range of 16-64 mg Compound (I) and ranges for levels of Hypromellose K100LV CR and Hypromellose K4M CR in the MR tablet, with the understanding that any interim formulation within these ranges the formulation design space approach described in Section 2.1.P.1, this formulation represents the extremes of dose range of 16-64 mg Compound (I) and ranges in concentrations of Hypromellose K100LV CR and Hypromellose K4M CR that could be used in the study.

TABLE 2

Composition of Compound (I) Prototype MR Tablet (Formulations 1, 2, 3 and 4)

| Component | 16 mg Slow Formulation 1 mg/tablet | 64 mg Slow Formulation 2 mg/tablet | 16 mg Fast Formulation 3 mg/tablet | 64 mg Fast Formulation 4 mg/tablet | Function | Ref. to Standard |
|---|---|---|---|---|---|---|
| Compound (I)[1] | 19.20 | 76.80 | 19.20 | 76.80 | Active | DS Section or other as appropriate |
| Hypromellose K100LV CR | 36.00 | 18.00 | 108.00 | 90.00 | Release Modifier | USP, Ph. Eur., JP |
| Hypromellose K4M CR | 72.00 | 72.00 | — | — | Release Modifier | USP, Ph. Eur., JP |
| Microcrystalline Cellulose PH102[2] | 108.30 | 68.70 | 108.30 | 68.70 | Filler | Ph. Eur., NF, JP |
| Lactose Fastflo 316 | 60.00 | 60.00 | 60.00 | 60.00 | Filler | NF/USP, Ph. Eur., JP |
| Silica Colloidal Anhydrous, Aerosil 200 Pharma | 1.50 | 1.50 | 1.50 | 1.50 | Glidant | USP, Ph. Eur., JP |
| Magnesium stearate | 3.00 | 3.00 | 3.00 | 3.00 | Lubricant | Ph. Eur., NF, JP |
| Total weight | 300.00 | 300.00 | 300.00 | 300.00 | | |

[1] Salt correction factor of 1.2 applied
[2] The amount of Microcrystalline Cellulose PH102 will be adjusted accordingly to maintain the same tablet weight.

could be manufactured and dosed as an IMP during the clinical study. All other components of the formulations remain constant with the exception of Microcrystalline Cellulose PH102 which may be adjusted to maintain tablet weight based on the potency and purity of the drug substance and weights for Hypromellose K100LV CR and Hypromellose K4M CR. The final composition of the selected formulations is recorded in batch records produced for clinical trial manufactures.

Composition of Compound (I) Prototype MR Tablet (Formulations 1, 2, 3, and 4)

The complete statement of the components and quantitative composition of Compound (I) Prototype MR Tablet Formulations 1, 2, 3, and 4 is given in Table 2. In line with Table 3 shows the batch formulae for Compound (I) Prototype MR Tablet Formulations 1, 2, 3 and 4. These formulations represent the extremes of the dose range of Compound (I) and concentrations of Hypromellose K100LV CR and Hypromellose K4M CR that could be used in the study. The compositional ratio of Silica Colloidal Anhydrous, Lactose Fastflo 316 and Magnesium Stearate will remain constant. The compositional ratio of Microcrystalline Cellulose PH102 may be adjusted based on the potency and purity of the drug substance and the weights for Hypromellose K100LV CR and Hypromellose K4M CR to maintain tablet weight of 300 mg.

TABLE 3

"Design Space" Batch Formulae for Compound (I) Prototype MR Tablet

| Component | 16 mg Slow Formulation 1 % w/w | 64 mg Slow Formulation 2 % w/w | 16 mg Fast Formulation 3 % w/w | 64 mg Fast Formulation 4 % w/w |
|---|---|---|---|---|
| Compound (I)[1] | 6.40 | 25.60 | 6.40 | 25.60 |
| Hypromellose K100LV CR | 12.00 | 6.00 | 36.00 | 30.00 |
| Hypromellose K4M CR | 24.00 | 24.00 | — | — |
| Microcrystalline Cellulose PH102[2] | 36.10 | 22.90 | 36.10 | 22.90 |
| Lactose Fastflo 316 | 20.00 | 20.00 | 20.00 | 20.00 |
| Silica Colloidal Anhydrous, Aerosil 200 Pharma | 0.50 | 0.50 | 0.50 | 0.50 |
| Magnesium stearate | 1.00 | 1.00 | 1.00 | 1.00 |
| Total | 100.00 | 100.00 | 100.00 | 100.00 |

[1]Salt correction factor of 1.2 applied.
[2]The amount of Microcrystalline Cellulose PH102 will be adjusted accordingly to maintain the same tablet weight.

Scheme 2: Manufacture of Compound (I) Prototype MR Tablet

| Component | Process | Control |
|---|---|---|
| Compound (I)<br>Hypromellose K100LV CR<br>Hypromellose K4M CR (if required)<br>Microcrystalline Cellulose PH102<br>Lactose Fastflo 316<br>Silica Colloidal Anhydrous, Aerosil 200 Pharma | Weigh the required quantity of Compound (I), Hypromellose K100LV CR, Hypromellose K4M CR (if required), Microcrystalline Cellulose PH102, Lactose Fastflo 316 and Silica Colloidal Anhydrous and screen through a suitably sized sieve. Transfer into a suitably sized container and mix. Screen the entire blend through a suitably sized sieve. Transfer into the original suitably sized container and mix.<br>↓ | Quantity of Compound (I)<br>Quantity of Hypromellose K100LV CR<br>Quantity of Hypromellose K4M CR (if required)<br>Quantity of Microcrystalline Cellulose PH102<br>Quantity of Lactose Fastflo 316<br>Quantity of Silica Colloidal Anhydrous, Aerosil 200 Pharma<br>Mesh size of sieve screen<br>Mixing Time and Speed |
| Magnesium stearate | Weigh the required quantity of Magnesium Stearate and screen through a suitably sized sieve. Transfer to the container above and mix This is the Compound (I) Prototype MR Tablet Blend<br>↓ | Quantity of Magnesium Stearate<br>Mesh size of sieve screen<br>Mixing Time and Speed |

| Scheme 2: Manufacture of Compound (I) Prototype MR Tablet | | |
|---|---|---|
| Component | Process | Control |
| Compound (I) Prototype MR Tablet Blend | Compress the Compound (I) Prototype MR Tablet Blend into tablets This is the Compound (I) Prototype MR Tablet. ↓ Package the Compound (I) Prototype MR Tablet in container closure. | Quantity of Compound (I) Prototype MR Tablet Blend [1]Tablet appearance [2]Compression force [3]Tablet Hardness [4]Tablet weight |

[1]Tablet appearance will be assessed as an in process control during batch manufacture, the details of which will be recorded in the batch manufacturing record
[2]Compression force will be used throughout the manufacturing process and this may be adjusted to ensure that the correct tablet hardness is achieved.
[3]Tablet hardness will be measured periodically throughout batch manufacture as defined in the batch manufacturing record.
[4]Tablet weight will be measured as an in process control during batch manufacture, the details of which will be recorded in the batch manufacturing record.

The amount of Compound (I) and each excipient is controlled by weight using a suitably calibrated balance to confirm that the correct formulation composition is achieved. A second operator verifies the weight. Blend uniformity is controlled by the pre-defined mixing conditions detailed in Scheme 2. These parameters have been developed to ensure homogeneity of all potential formulation blends within the proposed design space. Execution of these processing instructions will be controlled and documented within the batch manufacturing record. To ensure that content uniformity is uniform throughout the design space, development batches at the points in the design space described in Scheme 1 have been manufactured and tested. Uniformity of content of the final tablet is assessed by assay.

Tablet hardness is controlled by application of a consistent pressure with regular testing (destructive) throughout the batch using the Tablet Compression Hardness Test.

The tablets are pressed manually; each tablet is weighed separately using a suitably calibrated balance and a second operator verifies the weight.

All excipients used in the formulations comply with the current monographs of the Ph. Eur., the USP/NF or JP requirements as indicated below. All excipients are purchased from approved suppliers. Manufacturer's Certificate of Analysis will be accepted and all excipients received at Quotient Clinical Ltd will undergo identification tests as appropriate according to Quotient Clinical Ltd receipt requirements.

TABLE 4

| Specification for Compound (I) Prototype MR Tablet | | |
|---|---|---|
| Test | Method | Acceptance Criteria |
| Appearance | Visual | Off-white tablets with mottled beige speckles, free from visual defects |
| Assay | HPLC | 90.0%-110.0% of nominal |
| Identity | HPLC | Retention time of test sample conforms with the retention time of reference standard ±3% |
| Related Substances | HPLC | Report ≥ 0.1% Impurity A ≤ 1.0% 2-isomer ≤ 1.0% Unspecified Impurities NMT 0.5% |

TABLE 4-continued

| Specification for Compound (I) Prototype MR Tablet | | |
|---|---|---|
| Test | Method | Acceptance Criteria |
| Content Uniformity | HPLC | Total Impurities NMT 3.0% AV ≤ 15.0 |
| Dissolution | HPLC | Report results |

Dissolution Test

The dissolution test is a pharmacopoeial method conducted according to USP monograph <711> apparatus 2. The dissolution medium is 450 mL 0.01M hydrochloric acid with a pH switch with double strength Fasted State Simulated Intestinal Fluid (version 2) giving a total volume of 900 mL and agitation at 75 rpm.

Figure 7:
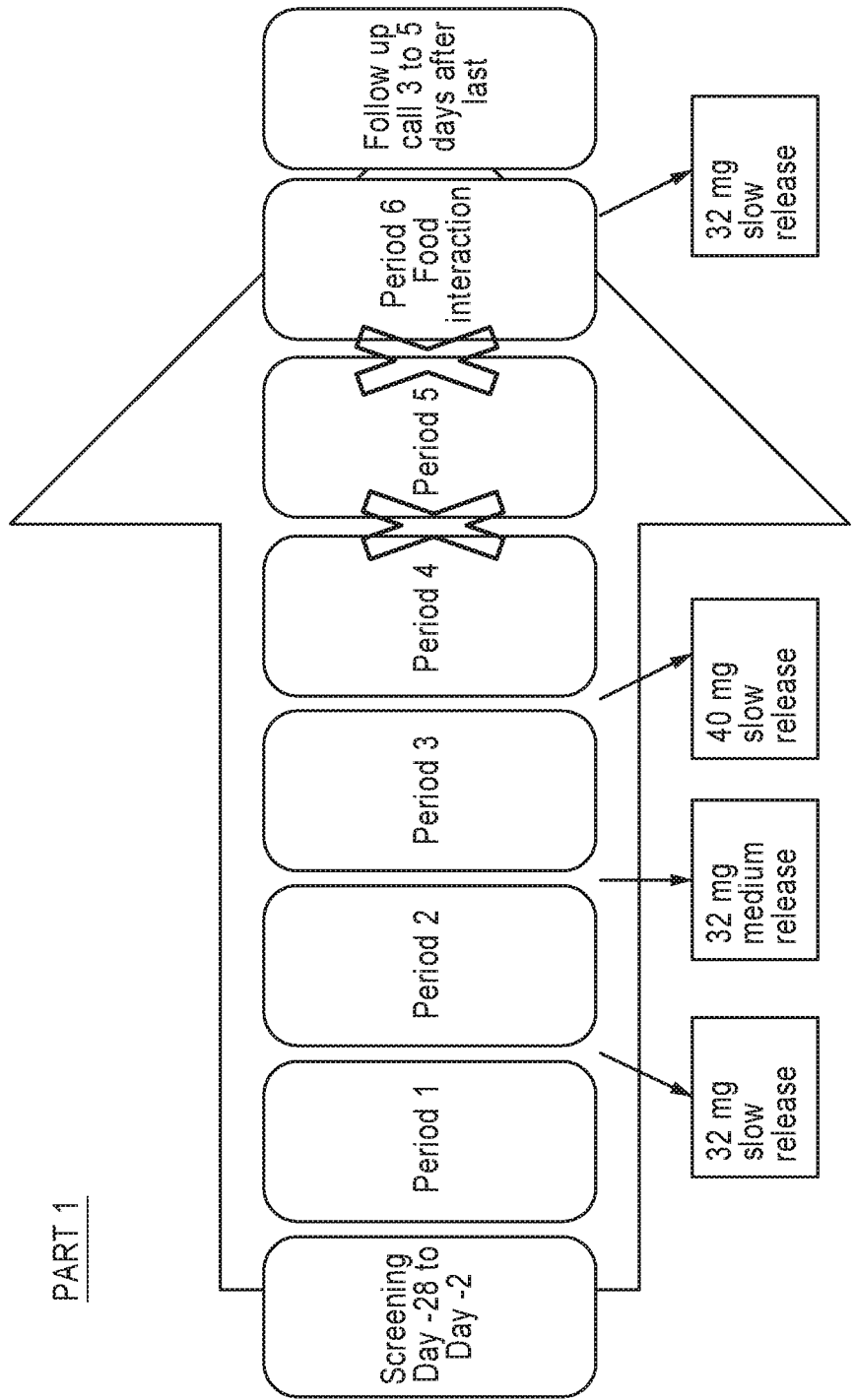
FIG. 7 is a diagram illustrating Part 1 Study Design.
Figure 8:
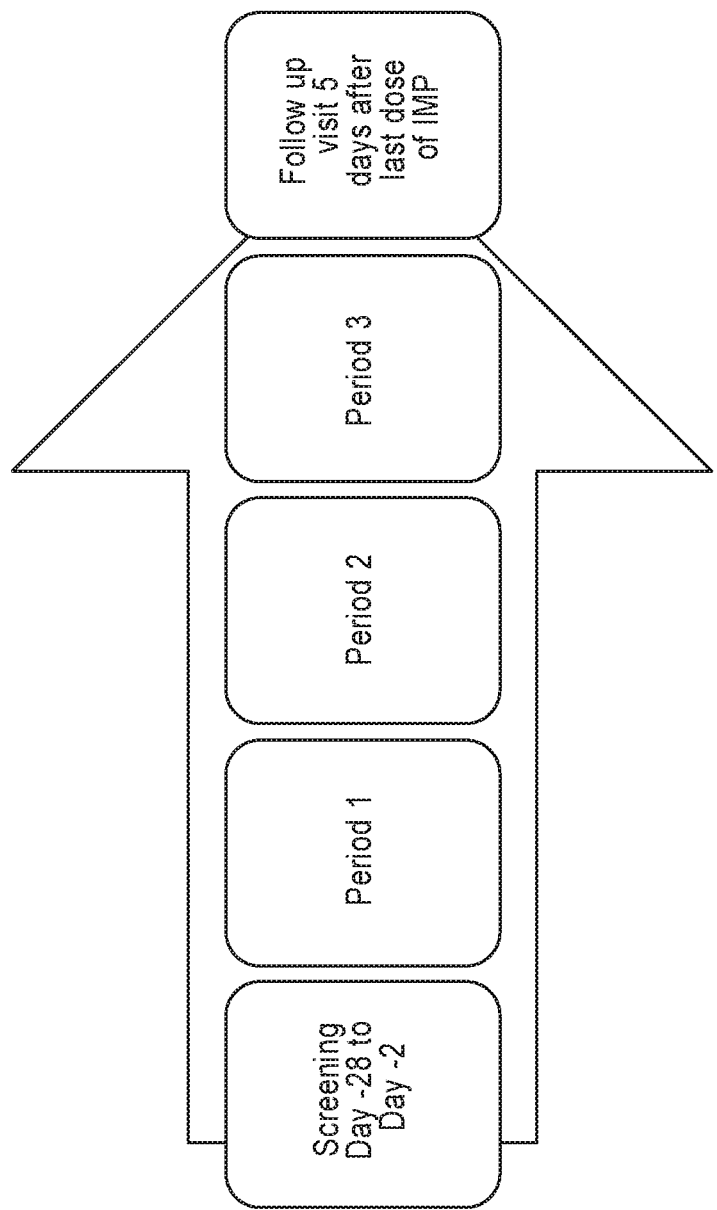
FIG. 8 is a diagram illustrating Part 2 Study Design.
Figure 9:
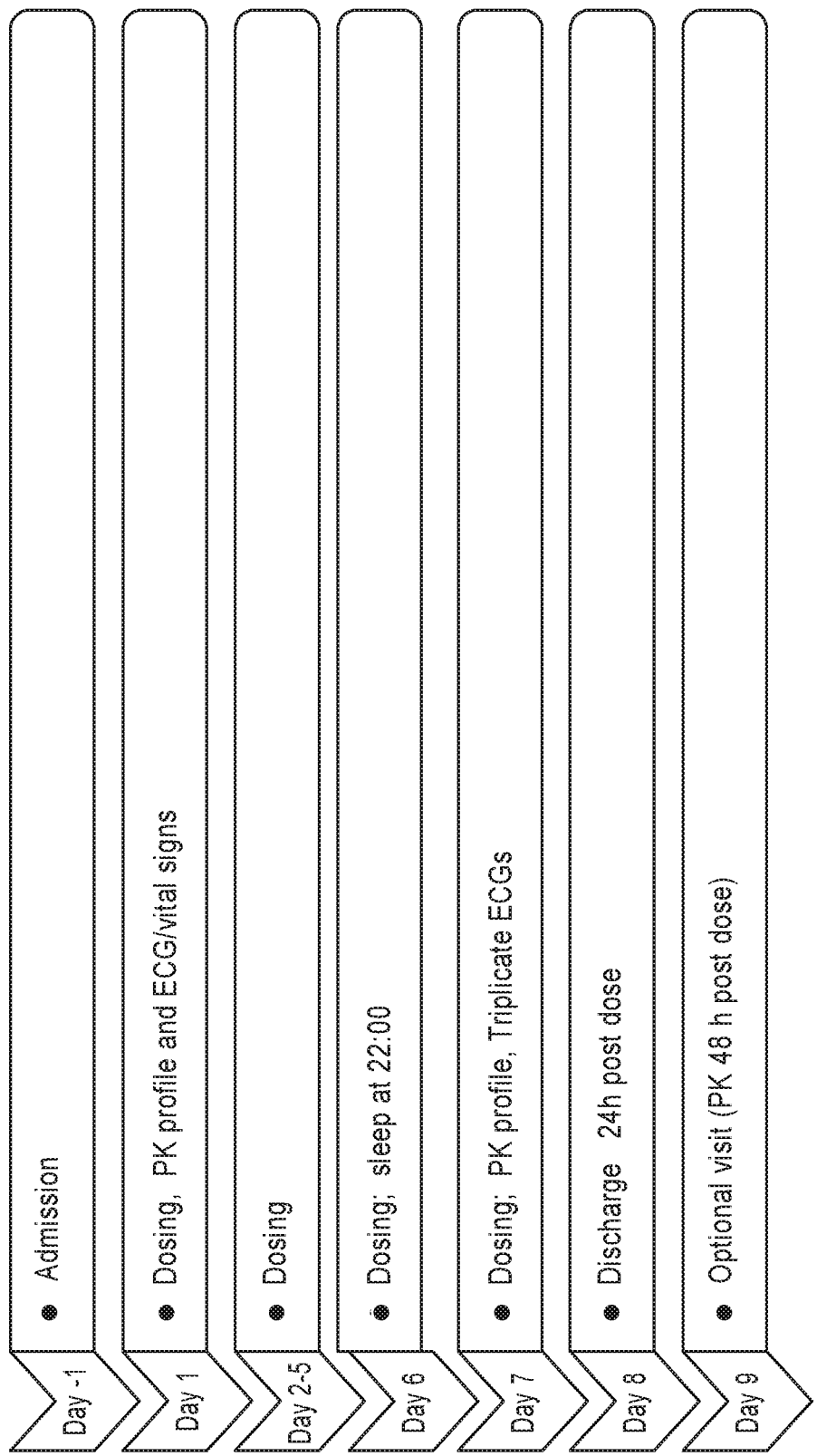
FIG. 9 is a diagram illustrating Study Period Scheme.

Samples are analyzed for Compound (I) content by a reverse phase isocratic HPLC method using an Intersil ODS-3V (4.6 mm×150 mm) 5 μm column or suitably validated alternative with UV detection at 248 nm. Mobile phase is comprised of Acetonitrile:Water:Trifluroacetic acid. Description of HPLC Assay, Identity and Content Uniformity Method for Compound (I) Prototype MR Tablets The method for assay of the active ingredient content of the Compound (I) Prototype MR Tablet is a reverse phase isocratic HPLC method using an Intersil ODS-3V (4.6 mm×150 mm) 5 μm column or suitably validated alternative with UV detection at 248 nm. Mobile phase is comprised of Acetonitrile:Water:Trifluroacetic acid.
Description of Related Substances Test The method for related substances of the Compound (I) Prototype MR Tablet is a reverse phase gradient HPLC method using an Intersil ODS-3V (4.6 mm×150 mm) 5 μm column or suitably validated alternative with UV detection at 248 nm. Mobile phase A is comprised of 0.1% TFA in Water, mobile phase B is 0.1% TFA in Acetonitrile.
Compound (I) C02: Once a Day Formulation A Two-Part Study Designed to Evaluate the Pharmacokinetic Profile of Compound (I) and its Main Metabolites Following Single and Multiple Dose Modified Release Prototype Formulation Administration in Healthy CYP2D6 Extensive Metabolizer Male and Female Subjects, and to Evaluate the Relationship Between the Pharmacokinetic Profile of Compound (I) and its Main Metabolites and Cardiovascular Parameters. The study designs for part 1 and part 2 are shown in FIGS. 7 and 8, respectively, and FIG. 9 shows the period scheme for dosing.

TABLE 5

Summary of Select PK Parameters - Period 1 (32 mg Slow Release, Fasted)

| | Tmax (h) | Cmax (ng/mL) | Tlag (h) | t½ (h) | AUClast (h*ng/mL) |
|---|---|---|---|---|---|
| MIN-101 | | | | | |
| N | 10 | 10 | 10 | 9 | 10 |
| Mean | NA | 22.52 | NA | 6.257 | 211.9 |
| Median | 2.25 | 23.74 | 0 | 5.353 | 220.4 |
| CV % | NA | 28.3 | NA | 38.1 | 18.6 |
| BFB-520 | | | | | |
| N | 10 | 10 | 10 | 4 | 10 |
| Mean | NA | 1.321 | NA | 6.540 | 18.6 |
| Median | 4 | 1.294 | 0.5 | 6.458 | 18.04 |
| CV % | NA | 27.7 | NA | 21.1 | 24.7 |
| BFB-999 | | | | | |
| N | 10 | 10 | 10 | 5 | 10 |
| Mean | NA | 1.510 | NA | 6.202 | 16.02 |
| Median | 3 | 1.436 | 0.25 | 5.486 | 15.22 |
| CV % | NA | 19.5 | NA | 27.3 | 22.3 |

Figure 1:
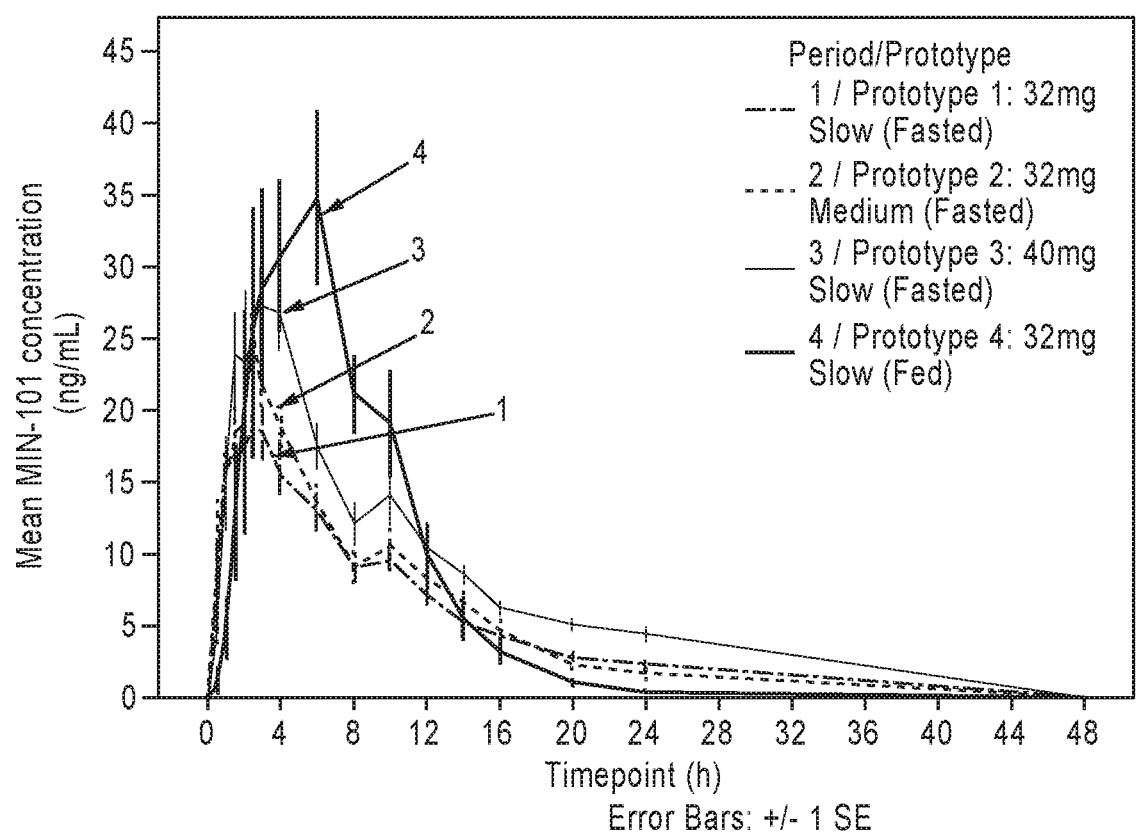
FIG. 1 is a graph illustrating plasma concentration—time profiles of MIN-101.
Figure 2:
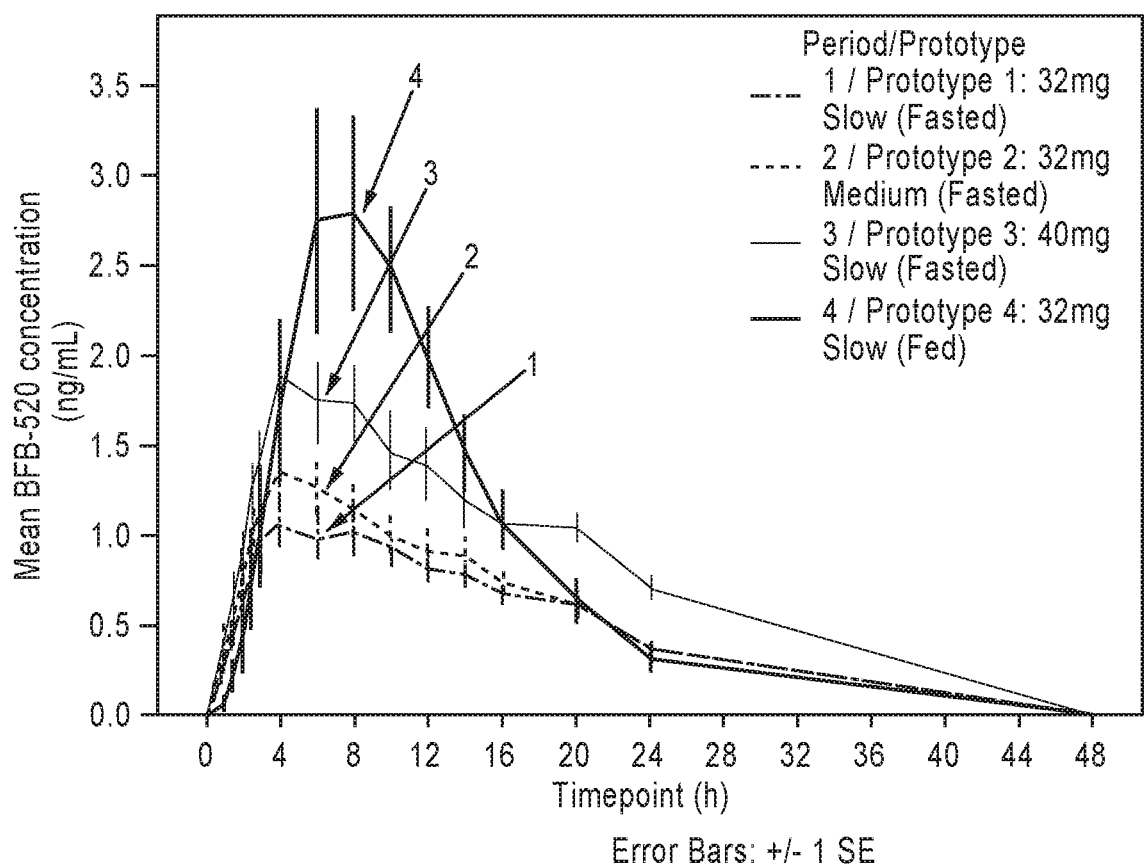
FIG. 2 is a graph illustrating plasma concentration—time profiles of BFB-520.
Figure 3:
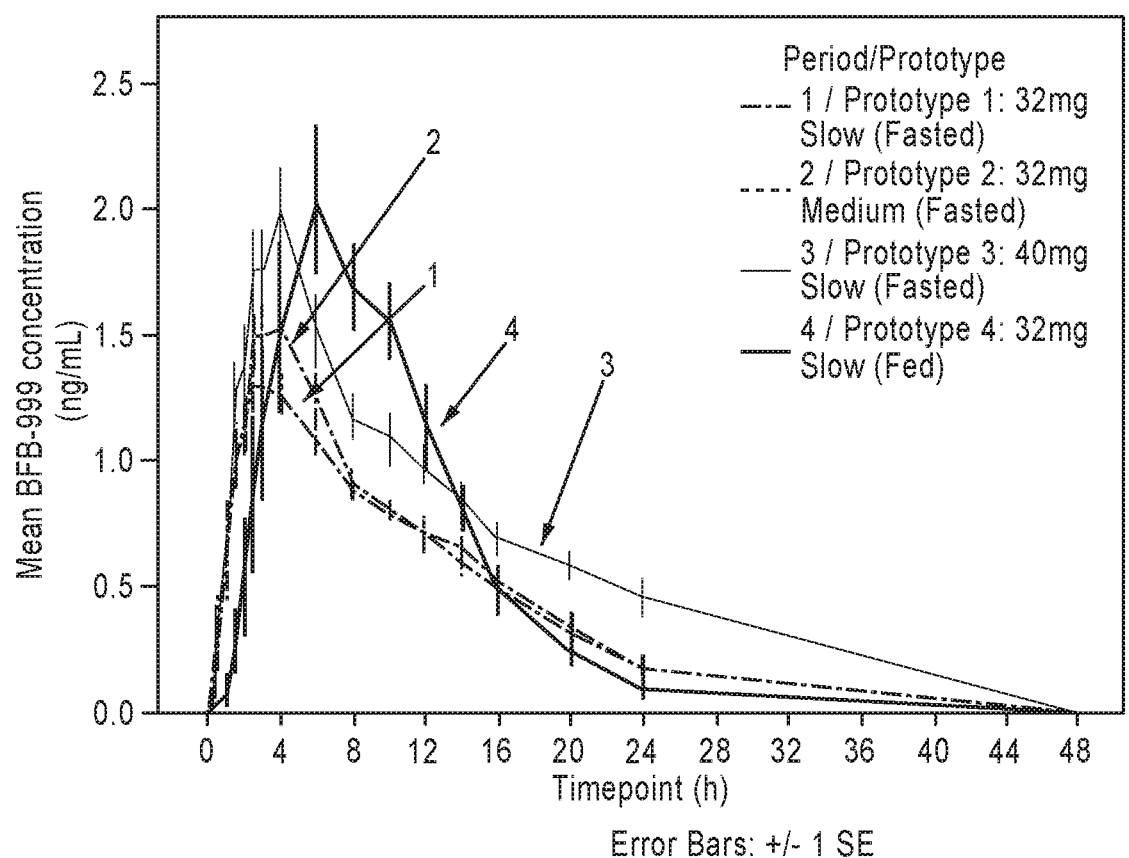
FIG. 3 is a graph illustrating plasma concentration—time profiles of BFB-999.
Figure 4:
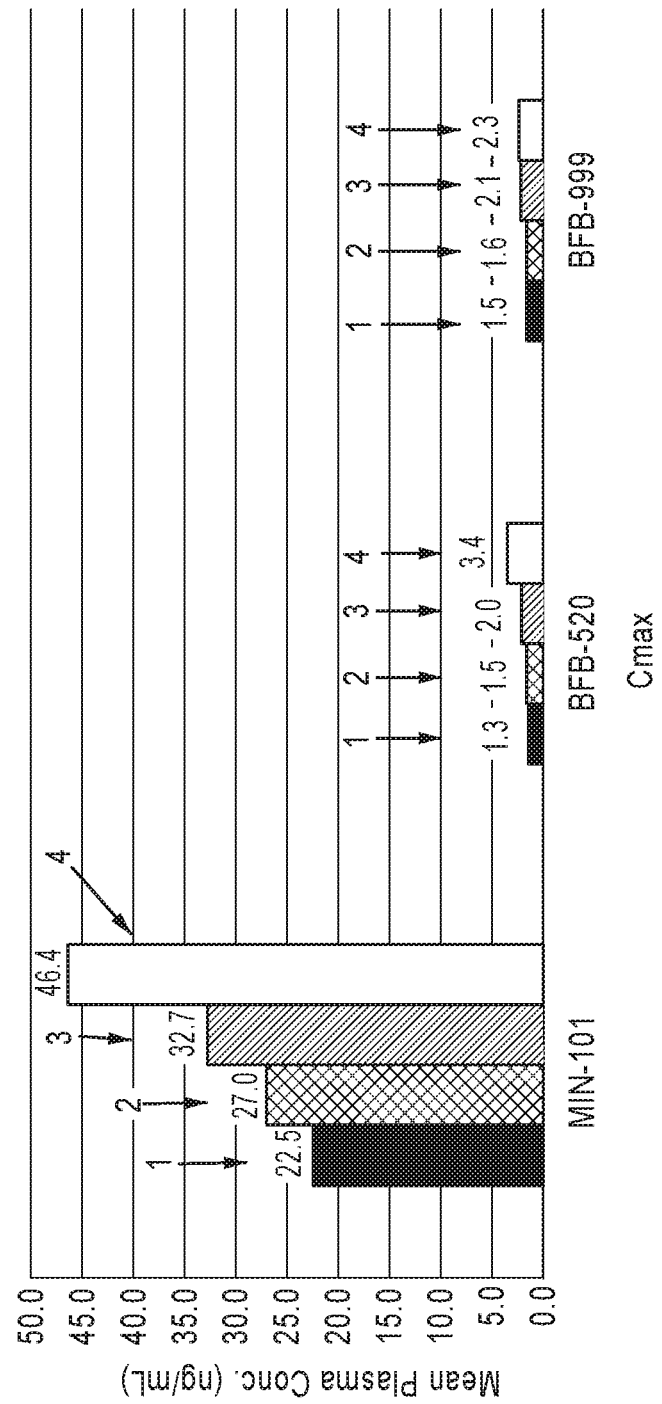
FIG. 4 is a graph illustrating plasma concentrations of MIN-101, BFB-520, and BFB-999 by period.
Figure 5:
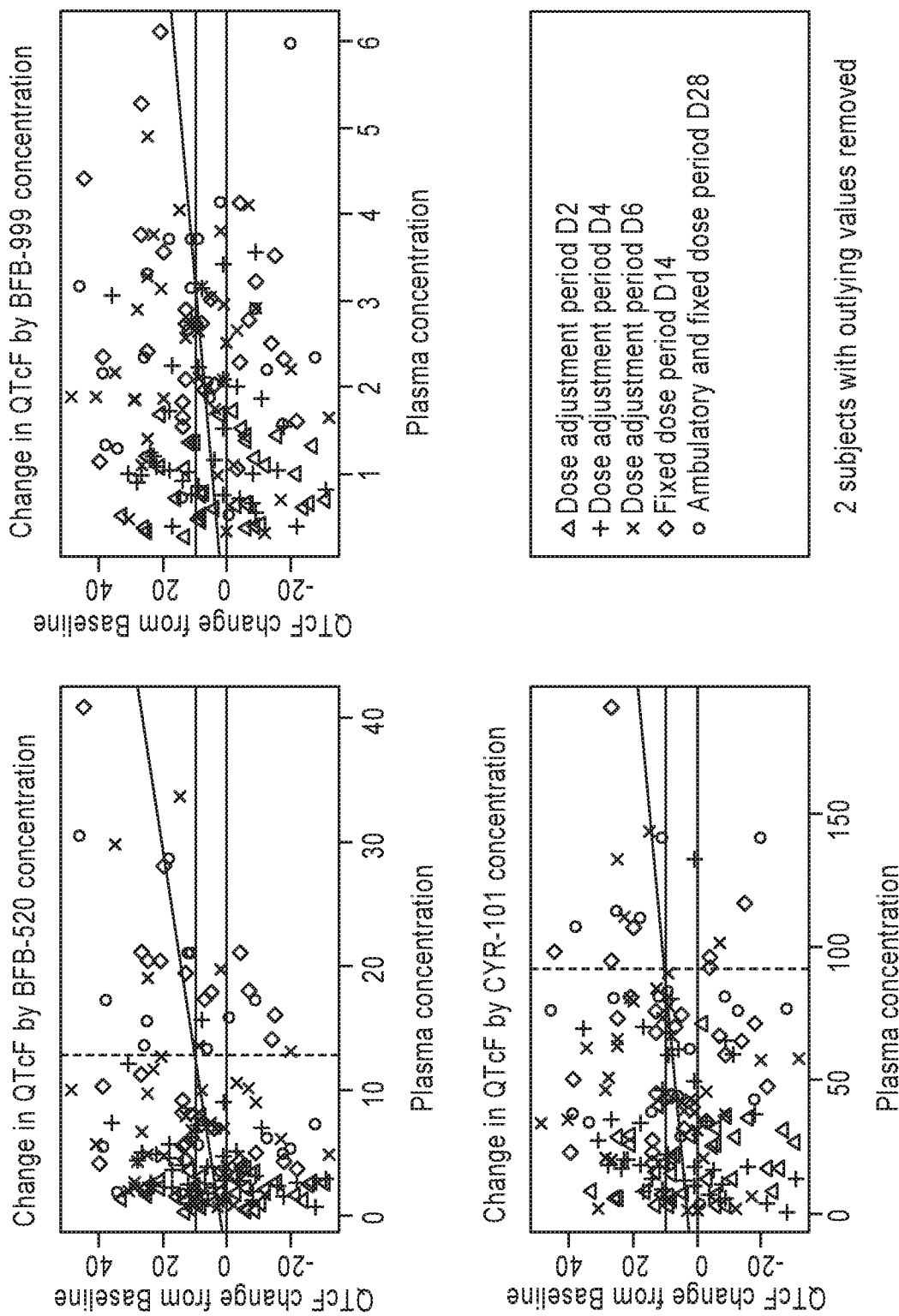
FIG. 5 is a series of graphs illustrating the changes in QTcF by BFB-520, BFB-999, and CYR-101 concentrations.

In addition, the plasma concentration-time profiles for Compound (I), BFB-520, and BFB-999 are shown in FIGS. 1-3. The $C_{max}$ for Compound (I), BFB-520, and BFB-999 is shown in FIG. 4. Effects on QTcF by Compound (I), BFB-520, and BFB-999 is shown in FIG. 5.

MR Formulation under Fasted Conditions:
Short lag time suggestive of fast bioavailability
Exposure variability is generally low
Low to non-quantifiable values for most by Hour 24
PK is generally dose proportional for Compound (I) & BFB-999, and less so for BFB-520
Inversion of BFB-520 & BFB-999 occurred with generally suppressed levels of BFB-520, and a higher BFB-999 to BFB-520 ratio
MR formulation findings suggest shorter time in small intestine is helpful in suppressing BFB-520 levels
Half-life for Compound (I) and 2 metabolite in 3-8 hour range, longer for 40 mg slow release most likely due to flip-flop (absorption & elimination balanced during terminal phase)
Simulation results indicate steady state within 10-14 days, and no accumulation for all 3 analytes.
Food Effect:
Positive food effect evident—Higher exposure
MR formulation behaved similar to IR formulation with rapid release and absorption, mostly prior to reaching colon
  This explains further increase in BFB-520 levels
Due to rapid absorption Compound (I) Cmax increase was ~2×, BFB-520 Cmax increase was ~3×, and BFB-999 Cmax increase was ~0.5×
Half-life was shortened substantially: Fed to Fasted ratios were
  0.5 for Compound (I)
  0.8 for BFB-520
  0.6 for BFB-999
Consequently, accumulation is not expected
AUC increase was minimal (compared to $C_{max}$): 1.3 to 1.8 multiples with highest increase to BFB-520

Figure 10:
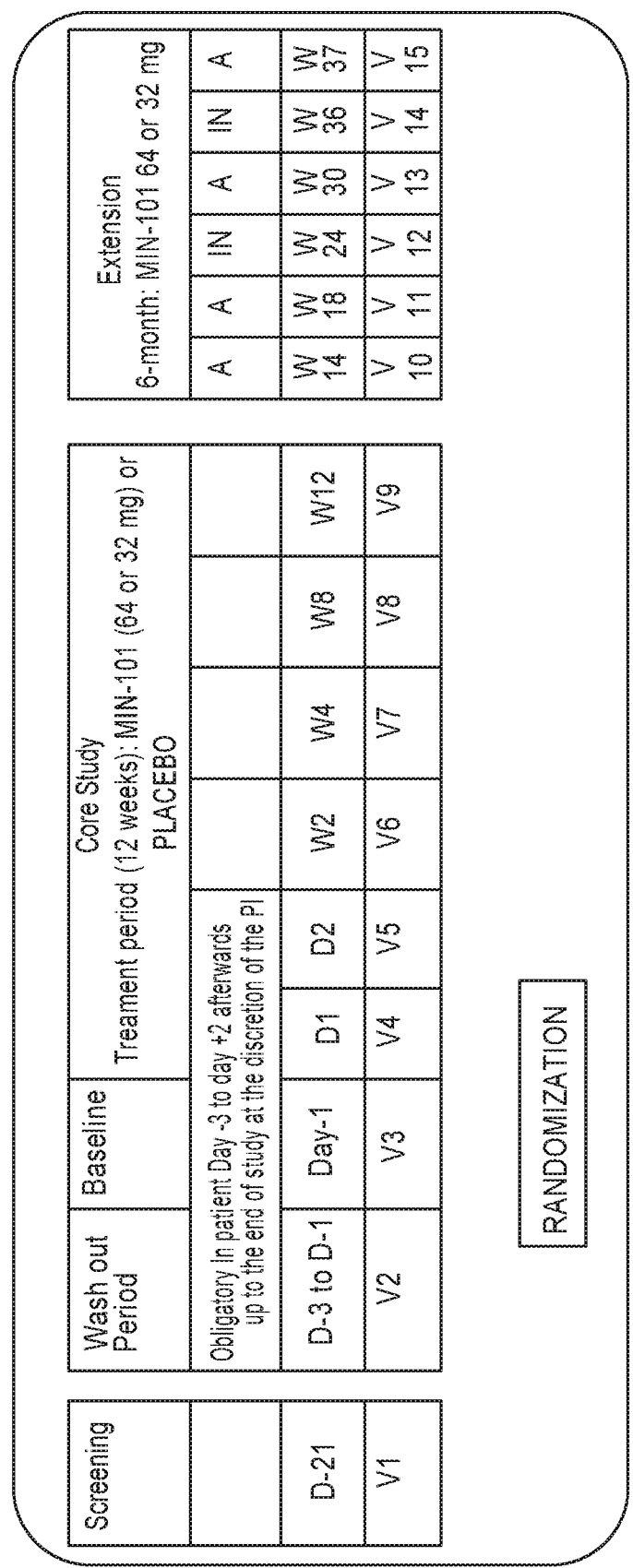
FIG. 10 is a diagram illustrating Global Study Design for Phase IIB in patients with schizophrenia.

Compound (I) C03 Phase IIB in Patients with Schizophrenia
A Phase IIIb, Multi-centre, Randomized, Double-blind, Parallel-group, Placebo-controlled Study to Evaluate the Efficacy, Tolerability and Safety of Compound (I) in Patients with Negative Symptoms of Schizophrenia Followed by a 24-week, Open-label extension. The study design is shown in FIG. 10.
Study Objectives
  Primary:
    To evaluate the efficacy of Compound (I) compared to placebo in improving the negative symptoms of schizophrenia as measured by the change from Baseline in the Positive and Negative Syndrome Scale (PANSS) negative subscale score of the pentagonal model over 12 weeks of treatment.
  Main Secondary
    To evaluate the efficacy of Compound (I) compared to placebo in improving other symptoms of schizophrenia as measured by the change from baseline in the PANSS total score, and sub-scores of the pentagonal model AND 3 factors analysis over 12 weeks of double blind treatment.
    To evaluate the efficacy of Compound (I) compared to placebo in improving negative symptoms of schizophrenia as measured by the change from Baseline in the Brief Negative Symptoms Scale (BNSS) total score over 12 weeks of double blind treatment.
    To assess the effects versus placebo of Compound (I) on cognitive function as measured by the Brief Assessment of Cognition in Schizophrenia (BACS) battery over 12 weeks of double blind treatment.
    To assess the persistence of efficacy, and the safety and tolerability of Compound (I) during the 24-week, of open-label extension phase.
  Other Objectives
    To evaluate the effects versus placebo of Compound (I) on depressive symptoms as measured by the Calgary Depression Scale for Schizophrenia (CDSS) over 12 weeks of double blind treatment.
    To evaluate the effects versus placebo of Compound (I) on social functioning by means of the Personal and Social Performance (PSP) over 12 weeks of double blind treatment.
    To assess the effects versus placebo of Compound (I) on sleep architecture and continuity as measured with the help of the V-Watch methodology over 12 weeks of double blind treatment.
  Main Inclusion Criteria
    Male or female patient, 18 to 60 years of age, inclusive.
    Patient meets the diagnostic criteria for schizophrenia as defined in the Diagnostic and Statistical Manual of Mental Disorders-Fifth Edition (DSM-V)
    Patient being stable in terms of positive symptoms over the last three months according to his treating psychiatrist
    Patient presenting with negative symptoms over the last three months according to his treating psychiatrist
    Patient with PANSS negative sub-score of at least 20.
    Patient with PANSS item score of <4 on: P4 Excitement, hyperactivity P7 Hostility P6 Suspiciousness G8 Uncooperativeness G14 Poor impulse control
    No change in psychotropic medication during the last month
    Patient must be extensive metabolizers for P450 CYP2D6, as determined by genotyping test before the first drug dose is administered.
  Main Exclusion Criteria
    Current bipolar disorder, panic disorder, obsessive compulsive disorder, or evidence of mental retardation.

Patient's condition is due to direct physiological effects of a substance (e.g., a drug of abuse, or medication) or a general medical condition.

Significant risk of suicide or attempted suicide, or of danger to self or others.

Patient who cannot be discontinued from psychotropics other than those allowed.

Patient who received clozapine within 6 months of the Screening visit.

Patient receiving treatment with depot antipsychotic medication can be enrolled in the study 4 weeks after the last injection.

Patient with a history of significant other major or unstable neurological, neurosurgical (e.g., head trauma), metabolic, hepatic, renal, hematological, pulmonary, cardiovascular, metabolic, gastrointestinal, or urological disorder.

Patient with a clinically significant electrocardiogram (ECG) abnormality that could be a safety issue in the study, including QT interval value corrected for heart rate using the Fridericia's formula (QTcF)>430 msec for males and >450 msec for females.

Main Efficacy Assessments

Positive and Negative Symptoms Scale (PANSS)

Brief Negative Symptoms Scale (BNSS): semi structured interview, designed to measure the current level of severity of negative symptoms in schizophrenia and schizoaffective disorder (Kirkpatrick et al.)
  Anhedonia
  Distress
  Asociality
  Avolition
  Blunted affect
  Alogia Brief Assessment of Cognition in Schizophrenia (BACS)

Personal and Social Performance (PSP): assess social functioning; clinician rated
  socially useful activities,
  personal and social relationships,
  self-care
  disturbing and aggressive behavior Sleep architecture and continuity Sleep Assessment Sleep and circadian rhythm disruptions are reported in 30% to 80% of patients with schizophrenia.

Patients with insomnia report
  lower quality of life
  greater symptom severity
  worse adherence/compliance to treatment Sleep disturbances have also been associated with enhanced psychosis Sleep is important for memory consolidation, thus disturbances in sleep architecture, or circadian de-synchronization could also contribute to the cognitive impairment observed in schizophrenia.

Compound (I) showed effects on sleep architecture in the previous Phase 2a study that could possibly be linked to the improvements observed on negative symptoms and cognition, thus they will be further investigated in the present study.
  In a subgroup of patients (20) who underwent sleep recordings (PSG), sleep was evaluated at Baseline and Day 14. Compound (I) had an effect on
    Slow Wave Sleep (SWS) distribution: it shifted SWS from the end to the beginning of the night: Compound (I) significantly increased SWS in the first third of the night and decreased it in the last third of the night.
    Sleep initiation parameters (sleep onset latency, latency to persistent sleep).
  Subjective sleep quality as measured by PSQI improved and this improvement was greater with Compound (I) than with placebo although not statistically significant.

Figure 6:
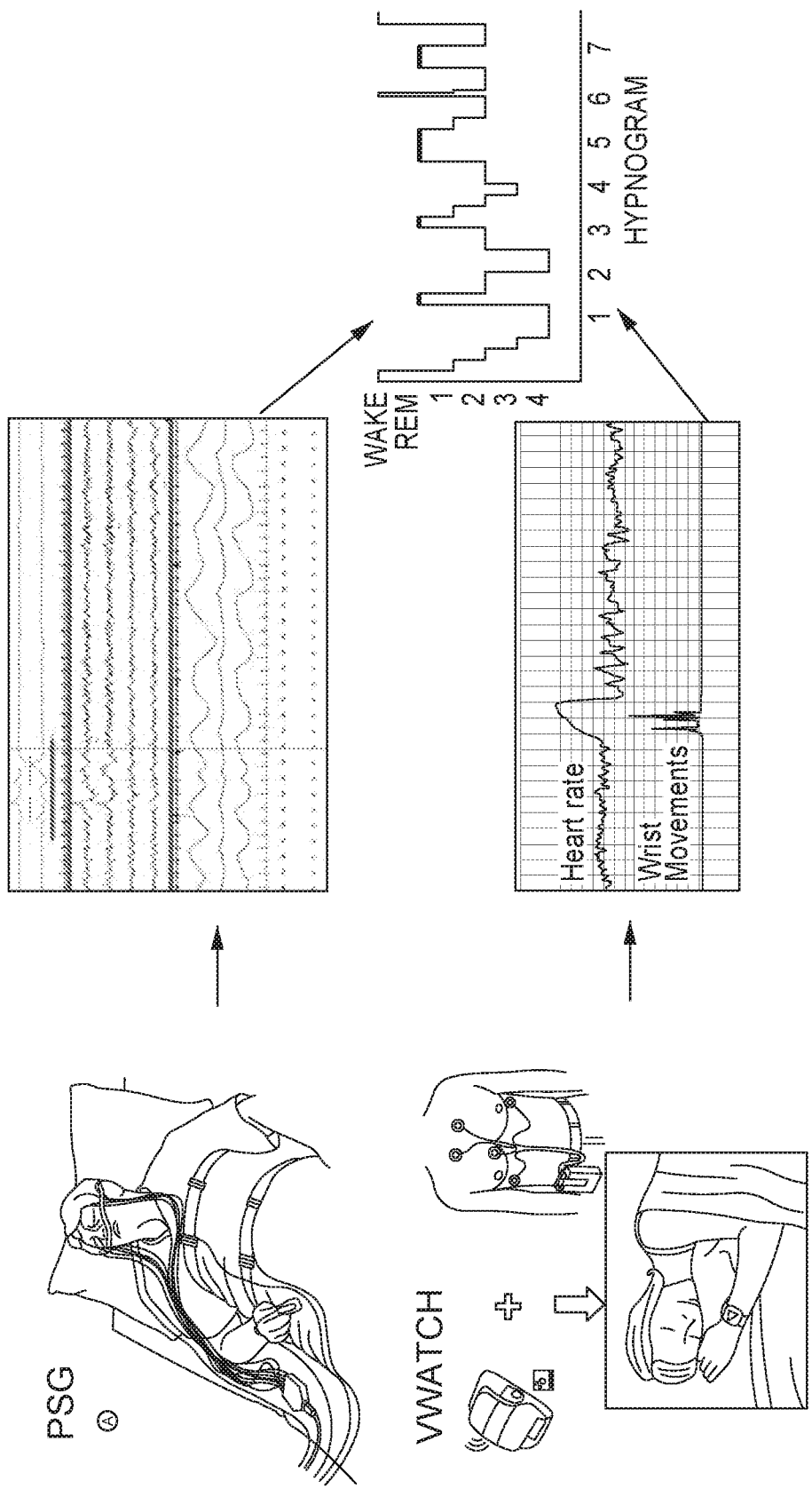
FIG. 6 is a diagram illustrating a scheme of monitoring sleep using PSG and V-Watch.

V-Watch: A Sleep Biomarker & Companion Diagnostic Tool
  VWatch methodology overview-1 (FIG. 6): Compared to the standard polysomnography (PSG) which rely on the measure of brain waves, V-Watch methodology uses physiological measures to assess sleep.
  Physiological systems and their regulations are dependent of the physiological state (waking or sleeping)
  The sleeping process affects the whole body and not only the brain
  Changes seen in cortical waves during sleep are only reflections of transitions between sleep stages and they are not the only method to assess these transitions
  These transitions can also be detected from other physiological systems
  Heart rate characteristics (level, regularity, variability and sudden changes) and body motor activity can be used to discriminate waking from sleeping and to distinguish the main sleep stages.

Example 3. Various Tablet Formulations of Compound (I)

TABLE 6-1

Compositions for 16 mg and 64 mg MIN-101 MR tablet formulations

| Composition | 117055-01-1 (16 mg Slow) | | | 117055-01-2 (64 mg Slow) | | | 117055-01-3 (16 mg Fast) | | | 117055-01-4 (64 mg Fast) | | |
|---|---|---|---|---|---|---|---|---|---|---|---|---|
| | % w/w | mg/tablet | g/per 50 g batch | % w/w | mg/tablet | g/per 50 g batch | % w/w | mg/tablet | g/per 50 g batch | % w/w | mg/tablet | g/per 50 g batch |
| MIN-101* | 5.33 | 16.0 | 2.67 | 21.33 | 64.0 | 10.67 | 5.33 | 16.0 | 2.67 | 21.33 | 64.0 | 10.67 |
| Hypromellose K4M CR | 30.00 | 90.0 | 15.00 | 30.00 | 90.0 | 15.00 | — | — | — | — | — | — |
| Hypromellose K100LV CR | — | — | — | — | — | — | 30.00 | 90.0 | 15.00 | 30.00 | 90.0 | 15.00 |
| Microcrystalline Cellulose PH102 | 62.67 | 188.0 | 31.34 | 46.67 | 140.0 | 23.34 | 62.67 | 188.0 | 31.34 | 46.67 | 140.0 | 23.34 |

TABLE 6-1-continued

Compositions for 16 mg and 64 mg MIN-101 MR tablet formulations

| | 117055-01-1 (16 mg Slow) | | | 117055-01-2 (64 mg Slow) | | | 117055-01-3 (16 mg Fast) | | | 117055-01-4 (64 mg Fast) | | |
|---|---|---|---|---|---|---|---|---|---|---|---|---|
| Composition | % w/w | mg/tablet | g/per 50 g batch | % w/w | mg/tablet | g/per 50 g batch | % w/w | mg/tablet | g/per 50 g batch | % w/w | mg/tablet | g/per 50 g batch |
| Silica Colloidal Anhydrous, Aerosil 200 Pharma | 1.00 | 3.0 | 0.50 | 1.00 | 3.0 | 0.50 | 1.00 | 3.0 | 0.50 | 1.00 | 3.0 | 0.50 |
| Magnesium stearate | 1.00 | 3.0 | 0.50 | 1.00 | 3.0 | 0.50 | 1.00 | 3.0 | 0.50 | 1.00 | 3.0 | 0.50 |
| Total | 100.00 | 300.0 | 50.01 | 100.00 | 300.0 | 50.01 | 100.00 | 300.0 | 50.0 | 100.00 | 300.0 | 50.01 |

*Salt correction factor missed in error

TABLE 6-2

Compositions for 16 mg and 64 mg MIN-101 MR tablet formulations

| | 117055-08-1 (16 mg Slow) | | | 117055-08-2 64 mg Slow | | | 117055-08-3 16 mg Fast | | | 117055-08-4 64 mg Fast | | |
|---|---|---|---|---|---|---|---|---|---|---|---|---|
| Composition | % w/w | mg/tablet | g/per 50 g batch | % w/w | mg/tablet | g/per 50 g batch | % w/w | mg/tablet | g/per 50 g batch | % w/w | mg/tablet | g/per 50 g batch |
| MIN-101* | 5.33 | 16.0 | 2.67 | 21.33 | 64.0 | 10.67 | 5.33 | 16.0 | 2.67 | 21.33 | 64.0 | 10.67 |
| Hypromellose K100LV CR | 35.00 | 105.0 | 17.50 | 35.00 | 105.0 | 17.50 | — | — | — | — | — | — |
| Hypromellose E50 | — | — | — | — | — | — | 20.0 | 60.0 | 10.00 | 20.0 | 60.0 | 10.00 |
| Microcrystalline Cellulose PH102 | 57.67 | 173.0 | 28.84 | 41.67 | 125.0 | 20.84 | 72.67 | 218.0 | 36.34 | 56.67 | 170.0 | 28.34 |
| Silica Colloidal Anhydrous, Aerosil 200 Pharma | 1.00 | 3.0 | 0.50 | 1.00 | 3.0 | 0.50 | 1.00 | 3.0 | 0.50 | 1.00 | 3.0 | 0.50 |
| Magnesium stearate | 1.00 | 3.0 | 0.50 | 1.00 | 3.0 | 0.50 | 1.00 | 3.0 | 0.50 | 1.00 | 3.0 | 0.50 |
| Total | 100.00 | 300.0 | 50.01 | 100.00 | 300.0 | 50.01 | 100.00 | 300.0 | 50.0 | 100.00 | 300.0 | 50.01 |

*Salt correction factor missed in error

TABLE 7

Compositions for 16 mg and 64 mg MIN-101 MR tablet formulations

| | 117055-11-1 (16 mg Slow) | | | 117055-11-2 64 mg Slow | | | 117055-11-3 16 mg Fast | | | 117055-11-4 64 mg Fast | | |
|---|---|---|---|---|---|---|---|---|---|---|---|---|
| Composition | % w/w | mg/tablet | g/per 50 g batch | % w/w | mg/tablet | g/per 50 g batch | % w/w | mg/tablet | g/per 50 g batch | % w/w | mg/tablet | g/per 50 g batch |
| MIN-101* | 6.4 | 19.2 | 3.2 | 25.6 | 76.8 | 12.8 | 6.4 | 19.2 | 3.2 | 25.6 | 76.8 | 12.8 |
| Hypromellose K100LV CR | 35.0 | 105.0 | 17.5 | 35.0 | 105.0 | 17.5 | — | — | — | — | — | — |
| Hypromellose E50 | — | — | — | — | — | — | 20.0 | 60.0 | 10.0 | 20.0 | 60.0 | 10.0 |
| Mannitol M200 | 56.6 | 169.3 | 28.3 | 37.4 | 112.2 | 18.7 | 71.6 | 214.8 | 35.8 | 52.4 | 157.2 | 26.2 |
| Silica Colloidal Anhydrous, Aerosil 200 Pharma | 1.0 | 3.0 | 0.5 | 1.0 | 3.0 | 0.5 | 1.0 | 3.0 | 0.5 | 1.0 | 3.0 | 0.5 |
| Magnesium stearate | 1.0 | 3.0 | 0.5 | 1.0 | 3.0 | 0.5 | 1.0 | 3.0 | 0.5 | 1.0 | 3.0 | 0.5 |
| Total | 100.00 | 300.0 | 50.0 | 100.0 | 300.0 | 50.0 | 100.0 | 300.0 | 50.0 | 100.0 | 300.0 | 50.0 |

*Salt correction factor of 1.2 applied.

TABLE 8

Compositions for 16 mg and 64 mg MIN-101 MR tablet formulations

| Composition | 117055-13-1 16 mg Slow | | | 117055-13-2 64 mg Slow | | | 117055-13-3 64 mg Slow | | | 117055-13-4 64 mg Slow | | | 117055-13-5 16 mg Fast | | | 117055-13-6 64 mg Fast | | |
|---|---|---|---|---|---|---|---|---|---|---|---|---|---|---|---|---|---|---|
| | % w/w | mg/tablet | g/per 50 g batch | % w/w | mg/tablet | g/per 50 g batch | % w/w | mg/tablet | g/per 50 g batch | % w/w | mg/tablet | g/per 50 g batch | % w/w | mg/tablet | g/per 50 g batch | % w/w | mg/tablet | g/per 50 g batch |
| MIN-101* | 6.4 | 19.2 | 3.20 | 25.6 | 76.8 | 12.80 | 25.6 | 76.8 | 12.8 | 25.6 | 76.8 | 12.8 | 8.4 | 19.2 | 3.2 | 25.6 | 76.8 | 12.8 |
| Hypromellose K100LV CR | 35.0 | 105.0 | 17.50 | 35.0 | 105.0 | 17.50 | 50.0 | 150.0 | 25.0 | — | — | — | 20.0 | 60.0 | 10.0 | 20.0 | 60.0 | 10.0 |
| Hypromellose K4M | — | — | — | — | — | — | — | — | — | 30.0 | 90.0 | 15.0 | — | — | — | — | — | — |
| Mannitol M200 | 28.3 | 84.9 | 14.15 | 18.7 | 56.1 | 9.35 | 22.4 | 67.2 | 11.2 | 42.4 | 127.2 | 21.2 | 71.6 | 214.8 | 35.8 | 52.4 | 157.2 | 26.2 |
| Microcrystalline Cellulose PH102 | 28.3 | 84.9 | 14.15 | 18.7 | 56.1 | 9.35 | — | — | — | — | — | — | — | — | — | — | — | — |
| Silica Colloidal Anhydrous, Aerosil 200 Pharma | 1.0 | 3.0 | 0.50 | 1.0 | 3.0 | 0.50 | 1.0 | 3.0 | 0.5 | 1.0 | 3.0 | 0.5 | 1.0 | 3.0 | 0.5 | 1.0 | 3.0 | 0.5 |
| Magnesium stearate | 1.0 | 3.0 | 0.50 | 1.0 | 3.0 | 0.50 | 1.0 | 3.0 | 0.5 | 1.0 | 3.0 | 0.5 | 1.0 | 3.0 | 0.5 | 1.0 | 3.0 | 0.5 |
| Total | 100.0 | 300.0 | 50.00 | 100.0 | 300.0 | 50.00 | 100.0 | 300.0 | 50.0 | 100.0 | 300.0 | 50.0 | 100.0 | 300.0 | 50.0 | 100.0 | 300.0 | 50.0 |

*Salt correction factor of 1.2 applied.

TABLE 9

Compositions for 64 mg MIN-101 MR tablet formulations

| Composition | 117055-17-1 (64 mg Slow) | | | 117055-17-2 (64 mg Slow) | | | 117055-17-3 (64 mg Fast) | | | 117055-17-4 (64 mg Fast) | | |
|---|---|---|---|---|---|---|---|---|---|---|---|---|
| | % w/w | mg/tablet | g/per 50 g batch | % w/w | mg/tablet | g/per 50 g batch | % w/w | mg/tablet | g/per 50 g batch | % w/w | mg/tablet | g/per 50 g batch |
| MIN-101* | 25.60 | 76.80 | 12.80 | 25.6 | 76.8 | 12.80 | 25.60 | 76.80 | 12.80 | 25.60 | 76.80 | 12.80 |
| Hypromellose K100LV CR | 50.00 | 150.00 | 25.00 | 50.0 | 150.0 | 25.00 | 20.00 | 60.00 | 10.00 | 20.00 | 60.00 | 10.00 |
| Mannitol M200 | 13.44 | 40.32 | 6.72 | 15.68 | 47.04 | 7.84 | 31.44 | 94.32 | 15.72 | 36.68 | 110.04 | 18.34 |
| Microcrystalline Cellulose PH102 | 8.96 | 26.88 | 4.48 | 6.72 | 20.16 | 3.36 | 20.96 | 62.88 | 10.48 | 15.72 | 47.16 | 7.86 |
| Silica Colloidal Anhydrous, Aerosil 200 Pharma | 1.00 | 3.00 | 0.50 | 1.0 | 3.0 | 0.50 | 1.00 | 3.00 | 0.50 | 1.00 | 3.00 | 0.50 |
| Magnesium stearate | 1.00 | 3.00 | 0.50 | 1.0 | 3.0 | 0.50 | 1.00 | 3.00 | 0.50 | 1.00 | 3.00 | 0.50 |
| Total | 100.0 | 300.00 | 50.00 | 100.00 | 300.00 | 50.00 | 100.00 | 300.00 | 50.0 | 100.00 | 300.00 | 50.0 |

*Salt correction factor of 1.2 applied.

TABLE 10

Compositions for 16 mg and 64 mg MIN-101 MR tablet formulations

| Composition | 117055-21-1 64 mg Fast | | | 117055-21-2 64 mg Fast | | | 117055-21-3 16 mg Fast | | |
|---|---|---|---|---|---|---|---|---|---|
| | % w/w | mg/tablet | g/per 50 g batch | % w/w | mg/tablet | g/per 50 g batch | % w/w | mg/tablet | g/per 50 g batch |
| MIN-101* | 25.60 | 76.80 | 12.80 | 25.60 | 76.80 | 12.80 | 6.40 | 19.20 | 3.20 |
| Hypromellose K100LV CR | 25.00 | 75.00 | 12.50 | 25.00 | 75.00 | 12.50 | 25.00 | 75.00 | 12.50 |
| Mannitol M200 | 28.44 | 85.32 | 14.22 | 33.18 | 99.54 | 16.59 | 46.62 | 139.86 | 23.31 |
| Microcrystalline Cellulose PH102 | 18.96 | 56.88 | 9.48 | 14.22 | 42.66 | 7.11 | 19.98 | 59.94 | 9.99 |

TABLE 10-continued

Compositions for 16 mg and 64 mg MIN-101 MR tablet formulations

| | | | | | | | | | |
|---|---|---|---|---|---|---|---|---|---|
| Silica Colloidal Anhydrous, Aerosil 200 Pharma | 1.00 | 3.00 | 0.50 | 1.00 | 3.00 | 0.50 | 1.00 | 3.00 | 0.50 |
| Magnesium stearate | 1.00 | 3.00 | 0.50 | 1.00 | 3.00 | 0.50 | 1.00 | 3.00 | 0.50 |
| Total | 100.00 | 300.00 | 50.00 | 100.00 | 300.00 | 50.00 | 100.00 | 300.00 | 50.00 |

| | 117055-24-1 16 mg Slow | | | 117055-24-2 16 mg Slow | | | 117055-24-3 16 mg Slow | | |
|---|---|---|---|---|---|---|---|---|---|
| Composition | % w/w | mg/tablet | g/per 50 g batch | % w/w | mg/tablet | g/per 50 g batch | % w/w | mg/tablet | g/per 50 g batch |
| MIN-101* | 6.40 | 19.20 | 3.20 | 6.40 | 19.20 | 3.20 | 6.40 | 19.20 | 3.20 |
| Hypromellose K100LV CR | 50.00 | 150.00 | 25.00 | 50.00 | 150.00 | 25.00 | 55.00 | 165.00 | 27.50 |
| Mannitol M200 | 24.96 | 74.88 | 12.48 | 29.12 | 87.36 | 14.56 | 25.62 | 76.86 | 12.81 |
| Microcrystalline Cellulose PH102 | 16.64 | 49.92 | 8.32 | 12.48 | 37.44 | 6.24 | 10.98 | 32.94 | 5.49 |
| Silica Colloidal Anhydrous, Aerosil 200 Pharma | 1.00 | 3.00 | 0.50 | 1.00 | 3.00 | 0.50 | 1.00 | 3.00 | 0.50 |
| Magnesium stearate | 1.00 | 3.00 | 0.50 | 1.00 | 3.00 | 0.50 | 1.00 | 3.00 | 0.50 |
| Total | 100.00 | 300.00 | 50.00 | 100.00 | 300.00 | 50.00 | 100.00 | 300.00 | 50.00 |

TABLE 11

Compositions for 16 mg and 64 mg MIN-101 MR tablet formulations

| | 117055-26-1 16 mg Slow | | | 117055-26-2 64 mg Slow | | | 117055-26-3 16 mg Fast | | | 117055-26-3 64 mg Fast | | |
|---|---|---|---|---|---|---|---|---|---|---|---|---|
| Composition | % w/w | mg/tablet | g/per 50 g batch | % w/w | mg/tablet | g/per 50 g batch | % w/w | mg/tablet | g/per 50 g batch | % w/w | mg/tablet | g/per 50 g batch |
| MIN-101* | 6.40 | 19.20 | 3.20 | 25.6 | 76.80 | 12.80 | 6.40 | 19.20 | 3.20 | 25.60 | 76.80 | 12.80 |
| Hypromellose K100LV CR | 55.00 | 165.00 | 27.50 | 50.00 | 150.00 | 25.00 | 27.00 | 81.00 | 13.50 | 22.00 | 66.00 | 11.00 |
| Mannitol M200 | 25.62 | 76.86 | 12.81 | 15.68 | 47.04 | 7.84 | 45.22 | 135.66 | 22.61 | 35.28 | 105.84 | 17.64 |
| Microcrystalline Cellulose PH102 | 10.98 | 32.94 | 5.49 | 6.72 | 20.16 | 3.36 | 19.38 | 58.04 | 9.69 | 15.12 | 45.36 | 7.56 |
| Silica Colloidal Anhydrous, Aerosil 200 Pharma | 1.00 | 3.00 | 0.50 | 1.00 | 3.00 | 0.50 | 1.00 | 3.00 | 0.50 | 1.00 | 3.00 | 0.50 |
| Magnesium stearate | 1.00 | 3.00 | 0.50 | 1.00 | 3.00 | 0.50 | 1.00 | 3.00 | 0.50 | 1.00 | 3.00 | 0.50 |
| Total | 100.00 | 300.00 | 50.00 | 100.00 | 300.00 | 50.00 | 100.00 | 300.00 | 50.00 | 100.00 | 300.00 | 50.00 |

*Salt correction factor of 1.2 applied.

TABLE 12

Compositions for 16 mg and 64 mg MIN-101 MR tablet formulations

| | 117055-30-1 16 mg Fast | | | 117055-30-2 64 mg Fast | | | 117055-30-3 16 mg Fast | | |
|---|---|---|---|---|---|---|---|---|---|
| Composition | % w/w | mg/tablet | g/per 50 g batch | % w/w | mg/tablet | g/per 50 g batch | % w/w | mg/tablet | g/per 50 g batch |
| MIN-101* | 6.40 | 19.20 | 3.20 | 25.60 | 76.80 | 12.80 | 6.40 | 19.20 | 3.20 |
| Hypromellose K100LV CR | 27.00 | 81.00 | 13.50 | 22.00 | 66.00 | 11.00 | 30.00 | 90.00 | 15.00 |

TABLE 12-continued

Compositions for 16 mg and 64 mg MIN-101 MR tablet formulations

| | | | | | | | | | |
|---|---|---|---|---|---|---|---|---|---|
| Mannitol M200 | 45.22 | 135.66 | 22.61 | 35.28 | 105.84 | 17.64 | 43.12 | 129.36 | 21.56 |
| Microcrystalline Cellulose PH102 | 19.38 | 58.14 | 9.69 | 15.12 | 45.36 | 7.56 | 18.48 | 55.44 | 9.24 |
| Silica Colloidal Anhydrous, Aerosil 200 Pharma | 1.00 | 3.00 | 0.50 | 1.00 | 3.00 | 0.50 | 1.00 | 3.00 | 0.50 |
| Magnesium stearate | 1.00 | 3.00 | 0.50 | 1.00 | 3.00 | 0.50 | 1.00 | 3.00 | 0.50 |
| Total | 100.00 | 300.00 | 50.00 | 100.00 | 300.00 | 50.00 | 100.00 | 300.0 | 50.00 |

| | 117055-33-1 16 mg Slow | | | 117055-33-2 64 mg Slow | | | 117055-33-3 16 mg Slow | | |
|---|---|---|---|---|---|---|---|---|---|
| Composition | % w/w | mg/tablet | g/per 50 g batch | % w/w | mg/tablet | g/per 50 g batch | % w/w | mg/tablet | g/per 50 g batch |
| MIN-101* | 6.40 | 19.20 | 3.20 | 25.6 | 76.80 | 12.80 | 6.40 | 19.20 | 3.20 |
| Hypromellose K100LV CR | 55.00 | 165.00 | 27.50 | 50.00 | 150.00 | 25.00 | 58.00 | 174.00 | 29.00 |
| Mannitol M200 | 25.62 | 76.86 | 12.81 | 15.68 | 47.04 | 7.84 | 23.52 | 70.56 | 11.76 |
| Microcrystalline Cellulose PH102 | 10.98 | 32.94 | 5.49 | 6.72 | 20.16 | 3.36 | 10.08 | 30.24 | 5.04 |
| Silica Colloidal Anhydrous, Aerosil 200 Pharma | 1.00 | 3.00 | 0.50 | 1.00 | 3.00 | 0.50 | 1.00 | 3.00 | 0.50 |
| Magnesium stearate | 1.00 | 3.00 | 0.50 | 1.00 | 3.00 | 0.50 | 1.00 | 3.00 | 0.50 |
| Total | 100.00 | 300.00 | 50.00 | 100.00 | 300.00 | 50.00 | 100.00 | 300.00 | 50.00 |

*Salt correction factor of 1.2 applied.

TABLE 13

Compositions for 16 mg and 64 mg MIN-101 MR tablet formulations

| | 117055-38-1 16 mg Slow | | | 117055-38-2 64 mg Slow | | | 117055-38-3 16 mg Fast | | | 117055-38-4 64 mg Fast | | |
|---|---|---|---|---|---|---|---|---|---|---|---|---|
| Composition | % w/w | mg/tablet | g/per 50 g batch | % w/w | mg/tablet | g/per 50 g batch | % w/w | mg/tablet | g/per 50 g batch | % w/w | mg/tablet | g/per 50 g batch |
| MIN-101* | 6.40 | 19.20 | 3.20 | 25.6 | 76.80 | 12.80 | 6.40 | 19.20 | 3.20 | 25.60 | 76.80 | 12.80 |
| Hypromellose K100LV CR | 40.00 | 120.00 | 20.00 | 45.00 | 135.00 | 22.50 | 25.00 | 75.00 | 12.50 | 20.00 | 60.00 | 10.00 |
| Mannitol M200 | 36.47 | 109.41 | 18.24 | 19.53 | 58.59 | 9.77 | 46.97 | 140.91 | 23.49 | 37.03 | 111.09 | 18.52 |
| Microcrystalline Cellulose PH102 | 15.53 | 46.89 | 7.82 | 8.37 | 25.11 | 4.19 | 20.13 | 60.39 | 10.07 | 15.87 | 47.61 | 7.94 |
| Silica Colloidal Anhydrous, Aerosil 200 Pharma | 1.00 | 1.50 | 0.25 | 0.50 | 1.50 | 0.25 | 0.50 | 1.50 | 0.25 | 0.50 | 1.50 | 0.25 |
| Magnesium stearate | 1.00 | 3.00 | 0.50 | 1.00 | 3.00 | 0.50 | 1.00 | 3.00 | 0.50 | 1.00 | 3.00 | 0.50 |
| Total | 100.00 | 300.00 | 50.01 | 100.00 | 300.00 | 50.01 | 100.00 | 300.00 | 50.01 | 100.00 | 300.00 | 50.01 |

*Salt correction factor of 1.2 applied.

TABLE 14

Analytical investigation for 64 mg MIN-101 MR tablet formulations (64 mg slow of Experiment 9)

| Experiment | Mean Percentage Label Claim (%) |
|---|---|
| 2 hour automatic time point (pulled through a 10 μm free flow filter) | 30.3% |
| 2 hour manual time point no filtration | 30.9% |
| 19 hour automatic time point (pulled through a 10 μm fee flow filter) | 82.0% |
| 19 hour manual time point no filtration | 82.6% |
| 19 hour manual time point centrifuged | 82.2% |
| 19 hour manual time point filtered through a 0.45 μm PTFE syringe filter | 82.8% |

TABLE 15

Compositions for 64 mg MIN-101 MR tablet formulations

| | 117055-46-1; 64 mg Slow | | |
|---|---|---|---|
| Composition | % w/w | mg/tablet | g/per 50 g batch |
| MN-101* | 25.6 | 76.80 | 12.80 |
| Hypromellose K100LV CR | 45.00 | 135.00 | 22.50 |
| Mannitol M200 | 19.53 | 58.59 | 9.77 |
| Microcrystalline Cellulose PH102 | 8.37 | 25.11 | 4.19 |
| Silica Colloidal Anhydrous, Aerosil 200 Pharma | 0.50 | 1.50 | 0.25 |
| Magnesium stearate | 1.00 | 3.00 | 0.50 |
| Total | 100.00 | 300.00 | 50.01 |

*Salt correction factor of 1.2 applied.

TABLE 16

Compositions for 16 mg and 64 mg MIN-101 MR tablet formulations

| | 117055-48-1 16 mg Slow | | | 117055-48-2 64 mg Slow | | | 117055-48-3 16 mg Fast | | | 117055-48-4 64 mg Fast | | |
|---|---|---|---|---|---|---|---|---|---|---|---|---|
| Composition | % w/w | mg/tablet | g/per 50 g batch | % w/w | mg/tablet | g/per 50 g batch | % w/w | mg/tablet | g/per 50 g batch | % w/w | mg/tablet | g/per 50 g batch |
| MIN-101* | 6.40 | 19.20 | 3.20 | 25.60 | 76.80 | 12.80 | 6.40 | 19.20 | 3.20 | 25.50 | 76.80 | 12.80 |
| Hypromellose K100LV CR | 55.00 | 165.00 | 27.50 | 50.00 | 150.00 | 25.00 | 25.00 | 75.00 | 12.50 | 20.00 | 60.00 | 10.00 |
| Mannitol M200 | 25.97 | 77.91 | 12.99 | 16.03 | 48.09 | 8.02 | 46.97 | 140.91 | 23.49 | 37.03 | 111.09 | 18.52 |
| Microcrystalline Cellulose PH102 | 11.13 | 33.39 | 5.57 | 6.87 | 20.61 | 3.44 | 20.13 | 60.39 | 10.07 | 15.87 | 47.61 | 7.94 |
| Sillica Colloidal Anhydrous, Aerosil 200 Pharma | 0.50 | 1.50 | 0.25 | 0.50 | 1.50 | 0.25 | 0.50 | 1.50 | 0.25 | 0.50 | 1.50 | 0.25 |
| Magnesium stearate | 1.00 | 3.00 | 0.50 | 1.00 | 3.00 | 0.50 | 1.00 | 3.00 | 0.5 | 1.00 | 3.00 | 0.50 |
| Total | 100.00 | 300.00 | 50.01 | 100.00 | 300.00 | 50.01 | 100.00 | 300.00 | 50.01 | 100.00 | 300.00 | 50.01 |

*Salt correction factor of 1.2 applied.

TABLE 17

Compositions for 16 mg and 64 mg MIN-101 MR tablet formulations

| | 117055-52-1 16 mg Slow | | | 117055-52-2 64 mg Slow | | |
|---|---|---|---|---|---|---|
| Composition | % w/w | mg/tablet | g/per 50 g batch | % w/w | mg/tablet | g/per 50 g batch |
| MIN-101* | 6.40 | 19.20 | 3.20 | 25.60 | 76.80 | 12.80 |
| Hypromellose K4M CR | 36.00 | 108.00 | 18.00 | 30.00 | 90.00 | 15.00 |
| Microcrystalline Cellulose PH102 | 36.10 | 108.30 | 18.05 | 22.90 | 68.70 | 11.45 |
| Lactose Fastflo 316 | 20.00 | 60.00 | 10.00 | 20.00 | 60.00 | 10.00 |
| Sillica Colloidal Anhydrous, Aerosil 200 Pharma | 0.50 | 1.50 | 0.25 | 0.50 | 1.50 | 0.25 |
| Magnesium stearate | 1.00 | 3.00 | 0.50 | 1.00 | 3.00 | 0.50 |
| Total | 100.00 | 300.00 | 50.00 | 100.00 | 300.00 | 50.01 |

*Salt correction factor of 1.2 applied.

TABLE 18

Compositions for 16 mg and 64 mg MIN-101 MR tablet formulations

| Composition | 117055-54-1; 64 mg Fast | | | 117055-54-2; 16 mg Fast | | | 117055-54-3; 16 mg Fast | | |
|---|---|---|---|---|---|---|---|---|---|
| | % w/w | mg/tablet | g/per 50 g batch | % w/w | mg/tablet | g/per 50 g batch | % w/w | mg/tablet | g/per 50 g batch |
| MIN-101* | 25.60 | 76.80 | 12.80 | 6.40 | 19.20 | 3.20 | 6.40 | 19.20 | 3.20 |
| Hypromellose K100LV CR | 30.00 | 90.00 | 15.00 | 36.00 | 108.00 | 18.00 | 30.00 | 90.00 | 15.00 |
| Hypromellose K4M CR | — | — | — | — | — | — | 6.00 | 18.00 | 3.00 |
| Microcrystalline Cellulose PH102 | 22.90 | 68.70 | 11.45 | 36.10 | 108.3 | 18.05 | 36.10 | 108.3 | 18.05 |
| Lactose Fastflo 316 | 20.00 | 60.00 | 10.00 | 20.00 | 60.00 | 10.00 | 20.00 | 60.00 | 10.00 |
| Silica Colloidal Anhydrous, Aerosil 200 Pharma | 0.50 | 1.50 | 0.25 | 0.50 | 1.50 | 0.25 | 0.50 | 1.50 | 0.25 |
| Magnesium stearate | 1.00 | 3.00 | 0.50 | 1.00 | 3.00 | 0.50 | 1.00 | 3.00 | 0.50 |
| Total | 100.00 | 300.00 | 50.00 | 100.00 | 300.00 | 50.00 | 100.00 | 300.00 | 50.00 |

*Salt correction factor of 1.2 applied.

TABLE 19

Compositions for 16 mg and 64 mg MIN-101 MR tablet formulations

| Composition | 117055-55-1 64 mg Fast | | | 117055-55-2 16 mg Fast | | | 117055-55-3 64 mg Slow | | |
|---|---|---|---|---|---|---|---|---|---|
| | % w/w | mg/tablet | g/per 50 g batch | % w/w | mg/tablet | g/per 50 g batch | % w/w | mg/tablet | g/per 50 g batch |
| MIN-101* | 25.60 | 76.80 | 12.80 | 6.40 | 19.20 | 3.20 | 25.60 | 76.80 | 12.80 |
| Hypromellose K100LV CR | 30.00 | 90.00 | 15.00 | 30.00 | 108.00 | 18.00 | 6.00 | 18.00 | 3.00 |
| Hypromellose K4M CR | — | — | — | — | — | — | 24.00 | 72.00 | 12.00 |
| Microcrystalline Cellulose PH102 | 22.90 | 68.70 | 11.45 | 36.10 | 108.3 | 18.05 | 22.90 | 68.70 | 11.45 |
| Lactose Fastflo 316 | 20.00 | 60.00 | 10.00 | 20.00 | 60.00 | 10.00 | 20.00 | 60.00 | 10.00 |
| Silica Colloidal Anhydrous Aerosil 200 Pharma | 0.50 | 1.50 | 0.25 | 0.50 | 1.50 | 0.25 | 0.50 | 1.50 | 0.25 |
| Magnesium stearate | 1.00 | 3.00 | 0.50 | 1.00 | 3.00 | 0.50 | 1.00 | 3.00 | 0.50 |
| Total | 100.00 | 300.0 | 50.00 | 100.00 | 300.00 | 50.00 | 100.00 | 300.00 | 50.00 |

| Composition | 117055-55-4 16 mg Slow | | | 117055-58-1 40 mg Medium | | | 117055-58-2 32 mg Slow | | |
|---|---|---|---|---|---|---|---|---|---|
| | % w/w | mg/tablet | g/per 50 g batch | % w/w | mg/tablet | g/per 50 g batch | % w/w | mg/tablet | g/per 50 g batch |
| MIN-101* | 6.40 | 19.20 | 3.20 | 16.00 | 48.00 | 8.00 | 12.80 | 38.40 | 6.40 |
| Hypromellose K100LV CR | 12.00 | 36.00 | 6.00 | 21.00 | 63.00 | 10.5 | 10.00 | 30.00 | 5.00 |
| Hypromellose K4M CR | 24.00 | 72.00 | 12.00 | 12.00 | 36.00 | 6.00 | 24.00 | 72.00 | 12.00 |
| Microcrystalline Cellulose PH102 | 36.10 | 108.3 | 18.05 | 29.50 | 88.50 | 14.75 | 31.70 | 95.10 | 15.85 |
| Lactose Fastflo 316 | 20.00 | 60.00 | 10.00 | 20.00 | 60.00 | 10.00 | 20.00 | 60.00 | 10.00 |

TABLE 19-continued

Compositions for 16 mg and 64 mg MIN-101 MR tablet formulations

| | | | | | | | | | |
|---|---|---|---|---|---|---|---|---|---|
| Silica Colloidal Anhydrous Aerosil 200 Pharma | 0.50 | 1.50 | 0.25 | 0.50 | 1.50 | 0.25 | 0.50 | 1.50 | 0.25 |
| Magnesium stearate | 1.00 | 3.00 | 0.50 | 1.00 | 3.00 | 0.50 | 1.00 | 3.00 | 0.50 |
| Total | 100.00 | 300.00 | 50.00 | 100.00 | 300.00 | 50.00 | 100.00 | 300.00 | 50.00 |

*Salt correction factor of 1.2 applied.

TABLE 20

Batch Formula for reference MIN-101 SR tablets

| Component | Function | % w/w | mg/tablet | g/per 200 g batch (up to 1333 tablets) |
|---|---|---|---|---|
| Intragranular blend | | | | |
| MIN101 drag substance[1] | Drag substance | 6.40 | 9.60 | 12.80 |
| Kolliwax HCO | Lubricant | 20.00 | 30.00 | 40.00 |
| Lactose (Pharmatose 200) | Filler | 58.93 | 88.40 | 117.86 |
| Microcrystalline Cellulose (Vivapur 101) | Filler | 10.00 | 15.00 | 20.00 |
| Hydroxypropylcellulose (HPC-L) | Binder | 2.80 | 4.20 | 5.60 |
| Silica Colloidal Anhydrous (Aerosil 200) | Glidant | 0.13 | 0.20 | 0.26 |
| Citric Acid Monohydrate | pH adjuster | 0.67 | 1.00 | 1.34 |
| Sterile Water for Irrigation[2] | Process aid | q.s | — | q.s |
| Sub-total | — | 98.93 | 148.40 | 197.86 |
| Extragranular blend[3] | | | | |
| Magnesium Stearate (Hyqual) | Lubricant | 1.07 | 1.60 | 2.14 |
| Core tablet weight | — | 100.00 | 150.00 | 200.00 |

[1]Salt conversion factor of 1.2 i.e. 9.60 mg of MIN-101 hydrochloride form drug substance equivalent to 8.0 mg of MIN-101 free base.
[2]Sterile Water for Irrigation was used for wet granulation and was removed during the drying step.
[3]Final extragranular blend for tableting was calculated based on the yield of intragranular blend available

TABLE 21

Compositions for 16 mg and 64 mg MIN-101 MR tablet formulations (manufacturing process development)

| | 117055-60 64 mg Fast | | | 117055-61 16 mg Fast | | | 117055-62 64 mg Slow | | |
|---|---|---|---|---|---|---|---|---|---|
| Composition | % w/w | mg/ tablet | g/per 100 g batch | % w/w | mg/ tablet | g/per 100 g batch | % w/w | mg/ tablet | g/per 100 g batch |
| MIN-101* | 25.60 | 76.80 | 25.60 | 6.40 | 19.20 | 6.40 | 25.60 | 76.80 | 25.60 |
| Hypromellose K100LV CR | 30.00 | 90.00 | 30.00 | 36.00 | 108.00 | 36.00 | 6.00 | 18.00 | 6.00 |
| Hypromellose K4M CR | — | — | — | — | — | — | 24.00 | 72.00 | 24.00 |
| Microcrystalline Cellulose PH102 | 22.90 | 68.70 | 22.90 | 36.10 | 108.3 | 36.10 | 22.90 | 68.70 | 22.90 |
| Lactose Fastflo 316 | 20.00 | 60.00 | 20.00 | 20.00 | 60.00 | 20.00 | 20.00 | 60.00 | 20.00 |
| Silica Colloidal Anhydrous, Aerosil 200 Pharma | 0.50 | 1.50 | 0.50 | 0.50 | 1.50 | 0.50 | 0.50 | 1.50 | 0.50 |
| Magnesium stearate | 1.00 | 3.00 | 1.00 | 1.00 | 3.00 | 1.00 | 1.00 | 3.00 | 1.00 |
| Total | 100.00 | 300.00 | 100.00 | 100.00 | 300.00 | 100.00 | 100.00 | 300.00 | 100.00 |

TABLE 21-continued

Compositions for 16 mg and 64 mg MIN-101 MR tablet formulations (manufacturing process development)

|  | 117055-63 16 mg Slow | | | 117055-64 40 mg Medium | | |
|---|---|---|---|---|---|---|
| Composition | % w/w | mg/ tablet | g/per 100 g batch | % w/w | mg/ tablet | g/per 100 g batch |
| MIN-101* | 6.40 | 19.20 | 6.40 | 16.00 | 48.00 | 16.00 |
| Hypromellose K100LV CR | 12.00 | 36.00 | 12.00 | 21.00 | 63.00 | 21.00 |
| Hypromellose K4M CR | 24.00 | 72.00 | 24.00 | 12.00 | 36.00 | 12.00 |
| Microcrystalline Cellulose PH102 | 36.10 | 108.3 | 36.10 | 29.50 | 88.50 | 29.50 |
| Lactose Fastflo 316 | 20.00 | 60.00 | 20.00 | 20.00 | 60.00 | 20.00 |
| Silica Colloidal Anhydrous, Aerosil 200 Pharma | 0.50 | 1.50 | 0.50 | 0.50 | 1.50 | 0.50 |
| Magnesium stearate | 1.00 | 3.00 | 1.00 | 1.00 | 3.00 | 1.00 |
| Total | 100.00 | 300.00 | 100.00 | 100.00 | 300.00 | 100.00 |

*Salt correction factor of 1.2 applied.

Example 4: Preparation of Form (A) of Compound (I).HCl.2H$_2$O 2-((1-(2-(4-Fluorophenyl)-2-oxoethyl)piperidin-4-yl)methyl)isoindolin-1-one, i.e., the free base of Compound (I), is dissolved in acetone and filtered through amorphous volcanic glass, i.e., Perlite®, to remove any foreign matter. To this solution is added 2 mol/L-hydrochloric acid water solution, i.e., 2 N HCl). The mixture is cooled while stirring for several hours and crude crystals of the hydrochloric acid salt of Compound (I) are filtered and dried under reduced pressure. The crude crystals are then purified by heating the crude material in acetone and deionized water and stirring for several hours. Foreign matter is then removed by filtration and then additional acetone is added to the filtrate. The mixture is cooled and the crystals are filtered and dried under reduced pressure to provide Form (A) of Compound (I).HCl.2H$_2$O.

Example 5: X-Ray Powder Diffraction of Form (A) of Compound (I).HCl.2H$_2$O

X-ray diffractometry was performed using RIGAKU, RINT 2500. The X-ray powder diffraction of Form (A) of Compound (I).HCl.2H$_2$O is shown in FIG. 11.

Example 6: IR Absorption Spectrum of Form (A) of Compound (I).HCl.2H$_2$O

Infrared (IR) absorption spectrometry was performed using Perkin-Elmer, Paragon1000. The IR spectrum of Form (A) of Compound (I).HCl.2H$_2$O was measured by a potassium chloride disk method as shown in FIG. 12. The main wave numbers of absorption and their assignment are as follows:

TABLE 22

Assignments of Form (A) of Compound (I)•HCl•2H$_2$O IR Spectrum

| Wave number (cm$^{-1}$) | Assignment |
|---|---|
| 2916 | C—H stretching vibration |
| 1684, 1665 | C=O stretching vibration |
| 1594 | Benzene ring |
| 1235 | C—F stretching vibration |

Example 7: Nuclear Magnetic Resonance Spectrometry of Form (A) of Compound (I).HCl.2H$_2$O $^1$H-NMR spectrum and $^{13}$C-NMR spectrum of Form (A) of Compound (I).HCl.2H$_2$O measured in d$_6$-dimethyl sulfoxide is shown in FIG. 13 and FIG. 14, respectively.

INCORPORATION BY REFERENCE

The entire disclosure of each of the patent documents and scientific articles referred to herein is incorporated by reference for all purposes.

EQUIVALENTS

The disclosure of the application can be embodied in other specific forms without departing from the spirit or essential characteristics thereof. The foregoing embodiments are therefore to be considered in all respects illustrative rather than limiting on the disclosure of the application described herein. Scope of the disclosure of the application is thus indicated by the appended claims rather than by the foregoing description, and all changes that come within the meaning and range of equivalency of the claims are intended to be embraced therein.

What is claimed is:

1. A pharmaceutical formulation comprising a release modifier and between about 1 mg and about 100 mg of Compound (I), (I)

or a pharmaceutically acceptable salt or solvate thereof, provided that when the formulation is administered to a human, the maximum plasma concentration ($C_{max}$) of BFB-520 detected in the human is below 10.0 ng/mL, wherein BFB-520 is an active metabolite of Compound (I).

2. The pharmaceutical formulation of claim 1, provided that when the formulation is administered to a human, the maximum plasma concentration ($C_{max}$) of BFB-520 detected in the human is below 5.0 ng/mL.

3. The pharmaceutical formulation of claim 1, provided that when the formulation is administered to a human, the area under the curve (AUC) of BFB-520 detected in the human is below 40 hr*ng/mL.

4. The pharmaceutical formulation of claim 1, provided that when the formulation is administered to a human, the AUC of BFB-520 detected in the human is below 20 hr*ng/mL.

5. The pharmaceutical formulation of claim 1, wherein the release modifier is a hypromellose.

6. The pharmaceutical formulation of claim 5, wherein the formulation further comprises a filler, a glidant, and a lubricant.

7. The pharmaceutical formulation of claim 6, wherein the formulation comprises 32 mg or 64 mg of Compound (I).

8. The pharmaceutical formulation of claim 7, which is in the form of a tablet.

9. A pharmaceutical formulation comprising a release modifier and between about 1 mg and about 100 mg of Compound (I), (I)

or a pharmaceutically acceptable salt or solvate thereof, provided that when the formulation is administered to a human, the maximum plasma concentration ($C_{max}$) of BFB-999 detected in the human is below 5.0 ng/mL, wherein BFB-999 is an active metabolite of Compound (I).

10. The pharmaceutical formulation of claim 9, provided that when the formulation is administered to a human, the maximum plasma concentration ($C_{max}$) of BFB-999 detected in the human is below 2.5 ng/mL.

11. The pharmaceutical formulation of claim 9, provided that when the formulation is administered to a human, the area under the curve (AUC) of BFB-999 detected in the human is below 40 hr*ng/mL.

12. The pharmaceutical formulation of claim 9, provided that when the formulation is administered to a human, the AUC of BFB-999 detected in the human is below 20 hr*ng/mL.

13. The pharmaceutical formulation of claim 9, wherein the release modifier is a hypromellose.

14. The pharmaceutical formulation of claim 13, wherein the formulation further comprises a filler, a glidant, and a lubricant.

15. The pharmaceutical formulation of claim 14, wherein the formulation comprises 32 mg or 64 mg of Compound (I).

16. The pharmaceutical formulation of claim 15, which is in the form of a tablet.

17. A tablet comprising a release modifier and between about 1 mg and about 100 mg of Compound (I), (I)

or a pharmaceutically acceptable salt or solvate thereof, provided that when the tablet is administered to a human, the maximum plasma concentration ($C_{max}$) of BFB-520 detected in the human is below 10.0 ng/mL, wherein BFB-520 is an active metabolite of Compound (I).

18. The tablet of claim 17, wherein the tablet further comprises one or more of a filler, a glidant, or a lubricant.

19. A tablet comprising a release modifier and between about 1 mg and about 100 mg of Compound (I), (I)

or a pharmaceutically acceptable salt or solvate thereof, provided that when the tablet is administered to a human, the maximum plasma concentration ($C_{max}$) of BFB-999 detected in the human is below 5.0 ng/mL, wherein BFB-999 is an active metabolite of Compound (I).

20. The tablet of claim 19, wherein the tablet further comprises one or more of a filler, a glidant, or a lubricant.

* * * * *